US011648260B2

(12) United States Patent
Levenberg et al.

(10) Patent No.: US 11,648,260 B2
(45) Date of Patent: May 16, 2023

(54) VESICLES COMPRISING A PTEN INHIBITOR AND USES OF SAME

(71) Applicants: TECHNION RESEARCH AND DEVELOPMENT FOUNDATION LIMITED, Haifa (IL); RAMOT AT TEL-AVIV UNIVERSITY LTD., Tel Aviv (IL)

(72) Inventors: Shulamit Levenberg, Moreshet (IL); Shaowei Guo, Haifa (IL); Daniel Offen, Tel Aviv (IL); Nisim Perets, Tel Aviv (IL)

(73) Assignees: TECHNION RESEARCH AND DEVELOPMENT FOUNDATION LIMITTED, Haifa (IL); RAMOT AT TEL-AVIV UNIVERSITY LTD., Tel Aviv (IL)

( * ) Notice: Subject to any disclaimer, the term of this patent is extended or adjusted under 35 U.S.C. 154(b) by 0 days.

(21) Appl. No.: 17/042,441

(22) PCT Filed: Mar. 27, 2019

(86) PCT No.: PCT/IL2019/050355
§ 371 (c)(1),
(2) Date: Sep. 28, 2020

(87) PCT Pub. No.: WO2019/186558
PCT Pub. Date: Oct. 3, 2019

(65) Prior Publication Data
US 2021/0077520 A1    Mar. 18, 2021

Related U.S. Application Data

(60) Provisional application No. 62/649,648, filed on Mar. 29, 2018.

(51) Int. Cl.
| C07H 21/02 | (2006.01) |
| C07H 21/04 | (2006.01) |
| A61K 31/713 | (2006.01) |
| A61K 35/28 | (2015.01) |
| A61K 38/51 | (2006.01) |
| C12N 15/113 | (2010.01) |
| A61K 9/50 | (2006.01) |
| C12N 15/11 | (2006.01) |
| A61K 9/127 | (2006.01) |

(52) U.S. Cl.
CPC .......... *A61K 31/713* (2013.01); *A61K 9/5068* (2013.01); *A61K 35/28* (2013.01); *A61K 38/51* (2013.01); *C12N 15/111* (2013.01); *C12N 15/113* (2013.01); *C12N 15/1137* (2013.01); *A61K 9/127* (2013.01); *C12N 2310/14* (2013.01); *C12N 2310/3515* (2013.01); *C12N 2310/531* (2013.01); *C12N 2320/32* (2013.01)

(58) Field of Classification Search
CPC .......................... C12N 15/113; C12N 2310/14
See application file for complete search history.

(56) References Cited

U.S. PATENT DOCUMENTS

| 3,791,932 A | 2/1974 | Schuurs |
| 3,839,153 A | 10/1974 | Schuurs |
| 3,850,578 A | 11/1974 | McConnell |
| 3,850,752 A | 11/1974 | Schuurs |
| 3,853,987 A | 12/1974 | Dreyer |
| 3,867,517 A | 2/1975 | Ling |
| 3,879,262 A | 4/1975 | Schuurs |
| 3,901,654 A | 8/1975 | Gross |
| 3,935,074 A | 1/1976 | Rubenstein |
| 3,984,533 A | 10/1976 | Uzgiris |
| 3,996,345 A | 12/1976 | Ullman |
| 4,034,074 A | 7/1977 | Miles |
| 4,098,876 A | 7/1978 | Piasio |
| 4,666,828 A | 5/1987 | Gusella |
| 4,683,202 A | 7/1987 | Mullis |
| 4,801,531 A | 1/1989 | Frossard |
| 4,879,219 A | 11/1989 | Wands |
| 5,011,771 A | 4/1991 | Bellet |
| 5,192,659 A | 3/1993 | Simons |
| 5,272,057 A | 12/1993 | Smulson |
| 5,281,521 A | 1/1994 | Trojanowski |
| 5,486,359 A | 1/1996 | Caplan |
| 5,721,138 A | 2/1998 | Lawn |

(Continued)

FOREIGN PATENT DOCUMENTS

| EP | 0375408 A1 | 6/1990 |
| EP | 2254586 B1 | 4/2015 |

(Continued)

OTHER PUBLICATIONS

Elbashir et al. (The EMBO Journal, vol. 20, No. 23, pp. 6877-6888, 2001).*
Zhang et al. (Trends in Molecular Medicine, 2015, 21,9, 543-548).*
Ahuja et al., (2017) Traumatic Spinal Cord Injury-Repair and Regeneration. Neurosurgery 80(3S): S9-S22.
Alvarez-Erviti et al., (2011) Delivery of siRNA to the mouse brain by systemic injection of targeted exosomes. Nat Biotechnol 29(4): 341-345.
Andersson et al., (2000) Large-scale synthesis of peptides. Biopolymers 55(3): 227-250.

(Continued)

*Primary Examiner* — Amy H Bowman
(74) *Attorney, Agent, or Firm* — Raphael Bellum PLLC

(57) ABSTRACT

The present invention provides pharmaceutical compositions comprising membrane vesicles, including extracellular vesicles including those referred to as exosomes, loaded with an exogenous Phosphatase and tensin homolog (PTEN) inhibitor. Methods of treating neurological diseases, disorders or conditions using the extracellular vesicles are provided. Isolated extracellular vesicles loaded with an exogenous Phosphatase and tensin homolog (PTEN) inhibitor are provided as well.

8 Claims, 10 Drawing Sheets
Specification includes a Sequence Listing.

(56) References Cited

U.S. PATENT DOCUMENTS

| | | |
|---|---|---|
| 9,017,981 B2 | 4/2015 | Parsons |
| 9,080,171 B2 | 7/2015 | Khvorova |
| 10,240,149 B2 | 3/2019 | Khvorova |
| 10,513,710 B2 | 12/2019 | Khvorova |
| 2002/0123476 A1 | 9/2002 | Emanuele |
| 2002/0128218 A1 | 9/2002 | Emanuele |
| 2003/0096980 A1 | 5/2003 | Froehler |
| 2003/0170680 A1 | 9/2003 | Froehler |
| 2004/0180351 A1 | 9/2004 | Giese |
| 2005/0043263 A1 | 2/2005 | Giese |
| 2007/0297985 A1 | 12/2007 | Williams |
| 2010/0166747 A1 | 7/2010 | Beltran |
| 2010/0291681 A1* | 11/2010 | Khvorova ...... C12Y 502/01008 707/769 |
| 2011/0213013 A1 | 9/2011 | Mcmanus |
| 2011/0294870 A1 | 12/2011 | Collard |
| 2013/0079382 A1 | 3/2013 | Smith |
| 2013/0171177 A1 | 7/2013 | Corteling |
| 2015/0079046 A1 | 3/2015 | Sinden |
| 2016/0074472 A1 | 3/2016 | Wang |
| 2016/0311857 A1 | 10/2016 | Li |
| 2017/0247708 A1 | 8/2017 | Katakowski |
| 2018/0177727 A1* | 6/2018 | Kalluri ............... A23C 19/0904 |

FOREIGN PATENT DOCUMENTS

| | | | | |
|---|---|---|---|---|
| EP | 2949752 B1 | 12/2017 | | |
| EP | 3132044 B1 | 4/2020 | | |
| KR | 2016141677 | * 12/2016 | ........... | C12N 15/113 |
| WO | 2009117387 A2 | 9/2009 | | |
| WO | 2011044701 A1 | 4/2011 | | |
| WO | 2011088058 A1 | 7/2011 | | |
| WO | WO 2011/088058 A1 * | 7/2011 | ........... | C12N 15/113 |
| WO | 2011119852 A1 | 9/2011 | | |
| WO | 2013150303 A1 | 10/2013 | | |
| WO | WO 2013/150303 A1 * | 10/2013 | ........... | C12N 15/111 |
| WO | 2013186735 A2 | 12/2013 | | |
| WO | 2014152622 A1 | 9/2014 | | |
| WO | 2015066701 A1 | 5/2015 | | |
| WO | 2015105957 A1 | 7/2015 | | |
| WO | 2015161184 A1 | 10/2015 | | |
| WO | 2017161010 A1 | 9/2017 | | |
| WO | 2017173034 A1 | 10/2017 | | |
| WO | 2017176894 A1 | 10/2017 | | |
| WO | 2017199250 A1 | 11/2017 | | |
| WO | 2018011153 A1 | 1/2018 | | |
| WO | 2018022927 A1 | 2/2018 | | |
| WO | 2018033911 A1 | 2/2018 | | |
| WO | 2018083700 A1 | 5/2018 | | |
| WO | 2019016799 A1 | 1/2019 | | |

OTHER PUBLICATIONS

Anwar et al., (2016) Inflammogenesis of Secondary Spinal Cord Injury. Front Cell Neurosci 10: 98; 24 pages.

Baglio et al., (2015) Human bone marrow- and adipose-mesenchymal stem cells secrete exosomes enriched in distinctive miRNA and tRNA species. Stem Cell Res Ther 6(1): 127; 20 pages.

Basser et al., (2000) In vivo fiber fractography using DT-MRI data. Magn Reson Med 44(4): 625-632.

Basso et al., (1995) A sensitive and reliable locomotor rating scale for open field testing in rats. J Neurotrauma 12(1): 1-21. Abstract.

Besch Ret al, (2002) Specific inhibition of ICAM-1 expression mediated by gene targeting with Triplex-forming oligonucleotides. J Biol Chem 277(36): 32473-32479.

Betzer et al., (2015) In-vitro Optimization of Nanoparticle-Cell Labeling Protocols for In-vivo Cell Tracking Applications. Sci Rep 5: 15400; 11 pages.

Betzer et al., (2017) In Vivo Neuroimaging of Exosomes Using Gold Nanoparticles. ACS Nano 11(11): 10883-10893.

Betzer et al., (2017) The effect of nanoparticle size on the ability to cross the blood-brain barrier: an in vivo study. Nanomedicine (Lond) 12(13): 1533-1546. Abstract.

Bhargava et al., (2004) Long double-stranded RNA-mediated RNA interference as a tool to achieve site-specific silencing of hypothalamic neuropeptides. Brain Res Brain Res Protoc 13(2): 115-125.

Billy et al., (2001) Specific interference with gene expression induced by long, double-stranded RNA in mouse embryonal teratocarcinoma cell lines. Proc Natl Acad Sci U S A 98(25): 14428 14433.

Boudreau et al., (2011) RNAi medicine for the brain: progresses and challenges. Hum Mol Genet 20(R1): R21-R27.

Brummelkamp et al., (2002) A system for stable expression of short interfering RNAs in mammalian cells. Science 296 (5567): 550-553.

Bumcrot et al., (2006) RNAi therapeutics: a potential new class of pharmaceutical drugs. Nat Chem Biol 2(12): 711-719.

Carbone et al., (2003) Selective inhibition of transcription of the Ets2 gene in prostate cancer cells by a triplex-forming oligonucleotide. Nucleic Acids Res 31(3): 833-843.

Castanotto et al., (2002) Functional siRNA expression from transfected PCR products. RNA 8(11): 1454-1460.

Colter et al., (2000) Rapid expansion of recycling stem cells in cultures of plastic-adherent cells from human bone marrow. Proc Natl Acad Sci U S A 97(7): 3213-3218.

Cooney et al., (1988) Site-specific oligonucleotide binding represses transcription of the human c-myc gene in vitro. Science 241(4864): 456-459.

Cregg et al., (2014) Functional regeneration beyond the glial scar. Exp Neurol. Author manuscript; available in PMC Mar. 1, 2015. Published in final edited form as: Exp Neurol. Mar. 2014; 253: 197-207.

Crowe et al., (2018) Mechanism of intranasal drug delivery directly to the brain. Life Sci 195: 44-52.

De Becker and Riet (2016) Homing and migration of mesenchymal stromal cells: How to improve the efficacy of cell therapy? World J Stem Cells 8(3): 73-87.

Deleavey and Damha (2012) Designing chemically modified oligonucleotides for targeted gene silencing. Chem Biol 19 (8): 937-954.

Demidov et al., (1994) Stability of peptide nucleic acids in human serum and cellular extracts. Biochem Pharmacol 48 (6): 1310-1313 Abstract.

Diallo et al., (2003) Long endogenous dsRNAs can induce complete gene silencing in mammalian cells and primary cultures. Oligonucleotides 13(5): 381-392.

Didiot et al., (2016) Exosome-mediated Delivery of Hydrophobically Modified siRNA for Huntingtin mRNA Silencing. Mol Ther 24(10): 1836-1847.

Dobrovolskaia (2015) Pre-clinical immunotoxicity studies of nanotechnology-formulated drugs: Challenges, considerations and strategy. J Control Release. Author manuscript; available in PMC Dec. 28, 2016. Published in final edited form as: J Control Release. Dec. 28, 2015; 220(0 0): 571-583.

Dobrovolskaia et al., (2016) Current understanding of interactions between nanoparticles and the immune system. Toxicol Appl Pharmacol. Author manuscript; available in PMC May 15, 2017. Published in final edited form as: Toxicol Appl Pharmacol. May 15, 2016; 299: 78-89.

Eckstein (2002) Developments in RNA chemistry, a personal view. Biochimie 84(9): 841-848. Abstract.

Ferguson et al., (2018) The microRNA regulatory landscape of MSC-derived exosomes: a systems view. Sci Rep 8(1): 1419; 12 pages.

Frisk et al., (2002) Silencing of the PTEN tumor-suppressor gene in anaplastic thyroid cancer. Genes Chromosomes Cancer 35(1): 74-80. Abstract.

Gao et al., (2013) Mesenchymal stem cells: a potential targeted-delivery vehicle for anti-cancer drug, loaded nanoparticles. Nanomedicine 9(2): 174-184. Abstract.

García-Alías et al., (2009) Chondroitinase ABC treatment opens a window of opportunity for task-specific rehabilitation. Nat Neurosci 12(9): 1145-1151. Abstract.

Goldberg (2004) Intrinsic neuronal regulation of axon and dendrite growth. Curr Opin Neurobiol 14(5): 551-557. Abstract.

(56) References Cited

OTHER PUBLICATIONS

Gong et al., (2017) Mesenchymal stem cells release exosomes that transfer miRNAs to endothelial cells and promote angiogenesis. Oncotarget 8(28): 45200-45212.
Grishok et al., (2011) Genes and mechanisms related to RNA interference regulate expression of the small temporal RNAs that control C. elegans developmental timing. Cell 106(1): 23-34.
Guo et al., (2005) MicroRNA directs mRNA cleavage of the transcription factor NAC1 to downregulate auxin signals for *Arabidopsis* lateral root development Plant Cell 17(5): 1376-1386.
Guo et al., Intranasal administration of mesenchymal stem-cells derived exosomes loaded with PTEN siRNA enables functional recovery in rats after complete spinal cord injury. Abstract presented at the Nano.IL.2018, Oct. 9-11, 2018, Jerusalem, Israel.
Guo et al., Intranasal administration of mesenchymal stem-cells derived exosomes loaded with PTEN siRNA enables functional recovery in rats after complete spinal cord injury. Poster presented at the Nano.IL.2018, Oct. 9-11, 2018, Jerusalem, Israel.
Ha et al., (2016) Exosomes as therapeutic drug carriers and delivery vehicles across biological membranes: current perspectives and future challenges Acta Pharm Sin B 6(4): 287-296.
Hammond et al., (2001) Argonaute2, a link between genetic and biochemical analyses of RNAi. Science 293(5532): 1146-1150.
Haney et al., (2015) Exosomes as drug delivery vehicles for Parkinson's disease therapy. J Control Release. Author manuscript; available in PMC Jun. 10, 2016. Published in final edited form as: J Control Release. Jun. 10, 2015; 207: 18-30.
Haraszti et al., (2016) High-resolution proteomic and lipidomic analysis of exosomes and microvesicles from different cell sources. J Extracell Vesicles 5: 32570; 15 pages.
Hiebert et al., (2002) Brain-derived neurotrophic factor applied to the motor cortex promotes sprouting of corticospinal fibers but not regeneration into a peripheral nerve transplant. J Neurosci Res 69(2): 160-168 Abstract.
Hutvágner and Zamore (2002) A microRNA in a multiple-turnover RNAi enzyme complex. Science 297(5589): 2056-2060.
Hutvágner et al., (2001) A cellular function for the RNA-interference enzyme Dicer in the maturation of the let-7 small temporal RNA. Science 293(5531): 834-838.
James et al., (2015) Chondroitinase gene therapy improves upper limb function following cervical contusion injury. Exp Neurol 271: 131-135.
Jones et al., (2002) Isolation and characterization of bone marrow multipotential mesenchymal progenitor cells. Arthritis Rheum 46(12): 3349-3360.
Ketting et al., (2001) Dicer functions in RNA interference and in synthesis of small RNA involved in developmental timing in C. elegans. Genes Dev 15(20): 2654-2659.
Cheng et al., (2018) Mesenchymal stem cells deliver exogenous miR-21 via exosomes to inhibit nucleus pulposus cell apoptosis and reduce intervertebral disc degeneration. J Cell Mol Med 22(1): 261-276.
Li et al., (2016) Human aortic smooth muscle cell-derived exosomal miR-221/222 inhibits autophagy via a PTEN/Akt signaling pathway in human umbilical vein endothelial cells. Biochem Biophys Res Commun 479(2): 343-350.
Santel et al., (2006) RNA interference in the mouse vascular endothelium by systemic administration of siRNA-lipoplexes for cancer therapy. Gene Ther 13(18): 1360-1370.
Kim et al., (2012) Proteomic analysis of microvesicles derived from human mesenchymal stem cells. J Proteome Res 11(2): 839-849 Abstract.
Kourembanas (2015) Exosomes: vehicles of intercellular signaling, biomarkers, and vectors of cell therapy. Annu Rev Physiol 77: 13-27. Abstract.
Lachyankar et al., (2000) A role for nuclear PTEN in neuronal differentiation. J Neurosci 20(4): 1404-1413.
Lee et al., (1993) The C. elegans heterochronic gene lin-4 encodes small RNAs with antisense complementarity to lin-14. Cell 75(5): 843-854.
Lee et al., (2012) Delayed applications of L1 and chondroitinase ABC promote recovery after spinal cord injury. J Neurotrauma 29(10): 1850-1863.
Leemans et al., (2009) ExploreDTI: a graphical toolbox for processing, analyzing, and visualizing diffusion MR data. Proc Intl Soc Mag Reson Med 17: 3536.
Li et al., (2015) Silencing of PMEPA1 accelerates the growth of prostate cancer cells through AR, NEDD4 and PTEN. Oncotarget 6(17): 15137-15149.
Little et al., (2015) PTEN depletion decreases disease severity and modestly prolongs survival in a mouse model of spinal muscular atrophy. Mol Ther 23(2): 270-277.
Liu et al., (2010) PTEN deletion enhances the regenerative ability of adult corticospinal neurons. Nat Neurosci 13(9): 1075-1081.
Liu et al., (2019) Exosomes Derived from Bone Mesenchymal Stem Cells Repair Traumatic Spinal Cord Injury by Suppressing the Activation of A1 Neurotoxic Reactive Astrocytes. J Neurotrauma 36(3): 469-484.
Locht et al., (2011) The ins and outs of pertussis toxin. FEBS J 278(23): 4668-4682.
Long et al., (2017) Intranasal MSC-derived A1-exosomes ease inflammation, and prevent abnormal neurogenesis and memory dysfunction after status epilepticus. Proc Natl Acad Sci U S A 114(17): E3536-E3545.
Ly et al., (2017) Visualization of self-delivering hydrophobically modified siRNA cellular internalization. Nucleic Acids Res 45(1): 15-25.
Maher et al., (1989) Inhibition of DNA binding proteins by oligo-nucleotide-directed triple helix formation. Science 245 (4919): 725-730.
Marcus and Leonard (2013) FedExosomes: Engineering Therapeutic Biological Nanoparticles that Truly Deliver. Pharmaceuticals (Basel) 6(5): 659-680.
Marote et al., (2016) MSCs-Derived Exosomes: Cell-Secreted Nanovesicles with Regenerative Potential. Front Pharmacol 7: 231; 8 pages.
McCall et al., (2012) Neurotrophic factors in combinatorial approaches for spinal cord regeneration. Cell Tissue Res. Author manuscript; available in PMC Jul. 1, 2013. Published in final edited form as: Cell Tissue Res. Jul. 2012; 349(1): 27-37.
Merkus et al., (1998) Nasal mucociliary clearance as a factor in nasal drug delivery. Adv Drug Deliv Rev 29(1-2): 13-38 Abstract.
Moser and Dervan (1987) Sequence-specific cleavage of double helical DNA by triple helix formation. Science 238 (4827): 645-650.
Moser and Dervan (1991) Second structural motif for recognition of DNA by oligonucleotide-directed triple-helix formation. Science 251(4999): 1360-1363. Abstract.
Mourelatos et al., (2002) miRNPs: a novel class of ribonucleoproteins containing numerous microRNAs. Genes Dev 16 (6): 720-728.
M'Dahoma et al., (2014) Spinal cord transection-induced allodynia in rats—behavioral, physiopathological and pharmacological characterization. PLoS One 9(7): e102027; 15 pages.
Nielsen et al., (1991) Sequence-selective recognition of DNA by strand displacement with a thymine-substituted polyamide. Science 254(5037): 1497-1500.
Ning et al., (2010) PTEN depletion rescues axonal growth defect and improves survival in SMN-deficient motor neurons. Hum Mol Genet 19(16): 3159-3168.
Niu et al., (2016) PTEN Activation by DNA Damage Induces Protective Autophagy in Response to Cucurbitacin B in Hepatocellular Carcinoma Cells. Oxid Med Cell Longev 2016: 4313204; 16 pages.
Otero-Ortega et al., (2018) Exosomes promote restoration after an experimental animal model of intracerebral hemorrhage. J Cereb Blood Flow Metab 38(5): 767-779.
Paddison et al., (2002) Stable suppression of gene expression by RNAi in mammalian cells. Proc Natl Acad Sci U S A 99(3): 1443-1448.
Parizotto et al., (2004) In vivo investigation of the transcription, processing, endonucleolytic activity, and functional relevance of the spatial distribution of a plant miRNA. Genes Dev 18(18): 2237-2242.

(56) References Cited

OTHER PUBLICATIONS

Park et al., (2008) Promoting axon regeneration in the adult CNS by modulation of the PTEN/mTOR pathway. Science 322(5903): 963-966.
Perets et al., (2018) Intranasal administration of exosomes derived from mesenchymal stem cells ameliorates autistic-like behaviors of BTBR mice. Mol Autism 9: 57; 12 pages.
Povysheva et al., (2018) PTEN expression in astrocytic processes after spinal cord injury. Mol Cell Neurosci 88: 231-239.
Pulido (2018) PTEN Inhibition in Human Disease Therapy. Molecules 23(2): 285; 25 pages.
Puri et al., (2001) Targeted gene knockout by 2'-O-aminoethyl modified triplex forming oligonucleotides. J Biol Chem 276(31): 28991-28998.
Ramachandran et al., (2013) Recent advances in RNA interference therapeutics for CNS diseases. Neurotherapeutics 10(3): 473-485.
Raposo and Stoorvogel (2013) Extracellular vesicles: exosomes, microvesicles, and friends. J Cell Biol 200(4): 373-383.
Rauch et al., (2009) Engineering angiogenesis following spinal cord injury: a coculture of neural progenitor and endothelial cells in a degradable polymer implant leads to an increase in vessel density and formation of the blood-spinal cord barrier. Eur J Neurosci. Author manuscript; available in PMC Jan. 1, 2010. Published in final edited form as: Eur J Neurosci. Jan. 2009; 29(1): 132-145.
Reither and Jeltsch (2002) Specificity of DNA triple helix formation analyzed by a FRET assay. BMC Biochem 3:27; 9 pages.
Rocha et al., (2018) The Role of Biomaterials as Angiogenic Modulators of Spinal Cord Injury: Mimetics of the Spinal Cord, Cell and Angiogenic Factor Delivery Agents. Front Pharmacol 9: 164; 7 pages.
Rungta et al., (2013) Lipid Nanoparticle Delivery of siRNA to Silence Neuronal Gene Expression in the Brain. Mol Ther Nucleic Acids 2(12): e136; 12 pages.
Salem and Thiemermann (2010) Mesenchymal stromal cells: current understanding and clinical status. Stem Cells 28 (3): 585-596.
Sanghvi (2011) A status update of modified oligonucleotides for chemotherapeutics applications. Curr Protoc Nucleic Acid Chem Chapter 4: Unit 4.1.1-22. Abstract.
Segal-Gavish et al., (2016) Mesenchymal Stem Cell Transplantation Promotes Neurogenesis and Ameliorates Autism Related Behaviors in BTBR Mice. Autism Res 9(1): 17-32.
Seidman and Glazer (2003) The potential for gene repair via triple helix formation. J Clin Invest 112(4): 487-494.
Shinagawa and Ishii (2003) Generation of Ski-knockdown mice by expressing a long double-strand RNA from an RNA polymerase II promoter. Genes Dev 17(11): 1340-1345.
Singh et al., (2014) Regeneration of diabetic axons is enhanced by selective knockdown of the PTEN gene. Brain 137 (Pt 4): 1051-1067.
Strat et al., (2006) Specific and nontoxic silencing in mammalian cells with expressed long dsRNAs. Nucleic Acids Res 34(13): 3803-3810.
Théry et al., (2006) Isolation and characterization of exosomes from cell culture supernatants and biological fluids. Curr Protoc Cell Biol Chapter 3: Unit 3.22. 29 pages.
Tran et al., (2004) Control of specific gene expression in mammalian cells by co-expression of long complementary RNAs. FEBS Lett 573(1-3): 127-134.
Uccelli et al., (2011) Mesenchymal stem cells for the treatment of multiple sclerosis and other neurological diseases. Lancet Neurol 10(7): 649-656.
Vasquez et al., (1999) Chromosomal mutations induced by triplex-forming oligonucleotides in mammalian cells. Nucleic Acids Res 27(4): 1176-1181.
Vuyisich and Beal (2000) Regulation of the RNA-dependent protein kinase by triple helix formation. Nucleic Acids Res 28(12): 2369-2374.
Welch et al., (1998) Expression of ribozymes in gene transfer systems to modulate target RNA levels. Curr Opin Biotechnol 9(5): 486-496.
Welch et al., (1998) Ribozyme gene therapy for hepatitis C virus infection. Clin Diagn Virol 10(2-3): 163-171.
Wightman et al., (1993) Posttranscriptional regulation of the heterochronic gene lin-14 by lin-4 mediates temporal pattern formation in C. elegans. Cell 75(5): 855-862.
Williams and Rubin (2002) ARGONAUTE1 is required for efficient RNA interference in *Drosophila* embryos. Proc Natl Acad Sci U S A 99(10): 6889-6894.
Williams et al., (2015) Permissive Schwann cell graft/spinal cord interfaces for axon regeneration. Cell Transplant 24 (1): 115-131.
Xin et al., (2012) Exosome-mediated transfer of miR-133b from multipotent mesenchymal stromal cells to neural cells contributes to neurite outgrowth. Stem Cells 30(7): 1556-1564.
Yiu and He (2006) Glial inhibition of CNS axon regeneration. Nat Rev Neurosci 7(8): 617-627.
Yu et al., (2016) Angiogenic microspheres promote neural regeneration and motor function recovery after spinal cord injury in rats. Sci Rep 6: 33428; 13 pages.
Zeng et al., (2002) Both natural and designed micro RNAs can inhibit the expression of cognate mRNAs when expressed in human cells. Mol Cell 9(6): 1327-1333.
Zhang et al., (2015) Effect of exosomes derived from multipluripotent mesenchymal stromal cells on functional recovery and neurovascular plasticity in rats after traumatic brain injury. J Neurosurg 122(4): 856-867.
Zhang et al., (2015) Microenvironment-induced PTEN loss by exosomal microRNA primes brain metastasis outgrowth. Nature 527(7576): 100-104.
Zhang et al., (2017) Systemic administration of cell-free exosomes generated by human bone marrow derived mesenchymal stem cells cultured under 2D and 3D conditions improves functional recovery in rats after traumatic brain injury. Neurochem Int. Author manuscript; available in PMC Dec. 1, 2018. Published in final edited form as: Neurochem Int. Dec. 2017; 111: 69-81.
Zhuang et al., (2011) Treatment of brain inflammatory diseases by delivering exosome encapsulated anti-inflammatory drugs from the nasal region to the brain. Mol Ther 19(10): 1769-1779.
Anderson et al., (2018) Required growth facilitators propel axon regeneration across complete spinal cord injury. Nature 561(7723): 396-400.
Devaux et al., (2017) RhoA Inhibitor Treatment At Acute Phase of Spinal Cord Injury May Induce Neurite Outgrowth and Synaptogenesis. Mol Cell Proteomics 16(8): 1394-1415.
Tamkovich et al., (2016) Exosomes: Generation, Structure, Transport, Biological Activity, and Diagnostic Application. Biologicheskie Membrany 33(3): 163-175. English abstract on p. 175, Only English abstract has been considered.
Yáñez-Mó et al., (2015) Biological properties of extracellular vesicles and their physiological functions. J Extracell Vesicles 4: 27066.

\* cited by examiner

SEQUENCE LISTING

<160> NUMBER OF SEQ ID NOS: 11

<210> SEQ ID NO 1
<211> LENGTH: 403
<212> TYPE: PRT
<213> ORGANISM: Homo sapiens

<400> SEQUENCE: 1

Met Thr Ala Ile Ile Lys Glu Ile Val Ser Arg Asn Lys Arg Arg Tyr
1               5                   10                  15

Gln Glu Asp Gly Phe Asp Leu Asp Leu Thr Tyr Ile Tyr Pro Asn Ile
            20                  25                  30

Ile Ala Met Gly Phe Pro Ala Glu Arg Leu Glu Gly Val Tyr Arg Asn
        35                  40                  45

Asn Ile Asp Asp Val Val Arg Phe Leu Asp Ser Lys His Lys Asn His
    50                  55                  60

Tyr Lys Ile Tyr Asn Leu Cys Ala Glu Arg His Tyr Asp Thr Ala Lys
65                  70                  75                  80

Phe Asn Cys Arg Val Ala Gln Tyr Pro Phe Glu Asp His Asn Pro Pro
                85                  90                  95

Gln Leu Glu Leu Ile Lys Pro Phe Cys Glu Asp Leu Asp Gln Trp Leu
            100                 105                 110

Ser Glu Asp Asp Asn His Val Ala Ala Ile His Cys Lys Ala Gly Lys
        115                 120                 125

Gly Arg Thr Gly Val Met Ile Cys Ala Tyr Leu Leu His Arg Gly Lys
    130                 135                 140

Phe Leu Lys Ala Gln Glu Ala Leu Asp Phe Tyr Gly Glu Val Arg Thr
145                 150                 155                 160

Arg Asp Lys Lys Gly Val Thr Ile Pro Ser Gln Arg Arg Tyr Val Tyr
                165                 170                 175

Tyr Tyr Ser Tyr Leu Leu Lys Asn His Leu Asp Tyr Arg Pro Val Ala
            180                 185                 190

Leu Leu Phe His Lys Met Met Glu Glu Thr Ile Pro Met Phe Ser Gly
        195                 200                 205

Gly Thr Cys Asn Pro Gln Phe Val Val Cys Gln Leu Lys Val Lys Ile
    210                 215                 220

Tyr Ser Ser Asn Ser Gly Pro Thr Arg Arg Glu Asp Lys Phe Met Tyr
225                 230                 235                 240

Phe Glu Phe Pro Gln Pro Leu Pro Val Cys Gly Asp Ile Lys Val Glu
                245                 250                 255

Phe Phe His Lys Gln Asn Lys Met Leu Lys Lys Asp Lys Met Phe His
            260                 265                 270

Phe Trp Val Asn Thr Phe Phe Ile Pro Gly Pro Glu Glu Thr Ser Glu
        275                 280                 285

Lys Val Glu Asn Gly Ser Leu Cys Asp Gln Glu Ile Asp Ser Ile Cys
    290                 295                 300

Ser Ile Glu Arg Ala Asp Asn Asp Lys Glu Tyr Leu Val Leu Thr Leu
305                 310                 315                 320

Thr Lys Asn Asp Leu Asp Lys Ala Asn Lys Asp Lys Ala Asn Arg Tyr
                325                 330                 335

Phe Ser Pro Asn Phe Lys Val Lys Leu Tyr Phe Thr Lys Thr Val Glu
            340                 345                 350

Glu Pro Ser Asn Pro Glu Ala Ser Ser Ser Thr Ser Val Thr Pro Asp
        355                 360                 365

```
Val Ser Asp Asn Glu Pro Asp His Tyr Arg Tyr Ser Asp Thr Thr Asp
    370                 375                 380

Ser Asp Pro Glu Asn Glu Pro Phe Asp Glu Asp Gln His Thr Gln Ile
385                 390                 395                 400

Thr Lys Val

<210> SEQ ID NO 2
<211> LENGTH: 27
<212> TYPE: RNA
<213> ORGANISM: Artificial sequence
<220> FEATURE:
<223> OTHER INFORMATION: Exemplary siRNA sequences that are contemplated
      for inhibition of PTEN

<400> SEQUENCE: 2
guuagcagaa acaaaaggag auaucaa                                              27

<210> SEQ ID NO 3
<211> LENGTH: 27
<212> TYPE: RNA
<213> ORGANISM: Artificial sequence
<220> FEATURE:
<223> OTHER INFORMATION: Exemplary siRNA sequences that are contemplated
      for inhibition of PTEN

<400> SEQUENCE: 3
uugauaucuc cuuuuguuuc ugcuaac                                              27

<210> SEQ ID NO 4
<211> LENGTH: 27
<212> TYPE: DNA
<213> ORGANISM: Artificial sequence
<220> FEATURE:
<223> OTHER INFORMATION: Exemplary siRNA sequences that are contemplated
      for inhibition of PTEN

<400> SEQUENCE: 4
cagccguucg gaggauuauu cgucutt                                              27

<210> SEQ ID NO 5
<211> LENGTH: 27
<212> TYPE: DNA
<213> ORGANISM: Artificial sequence
<220> FEATURE:
<223> OTHER INFORMATION: Exemplary siRNA sequences that are contemplated
      for inhibition of PTEN

<400> SEQUENCE: 5
agacgaauaa uccuccgaac ggcugtt                                              27

<210> SEQ ID NO 6
<211> LENGTH: 20
<212> TYPE: DNA
<213> ORGANISM: Artificial sequence
<220> FEATURE:
<223> OTHER INFORMATION: Exemplary sequence to which the PTEN siRNA may
      be targeted

<400> SEQUENCE: 6
gagttcttcc acaaacagaa                                                      20

<210> SEQ ID NO 7
<211> LENGTH: 19
<212> TYPE: DNA
<213> ORGANISM: Artificial sequence
<220> FEATURE:
```

```
<223> OTHER INFORMATION: Exemplary sequence to which the PTEN siRNA may
      be targeted

<400> SEQUENCE: 7
gtatagagcg tgcagataa                                                      19

<210> SEQ ID NO 8
<211> LENGTH: 10
<212> TYPE: RNA
<213> ORGANISM: Artificial sequence
<220> FEATURE:
<223> OTHER INFORMATION: Examples of oligonucleotide sequences that can
      be used to form the loop
<220> FEATURE:
<221> NAME/KEY: n
<222> LOCATION: (10)..(10)
<223> OTHER INFORMATION: n=a, u, t, c, g or absent
<220> FEATURE:
<221> NAME/KEY: misc_feature
<222> LOCATION: (10)..(10)
<223> OTHER INFORMATION: n is a, c, g, or u

<400> SEQUENCE: 8 uucaagagan                                                                10

<210> SEQ ID NO 9
<211> LENGTH: 10
<212> TYPE: RNA
<213> ORGANISM: Artificial sequence
<220> FEATURE:
<223> OTHER INFORMATION: Examples of oligonucleotide sequences that can
      be used to form the loop
<220> FEATURE:
<221> NAME/KEY: n
<222> LOCATION: (10)..(10)
<223> OTHER INFORMATION: n=a, u, t, c, g or absent
<220> FEATURE:
<221> NAME/KEY: misc_feature
<222> LOCATION: (10)..(10)
<223> OTHER INFORMATION: n is a, c, g, or u

<400> SEQUENCE: 9 uuuguguagn                                                                10

<210> SEQ ID NO 10
<211> LENGTH: 20
<212> TYPE: DNA
<213> ORGANISM: Artificial Sequence
<220> FEATURE:
<223> OTHER INFORMATION: Synthesized

<400> SEQUENCE: 10
gaguucuucc acaaacagaa                                                     20

<210> SEQ ID NO 11
<211> LENGTH: 20
<212> TYPE: DNA
<213> ORGANISM: Artificial Sequence
<220> FEATURE:
<223> OTHER INFORMATION: Synthesized

<400> SEQUENCE: 11
uucuguuugu ggaagaacuc                                                     20
```

VESICLES COMPRISING A PTEN INHIBITOR AND USES OF SAME

FIELD OF THE INVENTION

The present invention relates to membranous vesicles loaded with a PTEN inhibitor, pharmaceutical compositions comprising the vesicles, and their use in treatment of neurological disorders and, more particularly to cell-derived extracellular vesicles loaded with an exogenous PTEN inhibitor, pharmaceutical compositions comprising same and their use for the treatment of spinal cord injuries.

BACKGROUND OF THE INVENTION

Damage to the spinal cord may result in autonomic dysfunction, a loss of sensation or a loss of mobility. Such spinal cord injury (SCI) is caused by trauma, tumors, ischemia, developmental disorders, neurodegenerative diseases, demyelinative diseases, transverse myelitis, vascular malformations, or other causes. The consequences of SCI depend on the specific nature of the injury and its location along the spinal cord. In addition, because SCI is a dynamic process, the full extent of injury may not be apparent initially in all acute cord syndromes. Incomplete cord lesions may evolve into more complete lesions; more commonly, the injury level raises one or two spinal levels during the hours to days after the initial event. A complex cascade of pathophysiologic events accounts for this clinical deterioration.

The psychological and social impact of SCIs often is devastating. Some of the general disabling conditions associated with SCI are permanent paralysis of the limbs, chronic pain, muscular atrophy, loss of voluntary control over bladder and bowel, sexual dysfunction, and infertility.

Recent advances in neuroscience have drawn considerable attention to research into SCI and have made significantly better treatment and rehabilitation options available. Functional electrical stimulation (FES), for example, has shown the potential to enhance nerve regeneration and allow significant improvements in restoring and improving functional capacity after SCI. However, not all patients with spinal cord injury qualify for FES (a complete lesion of the spinal cord must be present); the patient must be in a neurologically stable condition; and the peripheral nerves must be intact to respond to exogenous electrical stimulations.

Axon regeneration following SCI is limited, due to intrinsic extremely limited ability of mature neurons to grow, and also extrinsic factors, such as glial scar maturing overtime and inhibitory molecules. Attempts have been made to modify extrinsic factors, yet success is limited. For example, extracellular inhibitory molecule removal, neurotrophic factor delivery, or permissive substrate grafting failed to elicit robust regeneration of injured corticospinal tract.

Phosphatase and tensin homolog (PTEN) is a highly conserved dual-specificity protein tyrosine phosphatase. The protein dephosphorylates the lipid second messengers phosphatidylinositol 3,4,5-trisphosphate [PI(3,4,5)P3] and phosphatidylinositol 3,4-bisphosphate [PI(3,4)P2] to produce phosphatidylinositol 4,5-bisphosphate [PI(4,5)P2] and phosphatidylinositol 4-phosphate [PI(4)P], respectively. This unique activity makes PTEN a major homeostatic regulator and tumor suppressor protein, which function is absent or defective in a wide variety of tumors as a result of somatic alterations. The important role of the PI3K/AKT/mTOR signaling pathway in cell growth, regeneration and survival supports the rationale for the therapeutic targeting of PTEN. Among the suggested PTEN inhibition-based therapeutic targets are nerve growth and regeneration after injury or damage, treatment of cardiac ischemia/reperfusion and associated disease, wound repair, and infertility (see review by Pulido, 2018, Molecules, 23, 285). Interestingly, the main paradigm of PTEN involvement in cancer is as a cancer suppressor, and it has been shown that PTEN inhibition may occur in brain metastases (Zhang et al., Nature, 2015, 527, 100-104).

PTEN is expressed preferentially in the neurons in adult brains, plays a critical role in controlling the regeneration of corticospinal neurons via downregulation of mammalian target of rapamycin (mTOR) activity. The mTOR activity is profoundly suppressed in axotomized adult neurons, limiting new protein synthesis required for sustained axon regeneration. Several publications mention involvement of PTEN in suppression of nerve regeneration and others showed the positive effect of PTEN depletion on conditions related to axon damage or impairment. Effective inhibition of PTEN would be a candidate for increasing mTOR thereby promoting nerve regeneration.

WO 2009/117389 describes the therapeutic use of inhibitors of PTEN to treat a neurodegenerative disorders. WO 2015/066701 describes a method of regeneration of nerve or attenuating degeneration of nerve by administering PTEN inhibiting peptide at or near the injured nerve. WO 2011/044701 describes particular PTEN inhibiting peptides and their use in treating diseases associated with cytotoxic stress including diseases and injuries of the central nervous system.

There is a vast number of vehicles suggested as useful for delivering siRNA molecules including liposomes, protein particles, micelles, and lipid particles among others. Rungta et al., (Molecular Therapy-Nucleic Acids, 2013, 2, e136) showed that siRNA in lipid nanoparticles (LNP) may efficiently silence neuronal genes expression.

Extracellular membrane vesicles (EVs) are membrane vesicles secreted by different types of cells. EVs are present in the blood circulation under normal physiological condition and their levels increased in a variety of diseases such as diabetes and related vascular complications, cardiovascular disease, hematologic malignancies as well as in solid tumors.

EVs can be divided into three subpopulations: (I) exosomes: having a diameter of 30-100 nm in and derived from endosomal compartments; (II) microvesicles: having a diameter of 100 nm-1 µm which are released from the cell surface via "vesiculation"; and (III) apoptotic bodies: having a diameter of 1-5 µm and which are released from apoptotic cells. EVs contain several elements of the parent cell including proteins, DNA fragments, micro RNAs and mRNA.

EP 2254586 is directed to exosomes isolated from mesenchymal stem cells, said exosomes comprising at least one biological property of a mesenchymal stem cell. In addition, exosomes were proposed as carriers for different drugs including small molecules and non-coding RNA (e.g. US 2017/0247708 and Ha et al., Acta Pharmaceutica Sinica B 2016; 6(4):287-296). Typically, siRNA is introduced into exosomes by electroporation.

WO2018/033911 to some of the inventors of the present application teaches mesenchymal stem cell derived exosomes for treatment of neurological disorders.

Neuronal damage in general and spinal cord injury (SCI) in particular involves a long and complex cascade of secondary events following the injury itself. The complexity of the cascade can affect the efficiency of the suggested treatments and there remains and unmet need for development of additional safe, efficient and convenient methods for treating SCI.

SUMMARY OF THE INVENTION

According to one aspect, the present invention provides a pharmaceutical composition comprising extracellular vesicles loaded with an exogenous phosphatase and tensin homolog (PTEN) inhibitor.

According to another aspect, the present invention provides a pharmaceutical composition comprising extracellular vesicles loaded with an exogenous phosphatase and tensin homolog (PTEN) inhibitor, for use in treating a neurological disease, disorder or condition.

According to a further aspect of the present invention there is provided a method of treating a neurological disease, disorder or condition in a subject in need thereof, comprising administering to the subject a therapeutically effective amount of membrane particles loaded with an exogenous Phosphatase and tensin homolog (PTEN) inhibitor, thereby treating the neurological disease or condition. According to some embodiments, the membrane particles are extracellular vesicles derived from cells.

According to yet another aspect, the present invention provides isolated extracellular vesicles loaded with an exogenous phosphatase and tensin homolog (PTEN) inhibitor.

According to any one of the above aspects, the extracellular vesicles are selected from the group consisting of exosomes, microvesicles, membrane particles, membrane vesicles, ectosomes and exovesicles. According to further features in the described embodiments, the particles comprise exosomes. According to some embodiments, the extracellular vesicles are a combination of exosomes and microvesicles. According to some embodiments, the extracellular vesicles, such as exosomes, are derived from adherent cells expressing mesenchymal markers. According to some embodiments, the adherent cells expressing mesenchymal markers are selected from mesenchymal stem cells, oral mucosa stem cells or olfactory ensheathing cells. According to other embodiments, the extracellular vesicles, such as exosomes, are derived from adherent cells expressing markers from neural crest cells. According to one embodiment, neural crest cells comprise cranial neural crest cells. According to further features in the described embodiments, the cranial neural crest cells are selected from the group consisting of dental pulp stem cells (DPSCs), exfoliated deciduous teeth stem cells (SHED), periodontal ligament stem cells (PDLSCs), apical papilla stem cells (SCAP) and dental follicle progenitor cells (DFPCs). According to any one of the above aspects and embodiments, the extracellular vesicles are isolated extracellular vesicles. According to some aspects and embodiments, the pharmaceutical composition of the present invention is a cell-free composition.

According to any one of the above aspects and embodiments, the PTEN inhibitor comprises a polynucleotide or oligonucleotide inhibitor of PTEN expression. According to some embodiments, the PTEN inhibitor is an RNA interference oligonucleotide. According to some embodiments, the RNA interference oligonucleotide is an siRNA directed towards PTEN. According to some embodiments, the siRNA comprises a sequence complementary to a nucleic acid encoding human PTEN protein. According to some embodiments, the oligonucleotide inhibitor comprises a hydrophobic moiety. According to certain embodiments, the hydrophobic moiety is a sterol, a ganglioside, a lipid, a vitamin, a fatty acid, a peptide, or a combination thereof. According to some embodiments, the hydrophobic moiety is a sterol. According to some embodiments, the sterol comprises cholesterol.

According to further features of any one of the described aspects or embodiments, the PTEN inhibitor comprises a peptide inhibitor.

According to some above aspects and embodiments, the neurological disease is a neurodegenerative disease. According to other aspects and embodiments, the neurological condition is a spinal cord injury. According to some above aspects and embodiments, treating spinal cord injury comprises administering the pharmaceutical composition or isolated extracellular vesicles to the subject in need thereof. According to some embodiments, administering comprises intranasal administration. According to some embodiments, treating further comprises administering to the subject a therapeutically effective amount of Chondroitinase ABC or a polynucleotide encoding same.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE FIGURES

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

FIG. 11 shows that intranasal ExoPTEN treatment induces locomotor, sensory and bladder recovery.

FIG. 12 shows measurement of MRI and electrophysiology parameters in the lesion area in treated and untreated rats.

DETAILED DESCRIPTION OF THE INVENTION

The present invention, in some embodiments thereof, relates to vesicles loaded with an exogenous PTEN inhibitor for treatment of neurological disorders and, more particularly, but not exclusively, to cell-derived vesicles loaded with PTEN inhibitor for the treatment of spinal cord injuries. Before explaining at least one embodiment of the invention in detail, it is to be understood that the invention is not necessarily limited in its application to the details set forth in the following description or exemplified by the Examples. The invention is capable of other embodiments or of being practiced or carried out in various ways.

Figure 2:
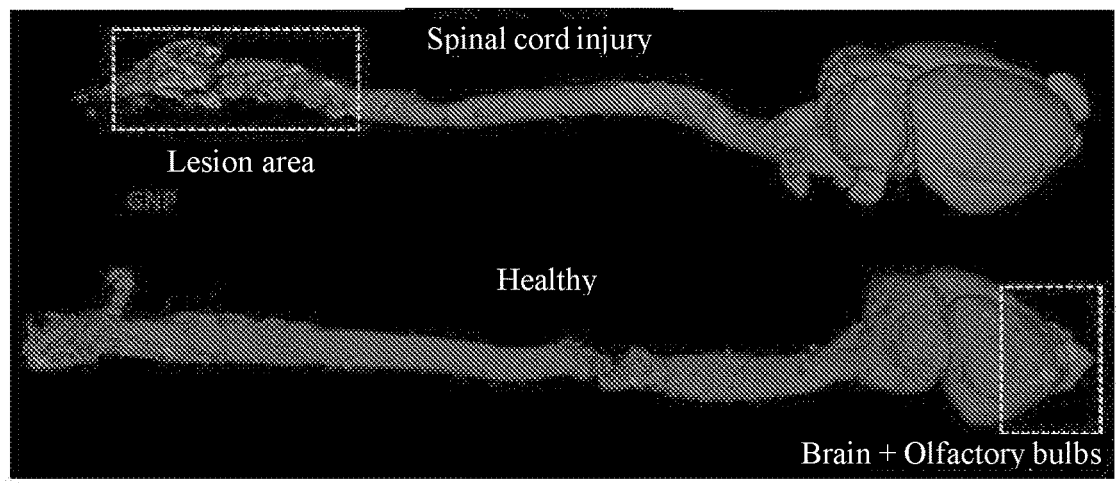
FIG. 2 shows micro-CT scanning of all the CNS tissues in the injured (upper panel) and healthy (lower panel) rats. The figure shows that exosomes cross the blood-brain-barrier, reach the spinal cord lesion.
Figure 6:
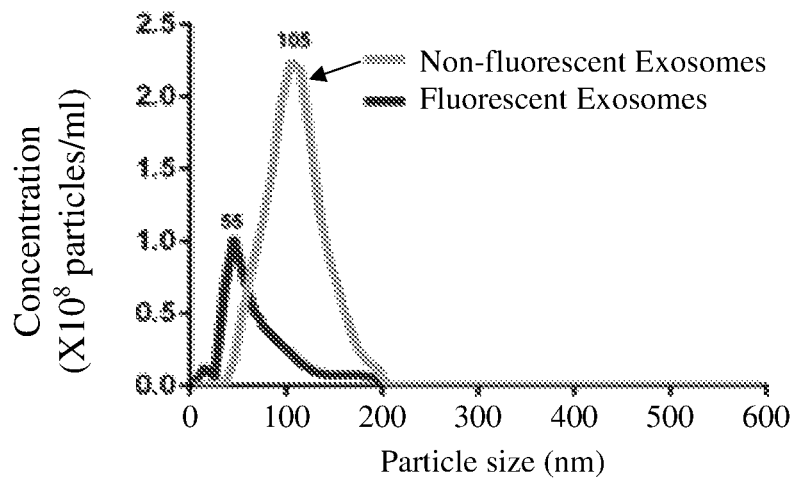
FIG. 6 shows NanoSight analysis of Cy3-tagged self-deliverable MAPK-siRNA incubated with exosomes. The figures shows size distribution of non-fluorescent exosomes (gray) and Cy3-exosomes (black).
Figure 7A:
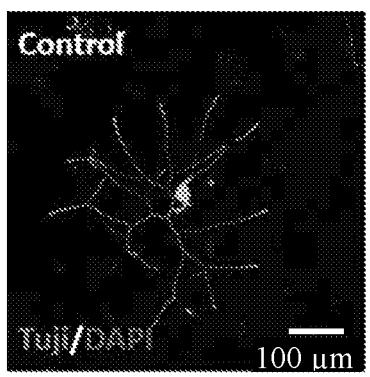
FIG. 7 shows a representative immunofluorescent staining images of dorsal root ganglia (DRG) neurons treated with: a control (medium) (FIG. 7A), non-targeting control siRNA (FIG. 7B), MSC-Exo (FIG. 7C), PTEN-siRNA (FIG. 7D) or ExoPTEN (FIG. 7E). Scale bar, 100 μm.
Figure 7B:
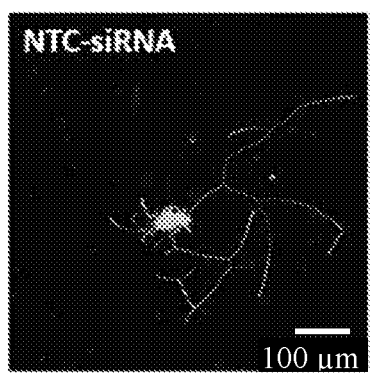
Figure 7C:
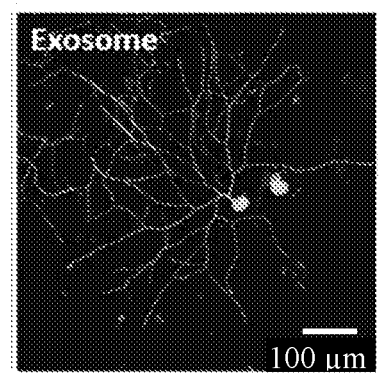
Figure 7D:
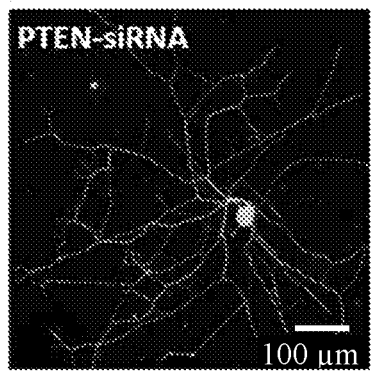
Figure 7E:
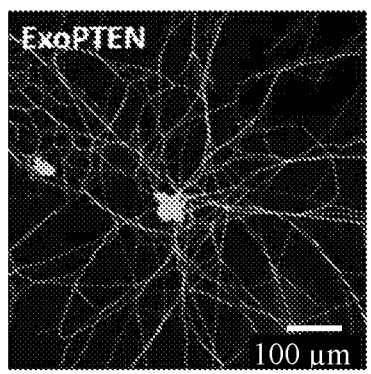

Specifically, the present inventors have demonstrated that exosomes may be efficiently loaded with cholesterol-conjugated siRNA (FIG. 6). As shown in the examples, in more than a third of the exosomes a detectable amount of siRNA was observed. Moreover, PTEN-siRNA-loaded exosomes promoted robust axonal regeneration of dorsal root ganglia neurons in vitro (FIG. 7). When moved to the in vivo studies, histological and microCT imaging of the whole central nervous system confirmed that intranasally administered exosomes had crossed blood brain barrier, homed to the spinal cord lesion, and were internalized by neurons in the lesion (FIG. 2). More strikingly, intranasal PTEN-siRNA-loaded exosomes promoted robust axonal regeneration and angiogenesis, accompanied with decreased astrogliosis and microgliosis (FIG. 13). Moreover, the intranasal ExoPTEN treatment partially restored electrophysiological and structural integrity, and most importantly, enabled remarkable functional locomotor recovery. (FIG. 11).

According to the teaching of the present invention, exosomes loaded with agents capable of downregulating expression and/or activity of PTEN are useful in treating other neurological diseases or conditions in general and more specifically, degenerative neurological diseases of conditions. In particular it is clear from the present invention that inhibition of activity, and in particular inhibition of expression of PTEN in the site of lesion effectively treated spinal cord injury.

According to one aspect of the present invention there is provided a pharmaceutical composition comprising particles loaded with an exogenous phosphatase and tensin homolog (PTEN) inhibitor.

The terms "phosphatase and tensin homolog" "PTEN" are used herein interchangeably and refer to human phosphatase and tensin homolog enzyme being the product of Entrez-Gene ID: 5728 and which may have an amino acid sequence composition corresponding to UniProt Accession: P60484. Other non-human homologs are easily identified using known methods, for instance BLAST search, and are considered to be within the scope of the invention. PTEN protein acts as a phosphatase to dephosphorylate phosphatidylinositol (3,4,5)-trisphosphate (PtdIns (3,4,5)P3 or PIP3). PTEN specifically catalyses the dephosphorylation of the 3' phosphate of the inositol ring in PIP3, resulting in the biphosphate product PIP2 (PtdIns(4,5)P2). This dephosphorylation is important because it results in inhibition of the AKT signaling pathway. A representative PTEN amino acid sequence is shown in SEQ ID NO: 1.

The term "particle" and "vesicle" are as used herein interchangeably and refer to a discrete entity used for a delivery of and an active agent. The term "active agent" and "active moiety" are used herein interchangeable and refer to an agent that has a biological activity, pharmacologic effect and/or therapeutic utility. Non-limiting example of the active agents are small molecules, RNA, DNA, peptides and proteins. According to some embodiments, the active agent is a non-endogenous active agent, i.e. is not naturally present in living cell. In one embodiment, the non-endogenous has the meaning that the active agent is not present in human body and/or in human cells.

The particle may comprise a vesicle or a flattened sphere limited by a lipid bilayer. The particles may comprise diameters of 40-100 nm. The particles may be formed by inward budding of the endosomal membrane. The particles may have a density of about 1.13-1.19 g/ml and may float on sucrose gradients. The particles may be enriched in cholesterol and sphingomyelin, and lipid raft markers such as GM1, GM3, flotillin and the src protein kinase Lyn. The particles may comprise one or more proteins present in mesenchymal stem cells or mesenchymal stem cell conditioned medium (MSC-CM), such as a protein characteristic or specific to the MSC or MSC-CM. They may comprise RNA, for example miRNA.

According to some embodiments, the particles are membrane vesicles. The term "membrane vesicles" as used herein refers to any vesicles structure comprising a liquid enclosed by a lipid bilayer. Thus according to some embodiments, the particles are lipid bilayer phospholipid membrane vesicles. According to some embodiments, membrane vesicles are selected from extracellular vesicles, liposomes, ectosomes, and transferosomes. According to some embodiments, the membrane vesicles are synthetic membrane vesicles. According to other embodiments, the membrane vesicles are cell derived particles. According to some embodiments, the cells are eukaryotic cells. According to one embodiment, the membranous vesicles are liposomes.

According to one embodiment, the membrane vesicles are extracellular vesicles. According to some embodiments, the pharmaceutical composition of the present invention comprises extracellular vesicles loaded with an exogenous phosphatase and tensin homolog (PTEN) inhibitor, wherein the extracellular vesicles are derived from cells.

The terms "extracellular vesicles" and "EVs" are used herein interchangeably and refer to a cell-derived vesicles comprising a membrane that encloses an internal space. Generally extracellular vesicles range in diameter from 30 nm to 1000 nm, and may comprise various macromolecular cargo either within the internal space, displayed on the external surface of the extracellular vesicle, and/or spanning the membrane. Said cargo may comprise nucleic acids, proteins, carbohydrates, lipids, small molecules, and/or combinations thereof. The term extracellular vesicles comprises the terms "exosome" and "microvesicles". The terms "exosomes" and "nanovesicle" are used herein interchangeably and refer to EVs having the size of between 30 to 100 nm in diameter. Typically, without being limited to any particular theory, exosomes are formed within the cells and released from a cell upon fusion of a multivesicular body (MVB) with the plasma membrane. Alternatively, exosomes are released directly from the plasma membrane. The term "microvesicles" as used herein refer to EVs having the size of between 100 to 1000 nm in diameter. The term "ectosomes" refers to vesicles of various size (e.g. 0.1-1 mm in diameter) that bud directly from the plasma membrane.

According to some embodiments, the extracellular vesicles are selected from exosomes, microvesicles, ectosomes, exovesicles and a combination thereof.

According to one embodiment, the EVs are exosomes. The exosomes may have at least one of the following properties: (a) have a size of between 50 nm and 100 nm as determined by electron microscopy; (b) comprises a complex of molecular weight >100 kDa, comprising proteins of <100 kDa; (c) comprises a complex of molecular weight >300 kDa, comprising proteins of <300 kDa; (d) comprises a complex of molecular weight >1000 kDa; or (e) a hydrodynamic radius of below 100 nm, as determined by laser diffraction or dynamic light scattering. According to one embodiment, the exosomes have a diameter of from 50 to 100 nm.

According to another embodiment, the extracellular vesicles are microvesicles. According to one embodiment, the EVs are microvesicles. According to one embodiment, the microvesicles have a diameter of from 100 to 1000 nm, from 120 to 800 nm, from 150 to 600 nm or from 200 to 400 nm. According to another embodiment, the microvesicles have a size of 100 to 300 nm or 150 to 250 nm. According to some embodiments, the EVs have a diameter to 30 to 250 nm or from 50 to 200 nm. According to some embodiments, the EVs have a diameter to 70 to 170 nm or from 80 to 150 nm.

The EVs may have a size of greater than 2 nm. The EVs may have a size of greater than 5 nm, 10 nm, 20 nm, 30 nm, 40 nm or 50 nm. The EVs may have a size of greater than 100 nm, such as greater than 150 nm. The EVs may have a size of substantially 200 nm or greater.

The EVs may have a range of sizes, such as between 2 nm to 20 nm, 2 nm to 50 nm, 2 nm to 100 nm, 2 nm to 150 nm or 2 nm to 200 nm. The EVs may have a size between 20 nm to 50 nm, 20 nm to 100 nm, 20 nm to 150 nm or 20 nm to 200 nm. The EVs may have a size between 50 nm to 100 nm, 50 nm to 150 nm or 50 nm to 200 nm. The EVs may have a size between 100 nm to 150 nm or 100 nm to 200 nm. The EVs may have a size between 150 nm to 200 nm. The EVs may have a size of 100 to 600 nm, 150 to 500 nm, or 200 to 400 nm.

The size may be determined by various means. In principle, the size may be determined by size fractionation and filtration through a membrane with the relevant size cut-off. The particle size may then be determined by tracking segregation of component proteins with SDS-PAGE or by a biological assay.

The size may comprise a hydrodynamic radius. The hydrodynamic radius of the EVs may be below 100 nm. It may be between about 30 nm and about 70 nm. The hydrodynamic radius may be between about 40 nm and about 60 nm, such as between about 45 nm and about 55 nm. The hydrodynamic radius may be about 50 nm. The hydrodynamic radius of the EVs may be determined by any suitable means, for example, laser diffraction or dynamic light scattering.

According to a further embodiment, the extracellular vesicles are a combination of exosomes and microvesicles. According to some embodiments, the extracellular vesicles are isolated extracellular vesicles. According to yet another embodiment, the EVs are exovesicles or ectosomes.

As described hereinabove, the extracellular vesicles are derived from cells. The terms "derived from" and "originated from" are used herein interchangeably and refer to vesicles that are produced within, by, or from, a specified cell, cell type, or population of cells. As used herein, the terms "parent cell", "producer cell" and "original cell" include any cell from which the extracellular vesicle is derived and isolated. The terms also encompasses a cell that shares a protein, lipid, sugar, or nucleic acid component of the extracellular vesicle. For example, a "parent cell" or "producer cell" include a cell which serves as a source for the extracellular vesicle. According to some embodiments, the cells are eukaryotic cells.

The extracellular vesicles (EVs) may be derived from biological cells by any of several means, for example by secretion, budding or dispersal from the biological cells. The EVs may be something that is isolatable from a mesenchymal stem cell (MSC), neural crest cell (NCC), mesenchymal stem cell conditioned medium (MSC-CM) or neural crest cell conditioned medium. The EVs may be responsible for or have at least an activity of the parent cells such as of MSC, NCC, NCC-CM or MSC-CM. The EVs may be responsible for, and carry out, substantially most or all of the functions of the activity of the parent cells such as of MSC, NCC, NCC-CM or MSC-CM. For example, the EVs may be a substitute (or biological substitute) for the MSC, NCC, NCC-CM or MSC-CM. For example, the extracellular vesicles may be produced, exuded, emitted or shed from the biological cells. Where the biological cell is in cell culture, the particle may be secreted into the cell culture medium.

Examples of biological cells from which the EVs may be derived include, adherent cells which express mesenchymal markers such as mesenchymal stem cells, oral mucosa stem cells or olfactory ensheathing cells, astrocytes, and neural crest cells. Thus, according to some embodiments, the present invention provides a pharmaceutical composition comprising extracellular vesicles loaded with an exogenous PTEN inhibitor, wherein the extracellular vesicles are derived from adherent cells expressing mesenchymal markers. According to one embodiment, the adherent cells expressing mesenchymal markers are selected from mesenchymal stem cells (MSC), oral mucosa stem cells and olfactory ensheathing cells. According to one embodiment, the cells are mesenchymal stem cells (MSC).

The term "mesenchymal stem cells" refers to multipotent stromal cells that can differentiate into a variety of cell types, as well known in the art, including to: osteoblasts (bone cells), chondrocytes (cartilage cells), myocytes (muscle cells) and adipocytes (fat cells).

In their pluripotent state, mesenchymal stem cells typically express the following markers: CD105, CD166, CD29, CD90, and CD73, and do not express CD34, CD45 and CD133.

Mesenchymal stem cells may be isolated from a variety of tissues including but not limited to bone marrow, adipose tissue, dental pulp, oral mucosa, peripheral blood and amniotic fluid. According to one embodiment, the mesenchymal stem cells are isolated from to bone marrow. According to one embodiment, the mesenchymal stem cells are originated from a site selected from bone marrow, adipose tissue, umbilical cord, dental pulp, oral mucosa, peripheral blood and amniotic fluid. According to some embodiments, the EVs are derived from bone marrow originated MSC. According to other embodiment, the EVs are derived from the adipose tissue originated MSC. According to some such embodiments, the EVs are selected from exosomes, microvesicles and a combination thereof. According to some embodiments, the cells express CD105, CD166, CD29, CD90, and CD73 markers. According a further embodiment, the cells express CD105, CD166, CD29, CD90, and CD73, and do not express CD34, CD45 and CD133. According to some embodiments, the cells are selected from dental pulp stem cells (DPSCs), exfoliated deciduous teeth stem cells (SHED), periodontal ligament stem cells (PDLSCs), apical papilla stem cells (SCAP) and dental follicle progenitor cells (DFPCs).

The EVs may comprise one or more proteins, oligonucleotides or polynucleotides secreted by a particular cell type e.g. mesenchymal stem cell or neural crest cell. The EVs may comprise one or more proteins or polynucleotides present in mesenchymal stem cell conditioned medium (MSC-CM). In a particular embodiment, the EVs may comprise miRNAs which are derived from MSCs or neural crest cells.

For example, the EVs may comprise 10% or more, 20% or more, 30% or more, 40% or more, 50% or more, 60% or more or 70% or more of these proteins and/or polynucleotides. The EVs may comprise substantially about 75% of these proteins and/or polynucleotides. The proteins may be defined by reference to a list of proteins or gene products of a list of genes.

The EVs may have at least one property of a mesenchymal stem cell. The particle may have a biological property, such as a biological activity. The particle may have any of the biological activities of an MSC. The particle may for example have a therapeutic or restorative activity of an MSC.

Methods of isolating, purifying and expanding mesenchymal stem cells (MSCs) are known in the arts and include, for example, those disclosed by Caplan and Haynesworth in U.S. Pat. No. 5,486,359 and Jones E. A. et al., 2002, Isolation and characterization of bone marrow multipotential mesenchymal progenitor cells, Arthritis Rheum. 46(12): 3349-60.

Mesenchymal stem cell cultures may be generated by diluting BM aspirates (usually 20 ml) with equal volumes of Hank's balanced salt solution (HBSS; GIBCO Laboratories, Grand Island, N.Y., USA) and layering the diluted cells over about 10 ml of a Ficoll column (Ficoll-Paque; Pharmacia, Piscataway, N.J., USA). Following 30 minutes of centrifugation at 2,500×g, the mononuclear cell layer is removed from the interface and suspended in HBSS. Cells are then centrifuged at 1,500×g for 15 minutes and resuspended in a complete medium (MEM, a medium without deoxyribonucleotides or ribonucleotides; GIBCO); 20% fetal calf serum (FCS) derived from a lot selected for rapid growth of MSCs (Atlanta Biologicals, Norcross, Ga.); 100 units/ml penicillin (GIBCO), 100 µg/ml streptomycin (GIBCO); and 2 mM L-glutamine (GIBCO). Resuspended cells are plated in about 25 ml of medium in a 10 cm culture dish (Corning Glass Works, Corning, N.Y.) and incubated at 37° C. with 5% humidified CO2. Following 24 hours in culture, nonadherent cells are discarded, and the adherent cells are thoroughly washed twice with phosphate buffered saline (PBS). The medium is replaced with a fresh complete medium every 3 or 4 days for about 14 days. Adherent cells are then harvested with 0.25% trypsin and 1 mM EDTA (Trypsin/EDTA, GIBCO) for 5 min at 37° C., replated in a 6-cm plate and cultured for another 14 days. Cells are then trypsinized and counted using a cell counting device such as for example, a hemocytometer (Hausser Scientific, Horsham, Pa.). Cultured cells are recovered by centrifugation and resuspended with 5% DMSO and 30% FCS at a concentration of 1 to $2\times10^6$ cells per ml. Aliquots of about 1 ml each are slowly frozen and stored in liquid nitrogen.

To expand the mesenchymal stem cell fraction, frozen cells are thawed at 37° C., diluted with a complete medium and recovered by centrifugation to remove the DMSO. Cells are resuspended in a complete medium and plated at a concentration of about 5,000 cells/cm². Following 24 hours in culture, nonadherent cells are removed and the adherent cells are harvested using Trypsin/EDTA, dissociated by passage through a narrowed Pasteur pipette, and preferably replated at a density of about 1.5 to about 3.0 cells/cm². Under these conditions, MSC cultures can grow for about 50 population doublings and be expanded for about 2000 fold [Colter D C., et al. Rapid expansion of recycling stem cells in cultures of plastic-adherent cells from human bone marrow. Proc Natl Acad Sci USA. 97: 3213-3218, 2000].

MSC cultures utilized by some embodiments of the invention include three groups of cells which are defined by their morphological features: small and agranular cells (referred to as RS-1, hereinbelow), small and granular cells (referred to as RS-2, herein below) and large and moderately granular cells (referred to as mature MSCs, herein below). The presence and concentration of such cells in culture can be assayed by identifying a presence or absence of various cell surface markers, by using, for example, immunofluorescence, in situ hybridization, and activity assays.

According to some embodiment, the EVs are not derived from astrocytes. Thus the present invention contemplates compositions comprising particles loaded with PTEN inhibitor, with the proviso that the particles are not astrocyte-derived exosomes.

According to a particular embodiment, the extracellular vesicles are derived from cells expressing markers from neural crest cells. According to a particular embodiment, the EVs are derived from neural crest cells. According to another embodiment, the neural crest cells are cranial neural crest cells. According to some embodiments, the cranial neural crest cells include, but are not limited to dental pulp stem cells (DPSCs), exfoliated deciduous teeth stem cells (SHED), periodontal ligament stem cells (PDLSCs), apical papilla stem cells (SCAP) and dental follicle progenitor cells (DFPCs). According to some embodiments such cells express mesenchymal markers, as defined above.

The EVs may be produced or isolated in a number of ways. Such a method may comprise isolating the EVs from mesenchymal stem cells (MSC) or from neural crest cells (NCC).

Therefore the EVs of the present invention are isolated EVs. Thus, the present invention provides a pharmaceutical composition comprising isolated extracellular vesicles loaded with an exogenous phosphatase and tensin homolog (PTEN) inhibitor, wherein the extracellular vesicles are isolated from cells. According to some embodiments, the cells are human cells.

According to any one of the above embodiments, the extracellular vesicles are isolated extracellular vesicles. As used herein, the terms "purify," "purified," "purifying", "isolate", "isolated," and "isolating" are used interchangeably and refer to the state of a population (e.g., a plurality of known or unknown amount and/or concentration) of extracellular vesicles, that have undergone one or more processes of purification, e.g., a selection of the desired extracellular vesicles, or alternatively a removal or reduction of residual biological products. According to one embodiment, the ratio of EVs to residual parent cells is at least 2, 3, 4, 5, 6, 8 or 10 times higher, or in certain advantageous embodiments at least 50, 100 or, 1000 times higher than in the initial material. In some advantageous embodiments, the term "isolated" have the meaning of substantially cell-free or cell-free, and may be substituted by it. Thus, according to some embodiments, the pharmaceutical composition according to the present invention comprises isolated extracellular vesicles loaded with PTEN inhibitor. According to some embodiments, the pharmaceutical composition is a cell-free composition, i.e. does not comprise a detectable amount of cells.

As mentioned the lipid bilayer phospholipid membrane vesicles, e.g. extracellular vesicles, are loaded with an exogenous PTEN inhibitor.

The term "exogenous" as used herein refers to a molecule or substance (e.g., a compound, nucleic acid or protein) that originates from outside of a given membrane vesicle such as extracellular vesicles, and is not naturally present in the vesicle. With respect to extracellular vesicles, the term refers to molecules or substances that are not naturally present in the vesicle and not in the cells from which the extracellular vesicles are derived. According to some embodiments the term "exogenous" refers to synthetic non-natural molecules. According to some embodiments, the substance is artificially loaded to the extracellular vesicles or to cells from which the extracellular vesicles are derived. With respect to peptides, proteins and nucleic acids the term means that the compound is artificially loaded to the extracellular vesicles or to cells from which the vesicles are derived or artificially expressed within cells from which the vesicles are derived, however the compound is not naturally expressed in the parent cells.

The term "loaded" have the meaning that the particles, i.e. membrane vesicles, are artificially supplemented or filled with an inhibitor. With respect to the location of the inhibitor relative to a membrane vesicle, the term has the meaning of: entrapped within the interior of the vesicles, exposed or present at the surface of the vesicle (either inner and/or outer surface) embedded in the vesicle's membrane (either outer or inner or in between). According to one embodiment, the inhibitor is entrapped within the outer membrane of the vesicle. According to another embodiment, the inhibitor is entrapped within the inner membrane of the vesicle. According to a further embodiment, the inhibitor is entrapped within the liquid phase of the vesicle.

According to one embodiment, the PTEN inhibitor inhibits or downregulates PTEN activity. According to another embodiment, the PTEN inhibitor inhibits or downregulates PTEN expression.

According to a one embodiment, the PTEN inhibitor is a protein or peptide. According to another embodiment, the PTEN inhibitor is a small molecule. Examples of protein-based PTEN inhibitors include, but are not limited to those disclosed in US Patent Application Nos: 20160074472 and 20160311857, the contents of both being incorporated herein by reference. According to some embodiments, the protein-based PTEN inhibitors include peptides having sequence selected from sequence 1, 2, 5, 6 described in WO 2011/044701 and those having sequences 1-5 described in WO 2015/105957.

The protein based inhibitors of the present invention can be biochemically synthesized such as by using standard solid phase techniques. These methods include exclusive solid phase synthesis, partial solid phase synthesis methods, fragment condensation, classical solution synthesis. Solid phase polypeptide synthesis procedures are well known in the art. Synthetic peptides can be purified by preparative high performance liquid chromatography and the composition of which can be confirmed via amino acid sequencing.

Recombinant techniques may also be used to generate the protein based inhibitors of the present invention. To produce the polypeptide inhibitor of the present invention using recombinant technology, a polynucleotide encoding the peptide of the present invention is ligated into a nucleic acid expression vector, which comprises the polynucleotide sequence under the transcriptional control of a cis-regulatory sequence (e.g., promoter sequence) suitable for directing constitutive, tissue specific or inducible transcription of the polypeptides of the present invention in the host cells. Expression vectors are further described herein below.

In addition to being synthesizable in host cells, the peptides of the present invention can also be synthesized using in vitro expression systems. These methods are well known in the art and the components of the system are commercially available.

According to a particular embodiment, the protein based inhibitors are expressed in the cells from which the EVs are derived. Thus, for example, the present invention contemplates expressing a protein inhibitor in a population of MSCs and then obtaining EVs from the genetically modified MSCs.

According to some embodiments, the exogenous PTEN inhibitor is an inhibitor of PTEN expression. According to one embodiment, the inhibitor of PTEN expression is a polynucleotide or an oligonucleotide. According to another embodiment, the inhibitor is an RNA interference (RNAi) oligonucleotide. According to one embodiment, the RNA interference oligonucleotide is an siRNA. According to another embodiment, the RNA interference oligonucleotide is an shRNA.

The term "polynucleotide" as used herein refers to a long nucleic acid comprising more than 150 nucleotides. The term "oligonucleotide" as used herein refers to a short single stranded or double stranded sequence of nucleic acid such as ribonucleic acid (RNA), deoxyribonucleic acid (DNA) or mimetics thereof, said nucleic acid has typically less than or equal to 150 nucleotides. According to some embodiments, the oligonucleotide comprise 2 to 150, 10 to 100, or 15 to 50 nucleotides. According to other embodiments, the oligonucleotide comprises from 15 to 40, from 17 to 35, or from 18 to 30 nucleic acids.

In one embodiment, the polynucleotide or oligonucleotide agent is an RNA silencing agent. As used herein, the term "RNA silencing" refers to a group of regulatory mechanisms (e.g. RNA interference (RNAi), transcriptional gene silencing (TGS), post-transcriptional gene silencing (PTGS), quelling, co-suppression, and translational repression) mediated by RNA molecules which result in the inhibition or "silencing" of the expression of a corresponding protein-coding gene. RNA silencing has been observed in many types of organisms, including plants, animals, and fungi.

As used herein, the terms "RNA silencing agent", "RNA silencing molecule" and "RNA silencing oligonucleotide" are used herein interchangeably and refer to an RNA which is capable of inhibiting or "silencing" the expression of a target gene. In certain embodiments, the RNA silencing agent is capable of preventing complete processing (e.g., the full translation and/or expression) of an mRNA molecule through a post-transcriptional silencing mechanism. RNA silencing agents include noncoding RNA molecules, for example RNA duplexes comprising paired strands, as well as precursor RNAs from which such small non-coding RNAs can be generated. Exemplary RNA silencing agents include dsRNAs such as siRNAs, miRNAs and shRNAs. In one embodiment, the RNA silencing agent is capable of inducing RNA interference. In another embodiment, the RNA silencing agent is capable of mediating translational repression.

RNA interference refers to the process of sequence-specific post-transcriptional gene silencing in animals mediated by short interfering RNAs (siRNAs). The corresponding process in plants is commonly referred to as post-transcriptional gene silencing or RNA silencing and is also referred to as quelling in fungi. The process of post-transcriptional gene silencing is thought to be an evolutionarily-conserved cellular defense mechanism used to prevent the expression of foreign genes and is commonly shared by diverse flora and phyla. Such protection from foreign gene expression may have evolved in response to the production of double-stranded RNAs (dsRNAs) derived from viral infection or from the random integration of transposon elements into a host genome via a cellular response that specifically destroys homologous single-stranded RNA or viral genomic RNA.

The presence of long dsRNAs in cells stimulates the activity of a ribonuclease III enzyme referred to as dicer. Dicer is involved in the processing of the dsRNA into short pieces of dsRNA known as short interfering RNAs (siRNAs). Short interfering RNAs derived from dicer activity are typically about 21 to about 23 nucleotides in length and comprise about 19 base pair duplexes. The RNAi response also features an endonuclease complex, commonly referred to as an RNA-induced silencing complex (RISC), which mediates cleavage of single-stranded RNA having sequence complementary to the antisense strand of the siRNA duplex. Cleavage of the target RNA takes place in the middle of the region complementary to the anti sense strand of the siRNA duplex.

Accordingly, the present invention contemplates use of dsRNA to downregulate protein expression from mRNA. According to one embodiment, the dsRNA is greater than 30 bp. The use of long dsRNAs (i.e. dsRNA greater than 30 bp) has been very limited owing to the belief that these longer regions of double stranded RNA will result in the induction of the interferon and PKR response. However, the use of long dsRNAs can provide numerous advantages in that the cell can select the optimal silencing sequence alleviating the need to test numerous siRNAs; long dsRNAs will allow for silencing libraries to have less complexity than would be necessary for siRNAs; and, perhaps most importantly, long dsRNA could prevent viral escape mutations when used as therapeutics.

Various studies demonstrate that long dsRNAs can be used to silence gene expression without inducing the stress response or causing significant off-target effects.

In particular, the present invention also contemplates introduction of long dsRNA (over 30 base transcripts) for gene silencing in cells where the interferon pathway is not activated (e.g. embryonic cells and oocytes).

The present invention also contemplates introduction of long dsRNA specifically designed not to induce the interferon and PKR pathways for down-regulating gene expression. For example, Shinagwa and Ishii [*Genes & Dev.* 17 (11): 1340-1345, 2003] have developed a vector, named pDECAP, to express long double-strand RNA from an RNA polymerase II (Pol II) promoter. Because the transcripts from pDECAP lack both the 5'-cap structure and the 3'-poly (A) tail that facilitate ds-RNA export to the cytoplasm, long ds-RNA from pDECAP does not induce the interferon response.

Another method of evading the interferon and PKR pathways in mammalian systems is by introduction of small inhibitory RNAs (siRNAs) either via transfection or endogenous expression.

The term "siRNA" refers to small inhibitory RNA duplexes (generally between 18-30 basepairs) that induce the RNA interference (RNAi) pathway. Typically, siRNAs are chemically synthesized as 21mers with a central 19 bp duplex region and symmetric 2-base 3'-overhangs on the termini, although it has been recently described that chemically synthesized RNA duplexes of 25-30 base length can have as much as a 100-fold increase in potency compared with 21mers at the same location. The observed increased potency obtained using longer RNAs in triggering RNAi is theorized to result from providing Dicer with a substrate (27mer) instead of a product (21mer) and that this improves the rate or efficiency of entry of the siRNA duplex into RISC.

It has been found that position of the 3'-overhang influences potency of a siRNA and asymmetric duplexes having a 3'-overhang on the antisense strand are generally more potent than those with the 3'-overhang on the sense strand. This can be attributed to asymmetrical strand loading into RISC, as the opposite efficacy patterns are observed when targeting the antisense transcript.

Exemplary siRNA sequences that are contemplated for inhibition of PTEN include 5'-GUUAGCAGAAACAAAAGGAGAUAUCAA-3' (SEQ ID NO: 2; sense); 5'-UUGAUAUCUCCUUUU-GUUUCUGCUAAC-3' (SEQ ID NO: 3; antisense); or 5'-CAGCCGUUCGGAGGAUUAUUCGUCUTT-3' (SEQ ID NO: 4; sense), 5'-AGACGAAUAAUCC UCCGAACGGCUGTT-3' (SEQ ID NO: 5 antisense). According to one embodiment, the siRNA inhibiting PTEN expression comprises nucleic acid sequence 5'-GAGUUC-UUCCACAAACAGAA-3' (SEQ ID NO: 10; sense). According to one embodiment, the siRNA inhibiting PTEN expression comprises nucleic acid sequence 5'-UUCU-GUUUGUGGAAGAACUC-3' (SEQ ID NO: 11; antisense). According to one embodiment, the siRNA is a double stranded siRNA comprising SEQ ID NOs: 10 and 11.

One exemplary sequence to which the PTEN siRNA may be targeted is set forth in SEQ ID NO: 6 (5'-GAGTTCTTC-CACAAACAGAA-3'). Another exemplary sequence to which the PTEN siRNA may be targeted is set forth in SEQ ID NO: 7 (5'-GTATAGAGCGTGCAGATAA-3').

Thus, according to one embodiment, the PTEN inhibitor is an siRNA. According to some embodiments the siRNA may have multiple modifications that improve the entry into the membrane of vesicles or cells.

According to one embodiment, the siRNA comprise a nucleic acid sequence selected from SEQ ID NO: 10, 11, 2, 3, 4 and 5. According to one embodiment, the PTEN inhibitor is an siRNA having sequence SEQ ID NO: 2 and/or 3. According to another embodiment, the PTEN inhibitor is an siRNA having sequence SEQ ID NO: 4 and/or 5. According to some embodiments, the siRNA comprises a nucleic acid sequence targeting SEQ ID NO:6. According to other embodiments, the siRNA comprises a nucleic acid sequence targeting SEQ ID NO:7. According to one embodiment, the PTEN inhibitor is an siRNA having sequence SEQ ID NO: 10. According to another embodiment, the PTEN inhibitor is an siRNA having sequence SEQ ID NO: 11. According to a further embodiment, the PTEN inhibitor is a double stranded siRNA comprising sequence SEQ ID NO: 10 and 11.

According to another embodiment, PTEN inhibitor is an siRNA being a variant of nucleic acid sequence selected from SEQ ID NO: 10, 11, 2, 3, 4 and 5. According to one embodiment, the variant has at least 70% sequence identity to the original sequence. According to another embodiment, the variant has at least 80%, 85% or 90% sequence identity to the original sequence. According to one embodiment, the variant has the activity of the original sequence.

The terms "homolog" "variant", "DNA variant", "sequence variant" and "polynucleotide variant" are used herein interchangeably and refer to a DNA polynucleotide or oligonucleotide having at least 70% sequence identity to the original sequence. The variant may include mutations such as deletion, addition or substitution such that the mutations do not change the open reading frame and the polynucleotide encodes a peptide or a protein having substantially similar structure and function as a peptide or a protein encoded by the parent polynucleotide. According to some embodiments, the variants are conservative variants. The term "conservative variants" as used herein refers to variants in which a change of one or more nucleotides in a given codon position results in no alteration in the amino acid encoded at that position. Thus, the peptide or the protein encoded by the conservative variants has 100% sequence identity to the peptide or the protein encoded by the parent polynucleotide. According to some embodiments, the variant is a non-conservative variant encoding to a peptide or a protein being a conservative analog of the peptide of the protein encoded by the parent polynucleotide. According to some embodiments, the variant has at least 75%, at least 80% at least 85%, at least 90%, at least 95%, at least 98% or at least 99% sequence identity to the original sequence.

According to another embodiment, the siRNA is an siRNA that is complementary to the sequence encoding PTEN and inhibits its expression and/or translation. According to one embodiment, the siRNA is complementary to a sequence selected from SEQ ID NO: 6 and 7. According to one embodiment, the siRNA comprises a sequence complementary to a fragment of a nucleic acid encoding PTEN protein and inhibits its expression. According to one embodiment, the siRNA comprises a sequence complementary to a fragment of a nucleic acid encoding SEQ ID NO:1. According to one embodiment, such an siRNA has 85%, 88%, 90%, 92%, 95%, 98%, 99% or 100% complementarity to said sequence.

It will be appreciated that more than one siRNA agent may be used to down-regulate a target gene. Thus, for example, the present invention contemplates use of at least two siRNAs that target PTEN.

The terms "have", "has", "having" and "comprising" may also encompass the meaning of "consisting of" and "consisting essentially of", and may be substituted by these terms.

The strands of a double-stranded interfering RNA (e.g., a siRNA) may be connected to form a hairpin or stem-loop structure (e.g., a shRNA). Thus, as mentioned the RNA silencing agent of the present invention may also be a short hairpin RNA (shRNA).

The term "shRNA", as used herein, refers to an RNA agent having a stem-loop structure, comprising a first and second region of complementary sequence, the degree of complementarity and orientation of the regions being sufficient such that base pairing occurs between the regions, the first and second regions being joined by a loop region, the loop resulting from a lack of base pairing between nucleotides (or nucleotide analogs) within the loop region. The number of nucleotides in the loop is a number between and including 3 to 23, or 5 to 15, or 7 to 13, or 4 to 9, or 9 to 11. Some of the nucleotides in the loop can be involved in base-pair interactions with other nucleotides in the loop. Examples of oligonucleotide sequences that can be used to form the loop include 5'-UUCAAGAGA-3' (SEQ ID NO: 8;) and 5'-UUUGUGUAG-3' (SEQ ID NO: 9). It will be recognized by one of skill in the art that the resulting single chain oligonucleotide forms a stem-loop or hairpin structure comprising a double-stranded region capable of interacting with the RNAi machinery. According to some embodiments, the shRNA comprises nucleic acid SEQ ID NO: 2. According to other embodiments, the shRNA comprises nucleic acid SEQ ID NO: 4. According to one embodiment, the shRNA comprises nucleic acid SEQ ID NO: 2 and 3. According to another embodiment, the shRNA comprises nucleic acid SEQ ID NO: 4 and 5. According to some embodiments, the shRNA comprises nucleic acid SEQ ID NO: 10 or 11. According to other embodiments, the shRNA comprises nucleic acid SEQ ID NO: 10 and 11.

According to another embodiment the RNA silencing agent may be a miRNA. MiRNAs are small RNAs made from genes encoding primary transcripts of various sizes. They have been identified in both animals and plants. The primary transcript (termed the "pri-miRNA") is processed through various nucleolytic steps to a shorter precursor miRNA, or "pre-miRNA." The pre-miRNA is present in a folded form so that the final (mature) miRNA is present in a duplex, the two strands being referred to as the miRNA (the strand that will eventually basepair with the target) The pre-miRNA is a substrate for a form of dicer that removes the miRNA duplex from the precursor, after which, similarly to siRNAs, the duplex can be taken into the RISC complex. It has been demonstrated that miRNAs can be transgenically expressed and be effective through expression of a precursor form, rather than the entire primary form.

Unlike, siRNAs, miRNAs bind to transcript sequences with only partial complementarity and repress translation without affecting steady-state RNA levels. Both miRNAs and siRNAs are processed by Dicer and associate with components of the RNA-induced silencing complex. It was hypothesized that gene regulation through the miRNA pathway versus the siRNA pathway is determined solely by the degree of complementarity to the target transcript. It is speculated that siRNAs with only partial identity to the mRNA target will function in translational repression, similar to a miRNA, rather than triggering RNA degradation.

It will be appreciated that the RNA silencing agent of the present invention need not be limited to those molecules containing only RNA, but further encompasses chemically-modified nucleotides and non-nucleotides.

Additional agents capable of downregulating PTEN include ribozymes, DNAzymes and agents of the CRISPR system (e.g. CRISPR/Cas).

Ribozymes are being increasingly used for the sequence-specific inhibition of gene expression by the cleavage of mRNAs encoding proteins of interest. The possibility of designing ribozymes to cleave any specific target RNA has rendered them valuable tools in both basic research and therapeutic applications. In the therapeutics area, ribozymes have been exploited to target viral RNAs in infectious diseases, dominant oncogenes in cancers and specific somatic mutations in genetic disorders. Most notably, several ribozyme gene therapy protocols for HIV patients are already in Phase 1 trials. More recently, ribozymes have been used for transgenic animal research, gene target validation and pathway elucidation. Several ribozymes are in various stages of clinical trials. ANGIOZYME® was the first chemically synthesized ribozyme to be studied in human clinical trials. ANGIOZYME® specifically inhibits formation of the VEGF-r (Vascular Endothelial Growth Factor receptor), a key component in the angiogenesis pathway. Ribozyme Pharmaceuticals, Inc., as well as other firms have demonstrated the importance of anti-angiogenesis therapeutics in animal models. HEPTAZYME®, a ribozyme designed to selectively destroy Hepatitis C Virus (HCV) RNA, was found effective in decreasing Hepatitis C viral RNA in cell culture assays (Ribozyme Pharmaceuticals, Incorporated—WEB home page).

Another agent capable of downregulating PTEN is a RNA-guided endonuclease technology e.g. CRISPR system.

An additional method of regulating the expression of PTEN gene in cells is via triplex forming oligonucleotides (TFOs). Studies have shown that TFOs can be designed which can recognize and bind to polypurine/polypyrimidine regions in double-stranded helical DNA in a sequence-specific manner. Modification of the oligonucleotides, such as the introduction of intercalators and backbone substitutions, and optimization of binding conditions (pH and cation concentration) have aided in overcoming inherent obstacles to TFO activity such as charge repulsion and instability, and it was recently shown that synthetic oligonucleotides can be targeted to specific sequences.

Thus for any given sequence in the PTEN a triplex forming sequence may be devised. Triplex-forming oligonucleotides preferably are at least 15, more preferably 25, still more preferably 30 or more nucleotides in length, up to 50 or 100 bp.

As mentioned, the extracellular vesicles of the present invention may be loaded with polynucleotide or oligonucleotide agent inhibiting PTEN expression directly.

In order to facilitate membrane vesicles (e.g. exosome) loading, polynucleotide or oligonucleotide cargo may contain one or more hydrophobic modifications. Hydrophobic modifications increase the hydrophobicity of the polynucleotide or oligonucleotide cargo, as compared to native (non-modified) RNA or DNA. In certain embodiments, the hydrophobic modifications increase the hydrophobicity of the polynucleotide or oligonucleotide by at least two orders of magnitude (e.g., at least 3, 4, 5, 6, 7, 8, 9, 10 or more orders of magnitude) relative to native (non-modified) RNA or DNA. In other embodiments, the hydrophobic modifications increase the hydrophobicity of the polynucleotide or oligonucleotide by at least 10 orders of magnitude relative to native (non-modified) RNA or DNA. In other embodiments, the hydrophobic modifications increase the hydrophobicity of the polynucleotide or oligonucleotide by at least two orders of magnitude (e.g., at least 3, 4, 5, 6, 7, 8, 9, 10 or more orders of magnitude) relative to the unmodified polynucleotide or oligonucleotide. In other embodiments, the hydrophobic modifications increase the hydrophobicity of the polynucleotide or oligonucleotide by at least ten orders of magnitude relative to the unmodified polynucleotide or oligonucleotide. Increase in hydrophobicity can be assessed using any suitable method. For example, hydrophobicity can be determined by measuring the percentage solubility in an organic solvent, such as octanol, as compared to solubility in an aqueous solvent, such as water.

In some embodiments, the hydrophobic character of polynucleotide or oligonucleotide cargo can be increased by increasing the proportion of nucleotides within the polynucleotide or oligonucleotide molecule that are hydrophobically modified. For example, in one embodiment, 20% or more of the nucleotides in an oligonucleotide or polynucleotide molecule are hydrophobically modified, e.g., 25% or more, 30% or more, 40% or more, 50% or more, 60% or more, 70% or more, 80% or more, 90% or more, 95% or more, 99% or more, etc. of the nucleotides in an oligonucleotide or polynucleotide molecule are hydrophobically modified. In one embodiment, 100% of the nucleotides in an oligonucleotide or polynucleotide molecule are hydrophobically modified. In an exemplary embodiment, 30% or more of the nucleotides in an oligonucleotide or polynucleotide molecule contain hydrophobic modifications. Increasing the proportion of hydrophobically modified nucleotides in an oligonucleotide or polynucleotide molecule can be useful when, for example, the hydrophobic modification is weakly hydrophobic, for example, a 2'O-methyl modification. In embodiments where a strongly hydrophobic modification is employed, for example, a sterol, a lipid, etc., a single hydrophobic modification can be sufficient to facilitate exosomal loading.

In some embodiments, the hydrophobic modification is a covalent modification. Hydrophobic modifications of nucleic acid molecules can include, for example, backbone modifications, sugar modifications, base modifications and/or conjugate modifications, and combinations thereof.

Backbone modifications involve alterations to the phosphate ester linkages in the nucleic acid molecule. Examples of suitable backbone modifications include, but are not limited to, phosphorothioate modifications, phosphorodithioate modifications, p-ethoxy modifications, methylphosphonate modifications, methylphosphorothioate modifications, alkyl- and aryl-phosphates (in which the charged phosphonate oxygen is replaced by an alkyl or aryl group), alkylphosphotriesters (in which the charged oxygen moiety is alkylated), peptide nucleic acid (PNA) backbone modifications, locked nucleic acid (LNA) backbone modifications, and the like. These modifications may be used in combination with each other and/or in combination with phosphodiester backbone linkages.

In one embodiment, the hydrophobic modification is a phosphorothioate (PS) modification, where one of the non-bridging phosphate oxygen atoms is replaced by sulfur to give a PS group. This, modification provides significant resistance to nuclease degradation and has favorable pharmacokinetic properties. PS linkages can readily incorporated into oligonucleotide molecules using standard techniques, such as solid-phase oligonucleotide synthesis.

In another embodiment, the hydrophobic modification is a phosphonate modification, in which one nonbridging oxygen is replaced with an alkyl group. In other embodiments, the hydrophobic modification is a peptide nucleic acid (PNA) modification. PNAs are oligonucleotide mimics that have a peptide backbone with a neutral charge, as compared with the highly charged sugar-phosphate backbone of native RNA and DNA (see, for example. In other embodiments, the hydrophobically modified nucleic acid molecule is a phosphorodiamidate morpholino oligonucleotide (PMO).

In other embodiments, oligonucleotide cargo molecules may be hydrophobically modified at the sugar moiety (e.g., ribose, deoxyribose, etc.). Sugar modifications often occur at the 2' position of the sugar ring, where, for example, the 2' moiety can be modified or substituted with a hydrophobic moiety, such as a halo, alkoxy, aminoalkoxy, alkyl, azido or amino group. In non-limiting examples, sugar modifications can include O-methyl, F, methoxy-ethyl, and 2'-fluoro-.beta.-D-arabinonucleotide (FANA). Other 2' modifications include, for example, 2'O-allyl, 2'O-ethylamine, and 2'O-cyanoethyl modifications. In addition, modifications can be made at other sites including the 4' position of the sugar.

In other embodiments, oligonucleotide cargo molecules may contain hydrophobic base modifications. In exemplary embodiments, these modifications include phenyl, naphthyl, and isobutyl. Other embodiments include C-5 propynyl modified bases, 5-methylcytosine, 2-aminopurine, 2-amino-6-chloropurine, 2,6-diaminopurine, and hypoxanthine.

In addition to increasing the hydrophobic character of the oligonucleotide cargo, the foregoing backbone, sugar, and base modifications increase the stability of the oligonucleotides in the presence of particles (e.g. exosomes), and minimize any degradation that may occur during loading.

According to some embodiments, the RNA interference oligonucleotide such as siRNA or shRNA comprises a hydrophobic moiety. Hydrophobic moieties can also be chemically conjugated to oligonucleotide to enhance its hydrophobic character. Thus, in one embodiment, the RNA interference oligonucleotide is conjugated with the hydrophobic moiety. According to one embodiment, the said hydrophobic moiety is selected from the group consisting of a sterol, a ganglioside, a lipid, a vitamin, a fatty acid, a peptide, and a combination thereof. According to one embodiment, the RNA interference oligonucleotide is conjugated with a sterol. In exemplary embodiments, the moiety is a sterol cholesterol molecule, therefore according to such embodiments, the RNA interference oligonucleotide is conjugated with a cholesterol. According to some embodiments, one of the strands of the double stranded RNAi is conjugated with hydrophobic molecule such as cholesterol. According to other embodiments, two strands of the double stranded RNAi are conjugated with hydrophobic molecule such as cholesterol. According to other embodiments, the RNA interference oligonucleotide is conjugated with a molecule selected from monosialotetrahexosylganglioside (GM1), a lipid, a vitamin, a small molecule, a peptide, or a combination thereof. In some embodiments, the moiety is a lipid. For example, in certain embodiments, the moiety is palmitoyl. In some embodiments, the moiety is a sterol, e.g., cholesterol. Additional hydrophobic moieties include, for example, phospholipids, vitamin D, vitamin E, squalene, and fatty acids. In another exemplary embodiment, the oligonucleotide cargo is conjugated to myristic acid, or a derivative thereof (e.g., myristoylated oligonucleotide cargo). In some embodiments, the hydrophobic moiety is conjugated at the termini of the oligonucleotide cargo (i.e., "terminal modification"). In other embodiments, the hydrophobic moiety is conjugated to other portions of the oligonucleotide molecule.

According to some particular embodiments, the PTEN inhibitor is an siRNA molecule comprising nucleic acid sequence selected from SEQ ID NO: 10, 11, 2, 3, 4, and 5, and conjugated to a hydrophobic molecule, such as cholesterol. According to some embodiments, the siRNA comprises nucleic acid sequence targeting the nucleic acid sequence selected from SEQ ID NOs: 6 and 7, and conjugated with a hydrophobic molecule, such as cholesterol. According to some embodiments, the siRNA comprises nucleic acid sequence targeting the nucleic acid sequence selected from SEQ ID NOs: 6 and 7, and conjugated with a hydrophobic molecule, such as cholesterol. According to one embodiment, the PTEN inhibitor is an siRNA having sequence SEQ ID NO: 10 conjugated with a cholesterol. According to another embodiment, the PTEN inhibitor is a double stranded siRNA comprising sequence SEQ ID NO: 10 conjugated with a cholesterol together with SEQ ID NO: 11. According to specific embodiments, the siRNA comprises a sequence complementary to a fragment of a nucleic acid encoding PTEN protein and inhibits its expression and wherein at least one of the sequences of the siRNA is conjugated with a hydrophobic molecule, such as cholesterol. According to one embodiment, PTEN protein comprises SEQ ID NO:1.

In specific embodiments, the oligonucleotide is stabilized by incorporation of one or more backbone modifications, sugar modifications, and/or base modifications as described herein, and additionally is conjugated to a hydrophobic moiety. For example, the oligonucleotide in certain embodiments can contain one or more backbone modifications, sugar modifications, and/or base modifications to at least 30%, at least 35%, at least 40%, at least 45%, at least 50%, at least 55%, at least 60%, at least 65% or more of the nucleotides, and further is conjugated to a hydrophobic moiety as described herein, e.g., conjugated to a sterol, GM1, a lipid, a vitamin, a small molecule, or a peptide, or a combination thereof. In an exemplary embodiment, the oligonucleotide cargo is conjugated to a sterol, e.g., cholesterol. In another exemplary embodiment, the oligonucleotide cargo is conjugated to GM1. In another exemplary embodiment, the oligonucleotide cargo is conjugated to myristic acid, or a derivative thereof.

In some embodiments, the hydrophobically modified oligonucleotide can include a detectable label. Exemplary labels include fluorescent labels and/or radioactive labels. In embodiments where hydrophobically modified oligonucleotides are fluorescently labeled, the detectable label can be, for example, Cy3. Adding a detectable label to hydrophobically modified oligonucleotides can be used as a way of labeling exosomes, and following their biodistribution. In other embodiments, a detectable label can be attached to exosomes directly, for example, by way of labeling an exosomal lipid and/or an exosomal peptide.

Nucleic acids can be synthesized using any number of procedures known in the art. A number of automated nucleic acid synthesizers are commercially available for this purpose. In some embodiments, the nucleic acid cargo is a synthetic oligonucleotide. In other embodiments, nucleic acids can be prepared using, for example, restriction enzymes, exonucleases, or endonucleases.

According to any one of the above embodiment, the pharmaceutical composition according to the present invention further comprise Chondroitinase ABC lyase.

Chondroitin ABC lyase (EC 4.2.2.4, chondroitinase, chondroitin ABC eliminase, chondroitinase ABC) is an enzyme with systematic name chondroitin ABC lyase. This enzyme catalyses the following chemical reaction:

Eliminative degradation of polysaccharides containing 1,4-beta-D-hexosaminyl and 1,3-beta-D-glucuronosyl or 1,3-alpha-L-iduronosyl linkages to disaccharides containing 4-deoxy-beta-D-gluc-4-enuronosyl groups. In one embodiment, the Chondroitinase ABC lyase is derived from *Proteus vulgaris*.

The Chondroitinase ABC may be provided as a protein per se or in a carrier, e.g. in particles (as described herein above). According to one embodiment, the pharmaceutical composition comprises extracellular vesicles loaded with an exogenous PTEN inhibitor and Chondroitinase ABC as a protein. According to another embodiment, the pharmaceutical composition comprises extracellular vesicles loaded with an exogenous PTEN inhibitor and with Chondroitinase ABC, in the same type of extracellular vesicles (e.g. mesenchymal stem cell derived exosomes). According to further embodiment, the pharmaceutical composition comprises extracellular vesicles loaded with an exogenous PTEN inhibitor and other, different extracellular vesicles loaded with Chondroitinase ABC. According to some embodiment, the different extracellular vesicles may be of the same type (e.g. mesenchymal stem cell derived exosomes) or different types (extracellular vesicles derived from different cell sources, e.g. PTEN inhibitor is comprised in mesenchymal stem cell derived exosomes and Chondroitinase ABC is comprised in dental pulp derived exosomes, or vice versa).

According to some embodiments, the pharmaceutical composition further comprises an addition therapeutic agents useful in treating neurological disorders. Non-limiting examples of such active agents are gangliosides; antibiotics, neurotransmitters, neurohormones, toxins, neurite promoting molecules; and antimetabolites small molecule agents and precursors of neurotransmitter molecules such as L-DOPA. Additionally, or alternatively, the additional therapeutic agent is cells capable of alleviating at least one symptom of the neurological disease.

The term "pharmaceutical composition" as used herein refers to a composition comprising membrane vesicles loaded with an exogenous PTEN inhibitor, in particular extracellular vesicles such as exosomes, formulated together with one or more pharmaceutically acceptable carriers.

Formulation of the pharmaceutical composition may be adjusted according to applications. In particular, the pharmaceutical composition may be formulated using a method known in the art so as to provide rapid, continuous or delayed release of the active ingredient after administration to mammals. For example, the formulation may be any one selected from among plasters, granules, lotions, liniments, lemonades, aromatic waters, powders, syrups, ophthalmic ointments, liquids and solutions, aerosols, sprays, extracts, elixirs, ointments, fluidextracts, emulsions, suspensions, decoctions, infusions, ophthalmic solutions, tablets, suppositories, injections, spirits, capsules, creams, troches, tinctures, pastes, pills, and soft or hard gelatin capsules.

The term "pharmaceutically acceptable carrier" or "pharmaceutically acceptable excipient" as used herein refers to any and all solvents, dispersion media, preservatives, antioxidants, coatings, isotonic and absorption delaying agents, surfactants, fillers, disintegrants, binders, diluents, lubricants, glidants, pH adjusting agents, buffering agents, enhancers, wetting agents, solubilizing agents, surfactants, antioxidants the like, that are compatible with pharmaceutical administration. The use of such media and agents for pharmaceutically active substances is well known in the art. The compositions may contain other active compounds providing supplemental, additional, or enhanced therapeutic functions. solid carriers or excipients such as, for example, lactose, starch or talcum or liquid carriers such as, for example, water, fatty oils or liquid paraffins. Other examples of the carrier include culture medium such as DMEM or RPMI; hypothermic storage medium containing components that scavenge free radicals, provide pH buffering, oncotic/osmotic support, energy substrates and ionic concentrations that balance the intracellular state at low temperatures; and mixtures of organic solvents with water.

Examples, without limitation, of excipients include albumin, plasma, serum and cerebrospinal fluid (CSF), antioxidants such as N-Acetylcysteine (NAC) or resveratrol. Typically, the pharmaceutical carrier preserves the number of particles and the activity of the PTEN inhibitor (e.g. the amount is not reduced by more than 90%) in the composition for at least 24 hours, at least 48 hours or even at least 96 hours.

According to any one of the above embodiment, the pharmaceutical composition is formulated for administration via an administration route selected from intranasal, intra-lesion, intrathecal, intravenous, intramuscular, subcutaneous, sublingual, oral, and intracerebral administration route. According to one embodiment, the pharmaceutical composition is formulated for intranasal administration. According to some embodiment, such pharmaceutical composition is in a form of liquid solution, nasal drops, spray, measured stray. According to other embodiment, the pharmaceutical composition is formulated for injection, e.g. intra-lesion, intrathecal or intravenous injection. According to such embodiments, the pharmaceutical composition is in a form of sterile solution of injection.

According to some embodiments, the present invention provides a pharmaceutical composition comprising extracellular vesicles loaded with an exogenous phosphatase and tensin homolog (PTEN) inhibitor, wherein the extracellular vesicles are derived from cells. According to one embodiment, the EVs are selected from exosomes, microvesicles and a combination thereof. According to another embodiment, the extracellular vesicles are exosomes. According to some embodiments, the extracellular vesicles are derived from MSCs. According to one embodiment, the PTEN inhibitor is an inhibitor of PTEN expression.

According to another embodiment, the inhibitor of PTEN expression is an siRNA. According to another embodiment, the inhibitor of PTEN expression is an shRNA According to some embodiments, the siRNA comprises a nucleic acid sequence selected from SEQ ID NO: 10, 11, 2, 3, 4 and 5. According to one embodiment, the PTEN inhibitor is an siRNA comprising nucleic acid SEQ ID NO: 10. According to another embodiment, the PTEN inhibitor is a double stranded siRNA comprising sequence SEQ ID NO: 10 and SEQ ID NO: 11. According to some embodiments, the siRNA comprises a nucleic acid sequence targeting SEQ ID NO:6. According to other embodiments, the siRNA comprises a nucleic acid sequence targeting SEQ ID NO:7. According to one embodiment, the siRNA comprises a sequence complementary to a fragment of a nucleic acid encoding PTEN protein and inhibits its expression. According to one embodiment, the siRNA comprises a sequence complementary to a fragment of a nucleic acid encoding SEQ ID NO:1. According to some embodiments, the siRNA is conjugated with cholesterol. According to some embodiments, the present invention provides a pharmaceutical composition comprising extracellular vesicles selected from exosomes, microvesicles or a combination thereof loaded with siRNA molecule capable of inhibiting PTEN expression and conjugated with cholesterol. According to such embodiments, the siRNA has a nucleic acid sequence SEQ ID NO: 2 and 3. According other such embodiments, the siRNA has a nucleic acid sequence SEQ ID NO: 4 and 5. According to another such embodiment, the PTEN inhibitor is a double stranded siRNA comprising sequences SEQ ID NO: 10 and SEQ ID NO: 11. According to some embodiments, the siRNA comprises a nucleic acid sequence targeting SEQ ID NO:6. According to other embodiments, the siRNA comprises a nucleic acid sequence targeting SEQ ID NO: 7. According to one embodiment, the siRNA comprises a sequence complementary to a fragment of a nucleic acid encoding SEQ ID NO:1. According to some embodiments, the pharmaceutical composition is formulated from intranasal administration. According to another embodiment, the pharmaceutical composition is formulated from intra-lesion administration. According to yet another embodiment, the pharmaceutical is formulated from oral administration. According to some embodiment, the pharmaceutical composition is co-administered with Chondroitinase ABC.

According to one embodiment, the present invention provides a pharmaceutical composition comprising extracellular vesicles selected from exosomes, microvesicles and a combination thereof, wherein said extracellular vesicles are loaded with siRNA or shRNA capable of inhibiting PTEN expression and wherein the pharmaceutical composition is formulated for intranasal or intrathecal administration. According to one embodiment, the siRNA or the shRNA is conjugated with cholesterol. According to one embodiment, the PTEN inhibitor is a double stranded siRNA comprising sequence SEQ ID NO: 10, optionally conjugated with a cholesterol, and SEQ ID NO: 11 or variant(s) thereof. According to another embodiment, the siRNA or the shRNA comprises nucleic acid sequence SEQ ID NO: 2 and/or 3, or a variant thereof. According to a further embodiment, the siRNA or the shRNA comprises nucleic acid sequence SEQ ID NO: 4 and/or 3, or a variant thereof.

According to any one of the above embodiments, the pharmaceutical composition of the present invention is useful for treating neurological disease, disorder, damage or condition. According to one embodiment, the neurological condition is spinal cord injury.

According to one embodiment, the membrane vesicles are liposomes. Thus, according to one embodiment, the present invention provides a pharmaceutical composition comprising liposomes loaded with an exogenous phosphatase and tensin homolog (PTEN) inhibitor. The term "liposome" refers to a microscopic closed vesicle having an internal phase enclosed by lipid bilayer. A liposome can be a small single-membrane liposome such as a small unilamellar vesicle (SUV), large single-membrane liposome such as a large unilamellar vesicle (LUV), a still larger single-membrane liposome such as a giant unilamellar vesicle (GUV), a multilayer liposome having multiple concentric membranes such as a multilamellar vesicle (MLV), or a liposome having multiple membranes that are irregular and not concentric such as a multivesicular vesicle (MVV). According to one embodiment, the liposomes are SUVs. According to other embodiment, the liposomes are MLVs.

According to one embodiment, the liposomes are SUVs. According to other embodiment, the liposomes are MLVs. According to one embodiment, the liposomes comprise a liposome forming lipid selected from the group consisting of a phosphatidylcholine, phosphatidylinositol, phosphatidylglycerol, phosphatidylethanolamine, 1-palmitoyl-2-oleoylphosphatidyl choline (POPC), sphingophospholipids, distearoyl, and any combination thereof. According to another embodiment, the liposome forming lipid is phosphatidylcholine. According to one embodiment, the phosphatidylcholine is hydrogenated soy phosphatidylcholine (HSPC). According to other embodiments, the phosphatidylethanolamine is 1,2-distearoyl-sn-glycero-3-phosphoethanolamine (DSPE), and said distearoyl is distearoyl glycol (DSG) or oxycarbonyl-3-amino-1,2-propanediol distearoylester (DS). According to another embodiment, the liposomes comprise stabilizing polymer molecule such as polyalkylether, polysialic acid, polylactic acid and polyglycolic acid. According to one embodiment, the liposomes comprise PEG. According to some embodiments, the liposomes further comprise cholesterol.

According to one embodiment, the liposomes are loaded with PTEN inhibitor. All terms and embodiments related to PTEN inhibitor apply herein. According to one embodiment, the PTEN inhibitor is an inhibitor of PTEN expression. According to some embodiments, the inhibitor of PTEN expression is an RNA interference (RNAi) oligonucleotide. According to one embodiment, the RNAi oligonucleotide is selected from siRNA and shRNA. According to another embodiment, the siRNA comprising a nucleic acid sequence selected from SEQ ID NO: 10, 11, 2, 3, 4 and 5. According to some embodiments, the siRNA comprises a nucleic acid sequence targeting SEQ ID NO:6. According to other embodiments, the siRNA comprises a nucleic acid sequence targeting SEQ ID NO:7. According to a further embodiment, said RNAi oligonucleotide such as siRNA or shRNA is conjugated with a hydrophobic moiety. According to yet another embodiment, the hydrophobic moiety is selected from the group consisting of a sterol, a ganglioside, a lipid, a vitamin, a fatty acid, a hydrophobic peptide, and a combination thereof. According to one embodiment, the siRNA or the siRNA is conjugated with cholesterol.

According to the teaching of the present invention, the pharmaceutical composition of the present invention is for use in treating a neurological disease, disorder or condition in a subject. Thus according to some embodiment, the pharmaceutical composition comprising particles loaded with an exogenous phosphatase and tensin homolog (PTEN) inhibitor for use in treating a neurological disease, disorder or condition in a subject in need thereof. According to some embodiments, the particle are membrane vesicles. According to some preferred embodiments, the membrane vesicles are extracellular vesicles.

Thus according to some embodiments, the present invention provides a pharmaceutical composition comprising extracellular vesicles loaded with an exogenous phosphatase and tensin homolog (PTEN) inhibitor, for use in treating a neurological disease, disorder or condition in a subject in need thereof.

The term "neurological disease, disorder or condition" refers to a disease, disorder or condition of the brain, spine and/or the nerves that connect them.

According to a particular embodiment, the condition is due to an injury. According to one embodiment, the injury is to spinal cord, i.e. spinal cord injury (SCI). According to other embodiment, the neurological disease, disorder or condition is a neuronal damage.

The terms "spinal cord injury" and "SCI" are used herein interchangeably and refer to an injury to the spinal cord. According to one embodiment, the injury is a result of a trauma. According to another embodiment, the injury or a damage is a result of a degeneration or a disease. Depending on where the spinal cord and nerve roots are damaged, the symptoms can vary widely, for example from pain to paralysis to incontinence. Spinal cord injuries are described at various levels of "incomplete", which can vary from having no effect on the patient to a "complete" injury which means a total loss of function. Spinal cord injuries have many causes, but are typically associated with major trauma from motor vehicle accidents, falls, sports injuries, and violence. Thus, according to one embodiment, the SCI is selected from a complete and incomplete SCI. According to some embodiment, the spinal cord injury is selected from an acute or chronic SCI. The spinal cord injury may be susceptible to secondary tissue injury, including but not limited to: glial scarring, myelin inhibition, demyelination, cell death, lack of neurotrophic support, ischemia, free-radical formation, and excitotoxicity.

Diseases of the spinal cord include but are not limited to autoimmune diseases (e.g. multiple sclerosis), inflammatory diseases (e.g. Arachnoiditis), neurodegenerative diseases, polio, spina bifida and spinal tumors.

Subjects that may be treated according to the teaching of the present invention include mammalian subjects, such as humans, mice, rats, monkeys, dogs and cats. In one embodiment, the subject is a human subject.

The term "treating" a condition or patient refers to taking steps to obtain beneficial or desired results, including clinical results. Beneficial or desired clinical results include, but are not limited to, or ameliorating abrogating, substantially inhibiting, slowing or reversing the progression of a disease, condition or disorder, substantially ameliorating or alleviating clinical or esthetical symptoms of a condition, substantially preventing the appearance of clinical or esthetical symptoms of a disease, condition, or disorder, and protecting from harmful or annoying symptoms. Treating further refers to accomplishing one or more of the following: (a) reducing the severity of the disorder; (b) limiting development of symptoms characteristic of the disorder(s) being treated; (c) limiting worsening of symptoms characteristic of the disorder(s) being treated; (d) limiting recurrence of the disorder(s) in patients that have previously had the disorder(s); and/or (e) limiting recurrence of symptoms in patients that were previously asymptomatic for the disorder(s). According to some embodiments, the term "treating" comprises neural regeneration, axonal propagation, decreased astrogliosis and microgliosis at the injury cite. According to other embodiments, the term encompasses improvement in symptoms associated with the disease or condition. According to one embodiment, the term "treating" comprises improvement in locomotor parameters. According to one embodiment, improvement in locomotor parameters comprises improvement in 20%, 30%, 40%, 50%, 60%, 70%, 80% or 90% of locomotor parameters in comparison to untreated subject. According to some embodiment, treating comprises reducing astrogliosis and/or microgliosis at the injury cite. According to one embodiment, reducing astrogliosis and/or microgliosis comprises reduce of 10%, 20%, 30%, 40%, 50%, 60%, 70%, or 80% of astrogliosis and/or microgliosis in comparison to untreated subject.

The pharmaceutical composition of the present invention may be administered using any known method. The terms "administering" or "administration of" a substance, a compound or an agent to a subject can be carried out using one of a variety of methods known to those skilled in the art. For example, a compound or an agent can be administered intranasally (e.g., by inhalation), intrathecally (into the spinal canal, or into the subarachnoid space), arterially, intradermally, intramuscularly, intraperitoneally, intravenously, subcutaneously, ocularly, sublingually, orally (by ingestion), intracerebrally, and transdermally (by absorption, e.g., through a skin duct). A compound or agent can also appropriately be introduced by rechargeable or biodegradable polymeric devices or other devices, e.g., patches and pumps, or formulations, which provide for the extended, slow or controlled release of the compound or agent.

Administering can also be performed, for example, once, a plurality of times, and/or over one or more extended periods. According to some embodiments, the composition is administered 1, 2, 3, 4, 5 or 6 times a day. According to other embodiments, the composition is administered 1, 2, 3, 4, 5 or 6 times a month. In some embodiments, the administration includes both direct administration, including self-administration, and indirect administration, including the act of prescribing a drug. For example, as used herein, a physician who instructs a patient to self-administer a drug, or to have the drug administered by another and/or who provides a patient with a prescription for a drug is administering the drug to the patient. According to one embodiment, the pharmaceutical composition of the present invention is administered intranasally. According to another embodiment, the pharmaceutical composition of the present invention is administered intra-lesion. According to one embodiment, the pharmaceutical composition is administered orally.

According to a particular embodiment, the neurological disease is a degenerative disease of the nervous system. According to one embodiment, the degenerative disease of the nervous system is selected from as Parkinson's disease, essential tremor, Huntington's disease, Alzheimer's disease, multiple sclerosis, ALS and organic psychosis. According to one embodiment, the disease is a memory disease. In one embodiment, the disease is a neurodevelopmental disorder such as autism or schizophrenia. According to another embodiment, the disease is a behavioral disease such as schizophrenia, attention deficit hyperactivity disorder, autism, Tourette's syndrome, obsessive compulsive disorder, as well as the neurobehavioral associated symptoms. According to a particular embodiment, the neurological disease is an autism spectrum disorder (ASD).

According to any one of the above embodiments, the present invention provides a pharmaceutical composition comprising membrane vesicles loaded with an exogenous phosphatase and tensin homolog (PTEN) inhibitor, for use in treating neuronal injury or damage in a subject. According to some embodiment, the neuronal injury is a spinal cord injury. According to another embodiment, the damage is to the neural cells of the brain. According to one embodiment, the injury is brain injury. According to another embodiment, the damage is due to a neurodegenerative disease. According to another embodiment, the neurodegenerative is selected from as Parkinson's disease, essential tremor, Huntington's disease, Alzheimer's disease, multiple sclerosis, ALS and organic psychosis.

Thus, according to some embodiments, the present invention provides a pharmaceutical composition comprising extracellular vesicles loaded with an exogenous phosphatase and tensin homolog (PTEN) inhibitor, for use in treating neuronal injury or damage in a subject, wherein the extracellular vesicles are derived from cells.

According to one embodiment, the extracellular vesicles are exosomes. According to another embodiment, the EVs are microvesicles. According to one embodiment, the EVs are selected from exosomes, microvesicles and a combination thereof. According to some embodiments, the extracellular vesicles are derived from MSCs. According to one embodiment, the exogenous PTEN inhibitor is an inhibitor of PTEN expression. According to another embodiment, the inhibitor of PTEN expression is an siRNA or shRNA. According to some embodiments, the siRNA comprises a nucleic acid sequence selected from SEQ ID NO: 10, 11, 2, 3, 4 and 5. According to one embodiment, the siRNA is complementary or targeting to a sequence selected from SEQ ID NO: 6 and 7. According to one embodiment, the siRNA comprises a sequence complementary to a fragment of a nucleic acid encoding PTEN protein and inhibits its expression. According to one embodiment, the PTEN comprises SEQ ID NO:1. According to one embodiment, the PTEN inhibitor is an siRNA comprising nucleic acid sequence 10. According to another embodiment, the PTEN inhibitor is a double stranded siRNA comprising sequences SEQ ID NO: 10 and SEQ ID NO: 11. According to a further embodiment, the PTEN inhibitor is shRNA comprising a nucleic acid sequence selected from SEQ ID NO: 10, 11, 2, 3, 4 and 5. According to one embodiment, the shRNA is targeting or complementary to a sequence selected from SEQ ID NO: 6 and 7. According to some particular embodiments, the shRNA is conjugated with cholesterol.

According to some embodiments, the present invention provides a pharmaceutical composition comprising EVs selected from exosomes, microvesicles or a combination thereof loaded with siRNA oligonucleotide capable of inhibiting PTEN expression conjugated with cholesterol, for use in treating a spinal cord injury. According to such embodiments, the siRNA has a nucleic acid sequence selected from SEQ ID NO: 10, 11, 2, 3, 4 and 5. According to one embodiment, the siRNA comprises sequences SEQ ID NO: 10 and SEQ ID NO: 11. According to some embodiments, the pharmaceutical composition is administered intransally. According to another embodiment, the pharmaceutical composition is administered intra-lesion. According to yet another embodiment, the pharmaceutical composition is orally administered.

According to any one of the above embodiment, the treating comprises co-administering of the pharmaceutical composition of the present invention with Chondroitinase ABC lyase.

In one embodiment, a polynucleotide encoding Chondroitinase ABC lyase is provided to the patient (i.e. via gene therapy). Expression constructs for expressing the Chondroitinase ABC lyase are further described herein below. The polynucleotide encoding Chondroitinase ABC lyase may be uploaded into the particles. In another embodiment, the enzyme per se is provided to the patient.

In a particular embodiment, both the PTEN inhibitor and the Chondroitinase ABC is co-formulated in the same particles. In another embodiment, the PTEN inhibitor and the Chondroitinase ABC are loaded in the same particle type (e.g. mesenchymal stem cell derived exosomes), but not the same particle itself. In still another embodiment, the PTEN inhibitor and the Chondroitinase ABC are loaded in different particle types (e.g. PTEN inhibitor is comprised in mesenchymal stem cell derived exosomes and Chondroitinase ABC is comprised in dental pulp derived exosomes, or vice versa).

According to some embodiments, the use further comprises co-administered with therapeutic agents useful in treating neurological disorders, such as gangliosides; antibiotics, neurotransmitters, neurohormones, toxins, neurite promoting molecules; and antimetabolites small molecule agents and precursors of neurotransmitter molecules such as L-DOPA, or with cells capable of alleviating at least one symptom of the neurological disease.

According to some embodiments the particles loaded with an exogenous phosphatase and tensin homolog (PTEN) inhibitor are liposomes, as defined hereinabove. Therefore, according to some embodiments, the present invention provides a pharmaceutical composition comprising exosomes loaded with an PTEN inhibitor, for use in treating a neurological disease, disorder or condition in a subject in need thereof. According to some embodiments, the condition is a spinal cord injury.

According to another aspect, the present invention provides a method of treating a neuronal injury, damage disease or disorder in a subject in need thereof, comprising administering to the subject a therapeutically effective amount of membrane vesicles loaded with an exogenous phosphatase and tensin homolog (PTEN) inhibitor, thereby treating the injury, damage disease or disorder. All the terms of the above embodiments and aspects apply here as well. According to some embodiments, the membrane vesicles are extracellular vesicles, as described hereinabove.

The membrane vesicles of the present invention can be administered to the treated individual using a variety of administration routes as defined hereinabove, including transplantation approaches, the nature of which depends on the site of implantation.

The term or phrase "transplantation", "cell replacement" or "grafting" injection are used interchangeably herein and refer to the introduction of the particles of the present invention to target tissue, such as the brain, the grey matter etc. The mesenchymal stem cells from where the particles are obtained can be derived from the recipient (allogeneic) or from a non-allogeneic or xenogeneic donor.

The membrane vesicles can be transplanted directly into the spinal cord (intrathecally), intravenously, directly into the brain or combinations of same such that it reaches the brain. In one embodiment, the particles are delivered non-invasively, e.g. intranasally. Other modes of administration are also contemplated such as systemic administration.

An exemplary dose of membrane vesicles (e.g. exosomes) that may be administered (e.g. intranasally) per treatment may be between $1\times10^6$-$1\times10^{20}$ and or between $1\times10^9$-$1\times10^{15}$ for a 70 kg human.

The term "therapeutically effective amount" of the membrane vesicles, when administered to a subject will have the intended therapeutic effect, e.g. treating neuronal injury such as SCI. The full therapeutic effect does not necessarily occur by administration of one dose, and may occur only after administration of a series of doses. Thus, a therapeutically effective amount may be administered in one or more administrations. The precise effective amount needed for a subject will depend upon, for example, the subject's size, health and age, the nature and extent of the cognitive impairment, and the therapeutics or combination of therapeutics selected for administration, and the mode of administration. The skilled person can readily determine the effective amount for a given situation by routine experimentation.

According to some embodiments, the membrane vesicles, such as EVs, are administered intranasal, intra-lesionally, parenterally, locally, systemically or orally.

Toxicity and therapeutic efficacy of the active ingredients described herein can be determined by standard pharmaceutical procedures in vitro, in cell cultures or experimental animals.

The data obtained from these in vitro and cell culture assays and animal studies can be used in formulating a range of dosage for use in human. Further information may be obtained from clinical studies—see for example Salem H K et al., Stem Cells 2010; 28:585-96; and Uccelli et al. Lancet Neurol. 2011; 10:649-56).

The dosage may vary depending upon the dosage form employed and the route of administration utilized. The exact formulation, route of administration and dosage can be chosen by the individual physician in view of the patient's condition.

For injection, the active ingredients of the pharmaceutical composition may be formulated in aqueous solutions, preferably in physiologically compatible buffers such as Hank's solution, Ringer's solution, or physiological salt buffer and additional agents as described herein above.

Dosage amount and interval may be adjusted individually to levels of the active ingredient which are sufficient to effectively treat the neurological disorder. Dosages necessary to achieve the desired effect will depend on individual characteristics and route of administration.

Depending on the severity and responsiveness of the condition to be treated, dosing of particles can be of a single or a plurality of administrations, with course of treatment lasting from several days to several weeks or months depending when diminution of the disease state is achieved.

The amount of particles to be administered will, of course, be dependent on the individual being treated, the severity of the affliction, the manner of administration, the judgment of the prescribing physician, etc. The dosage and timing of administration will be responsive to a careful and continuous monitoring of the individual changing condition.

Following administration, the particles may be tracked in order to ensure they have reached the target site. This may be carried out using gold nanoparticle for instance—see WO 2013/186735 A3.

According to some embodiments, the present invention provides extracellular vesicles loaded with an exogenous phosphatase and tensin homolog (PTEN) inhibitor for use in preparation of a medicament for use in treating a neurological disease, disorder or condition in a subject in need thereof. According to some embodiments, the extracellular vesicles are isolated extracellular vesicles. According to one embodiment, the neurological condition is a spinal cord injury.

According to another aspect, the present invention provides lipid bilayer phospholipid membrane vesicles loaded with an exogenous phosphatase and tensin homolog (PTEN) inhibitor. According to some embodiments, the membrane vesicles are isolated extracellular vesicles.

Thus, according to some embodiments, the present invention provides extracellular vesicles loaded with an exogenous phosphatase and tensin homolog (PTEN) inhibitor, wherein the extracellular vesicles are derived from cells. According to one embodiment, the extracellular vesicles are selected from extracellular vesicles, liposomes, ectosomes, and transferosomes.

According to one embodiment, the extracellular vesicles are selected from exosomes, microvesicles and a combination thereof. According to one embodiment, the EVs are exosomes. According to one embodiment, the EVs are microvesicles. According to one embodiment, the microvesicles have a diameter of from 100 to 1000 nm, from 120 to 800 nm, from 150 to 600 nm from 200 to 400 nm. According to another embodiment, the microvesicles have a size of 100 to 300 nm or 150 to 250 nm. According to some embodiments, the EVs have a diameter to 30 to 250 nm or from 50 to 200 nm. According to some embodiments, the EVs have a diameter to 70 to 170 nm or from 80 to 150 nm.

According to any one of the above embodiments, the EVs are derived from cells. According to one embodiment, the EVs, e.g. exosomes, are derived from cells expressing mesenchymal markers. According to one embodiment, the cells are adherent cells. According to some embodiment, the cells are selected from mesenchymal stem cells, oral mucosa stem cells and olfactory ensheathing cells. According to some embodiments, the cells are mesenchymal stem cells (MSC). According to one embodiment, the mesenchymal stem cells are originated from a site selected from bone marrow, adipose tissue, umbilical cord, dental pulp, oral mucosa, peripheral blood and amniotic fluid. According to some embodiments, the EVs are derived from bone marrow originated MSC. According to other embodiment, the EVs are derived from the adipose tissue originated MSC. According to some such embodiments, the EVs are selected from exosomes, microvesicles and a combination thereof. According to some embodiments, the cells express CD105, CD166, CD29, CD90, and CD73 markers. According a further embodiment, the cells express CD105, CD166, CD29, CD90, and CD73, and do not express CD34, CD45 and CD133. According to some embodiments, the cells are selected from dental pulp stem cells (DPSCs), exfoliated deciduous teeth stem cells (SHED), periodontal ligament stem cells (PDLSCs), apical papilla stem cells (SCAP) and dental follicle progenitor cells (DFPCs).

The EVs may have at least one property of a mesenchymal stem cell. The particle may have a biological property, such as a biological activity. The particle may have any of the biological activities of an MSC. The particle may for example have a therapeutic or restorative activity of an MSC.

According to some embodiments, the EVs are derived from cells expressing markers from neural crest cells (NCC). According to one embodiment, the cells are neural crest cells. According some embodiments, the neural crest cells are cranial neural crest cells. According to one embodiment, the cranial neural crest cells are selected from dental pulp stem cells (DPSCs), exfoliated deciduous teeth stem cells (SHED), periodontal ligament stem cells (PDLSCs), apical papilla stem cells (SCAP) and dental follicle progenitor cells (DFPCs). According to another embodiment, the cells express mesenchymal markers, as defined above.

According to any one of the above embodiments, the EVs are isolated from the cells. Therefore according to some embodiments, the EVs are isolated EVs, e.g. isolated exosomes and/or isolated microvesicles. According to one embodiment, the ratio of EVs to residual parent cells is at least 2, 3, 4, 5, 6, 8 or 10 times higher, or in certain advantageous embodiments at least 50 100 or, 1000 times higher than in the initial material. According to some embodiments, the EVs are cell-free EVs.

The EVs may be produced or isolated in a number of ways. Such a method may comprise isolating the EVs from mesenchymal stem cells (MSC) or from neural crest cells (NCC). According to some embodiment, the isolated extracellular vesicles are cell-free.

According to any one of the above embodiments, the extracellular vesicles comprise PTEN inhibitor, as defined in any one of the above aspects and embodiments. According to one embodiment, the extracellular vesicles are loaded with PTEN inhibitor. According to one embodiments, the isolated extracellular vesicles are loaded with said PTEN inhibitor. According to one embodiment, the PTEN inhibitor inhibits or downregulates PTEN activity. According to another embodiment, the PTEN inhibitor inhibits or downregulates PTEN expression.

According to a one embodiment, the exogenous PTEN inhibitor is a protein or peptide. According to another embodiment, the exogenous PTEN inhibitor is a small molecule. According to some embodiments, the exogenous PTEN inhibitor PTEN inhibitor is an inhibitor of PTEN expression. According to one embodiment, the exogenous inhibitor of PTEN expression is a polynucleotide agent or an oligonucleotide agent. According to another embodiment, the exogenous PTEN inhibitor is an RNA interference oligonucleotide. According to one embodiment, the RNA interference oligonucleotide is an siRNA. According to another embodiment, the RNA interference oligonucleotide is an shRNA. According to one embodiment, the PTEN inhibitor is an siRNA. According to one embodiment, the siRNA has a nucleic acid sequence selected from SEQ ID NO: 10, 11, 2, 3, 4 and 5. According to one embodiment, the PTEN inhibitor is an siRNA having sequence SEQ ID NO: 10. According to another embodiment, the PTEN inhibitor is a double stranded siRNA comprising sequence SEQ ID NO: 10 and SEQ ID NO: 11. According to one embodiment, the siRNA comprises a sequence complementary to a fragment of a nucleic acid encoding PTEN protein and inhibits its expression. According to one embodiment, the siRNA comprises a sequence complementary to a fragment of a nucleic acid encoding SEQ ID NO:1. Thus, according to one embodiment, the extracellular vesicles are loaded with siRNA having a nucleic acid sequence SEQ ID NO: 2 and 3 or SEQ ID NO: 4 and 5. According to certain embodiments, the isolated extracellular vesicles are loaded with siRNA having a nucleic acid sequences SEQ ID NO: 10 and 11. According to one embodiment, the siRNA comprises a sequence being a variant of a nucleic acid sequence selected from SEQ ID NO: 10, 11, 2, 3, 4 and 5, and having at least 80% sequence identity to the original sequence. According to another embodiment, the isolated extracellular vesicles are loaded with shRNA comprising a nucleic acid sequence from SEQ ID NO: 10 and 11. According to one embodiment, the shRNA comprises nucleic acid sequences SEQ ID NO: 2 and 3. According to another embodiment, the shRNA comprises nucleic acid sequences SEQ ID NO: 4 and 5. According to a further embodiment, the siRNA comprises nucleic acid complementary to sequences SEQ ID NO: 6 or 7. According to yet another embodiment, the shRNA comprises a sequence selected from SEQ ID NO: 8 and 9. According to some embodiment, the oligonucleotide inhibitor, e.g. siRNA or shRNA comprises a hydrophobic moiety. According to some embodiments, the hydrophobic moiety is a sterol, a ganglioside, a lipid, a vitamin, a fatty acid, a peptide, or a combination thereof. According to one embodiment, the sterol is cholesterol.

According to one specific embodiment, the present invention provides isolated exosomes derived from mesenchymal stem cells loaded with siRNA molecules inhibiting PTEN expression. According to one embodiment, the siRNA comprises, e.g. conjugated with, a cholesterol moiety. According to one embodiment, the siRNA comprises a nucleic acid sequence selected from SEQ ID NO: 10, 11, 2, 3, 4 and 5 and is conjugated with cholesterol. According to another embodiment, the siRNA comprises nucleic acid sequences SEQ ID NO: 10 and 11. According to some embodiments, the siRNA comprises a nucleic acid sequence targeting SEQ ID NO:6 and conjugated with cholesterol. According to other embodiments, the siRNA comprises a nucleic acid sequence targeting SEQ ID NO:7 and conjugated with cholesterol.

According to some embodiments, the isolated extracellular vesicles loaded with an exogenous phosphatase and tensin homolog (PTEN) inhibitor are useful for treating neurological disease, disorder, damage or condition. According to one embodiment, the neurological condition is spinal cord injury. Thus, according to one embodiment the present invention provides extracellular vesicles, for use in treating spinal cord injury, wherein said membrane vesicles are loaded with an exogeneous phosphatase and tensin homolog (PTEN) inhibitor. According to a particular embodiment, the neurological disease is a degenerative disease of the nervous system. According to one embodiment, the degenerative disease of the nervous system is selected from as Parkinson's disease, essential tremor, Huntington's disease, Alzheimer's disease, multiple sclerosis, ALS and organic psychosis. According to one embodiment, the disease is a memory disease. In one embodiment, the disease is a neurodevelopmental disorder such as autism or schizophrenia. According to another embodiment, the disease is a behavioral disease such as schizophrenia, attention deficit hyperactivity disorder, autism, Tourette's syndrome, obsessive compulsive disorder, as well as the neurobehavioral associated symptoms.

According to some embodiments, the extracellular vesicles further comprise chondroitinase ABC or a polynucleotide encoding same. According another embodiment, the EVs loaded with PTEN inhibitor further comprise chondroitinase ABC or a polynucleotide encoding same.

According to some embodiment, the present invention provides a pharmaceutical composition comprising the isolated extracellular vesicles according to any one of above embodiments. According to some embodiments, the pharmaceutical composition is for use in treating neurological disease, disorder, damage or condition. According to one embodiment, the pharmaceutical composition is for use in treating spinal cord injury.

According to some embodiments, membrane vesicles are liposomes. According to one embodiment, the liposomes are SUVs. According to other embodiment, the liposomes are MLVs. According to one embodiment, the liposomes comprise a liposome forming lipid selected from the group consisting of a phosphatidylcholine, phosphatidylinositol, phosphatidylglycerol, phosphatidylethanolamine, 1-palmitoyl-2-oleoylphosphatidyl choline (POPC), sphingophospholipids, distearoyl, and any combination thereof. According to another embodiment, the liposome forming lipid is phosphatidylcholine. According to one embodiment, the phosphatidylcholine is hydrogenated soy phosphatidylcholine (HSPC). According to other embodiments, the phosphatidylethanol amine is 1,2-di stearoyl-sn-glycero-3-phosphoethanolamine (DSPE), and said distearoyl is distearoyl glycol (DSG) or oxycarbonyl-3-amino-1,2-propanediol distearoylester (DS). According to another embodiment, the liposomes comprise stabilizing polymer molecule such as polyalkylether, polysialic acid, polylactic acid and polyglycolic acid. According to one embodiment, the liposomes comprise PEG. According to some embodiments, the liposomes further comprise cholesterol.

According to another aspect, the present invention provides a method of preparation of extracellular vesicles loaded with an exogenous PTEN inhibitor, of the present invention. According to some embodiments, the extracellular vesicles are exosomes. According to another embodiment, the EVs are microvesicles. According to a further embodiment, the EVs is a combination of microvesicles and exosomes. The exosomes and the microvesicles are as defined in any one of the above embodiments and aspects. According to some embodiments, the EVs are derived from cells expressing mesenchymal markers. According to one embodiment, the cells expressing mesenchymal markers are selected from mesenchymal stem cells, oral mucosa stem cells and olfactory ensheathing cells. According to another embodiment, the EVs are derived from neural crest cells, e.g. from cranial neural crest cells.

According to one embodiment, the EVs, such as exosomes, are derived from mesenchymal stem cells. According to some embodiments, the MSC are isolated from a tissue selected from bone marrow, adipose tissue, dental pulp, oral mucosa, peripheral blood and amniotic fluid. According to some embodiments, the mesenchymal stem cells typically express the following markers: CD105, CD166, CD29, CD90, and CD73, and do not express CD34, CD45 and CD133.

The method may comprise isolating the EVs from a mesenchymal stem cells conditioned medium (MSC-CM) or from a neural crest cells conditioned medium (NCC-CM). The EVs may be isolated for example by being separated from non-associated components based on any property of the EVs. For example, the EVs may be isolated based on molecular weight, size, shape, composition or biological activity.

The conditioned medium may be filtered or concentrated or both during, prior to or subsequent to separation. For example, it may be filtered through a membrane, for example one with a size or molecular weight cut-off. It may be subject to tangential force filtration or ultrafiltration.

For example, filtration with a membrane of a suitable molecular weight or size cutoff, as described in the Assays for Molecular Weight elsewhere in this document, may be used.

The conditioned medium, optionally filtered or concentrated or both, may be subject to further separation means, such as column chromatography. For example, high performance liquid chromatography (HPLC) with various columns may be used. The columns may be size exclusion columns or binding columns.

One or more properties or biological activities of the particle may be used to track its activity during fractionation of the cell conditioned medium. As an example, light scattering, refractive index, dynamic light scattering or UV-visible detectors may be used to follow the particles. For example, a therapeutic activity such as cardioprotective activity may be used to track the activity during fractionation.

The following paragraphs provide a specific non-limiting example of how a mesenchymal stem cell EVs such as an exosome may be obtained.

A mesenchymal stem cell EVs may be produced by culturing mesenchymal stem cells in a medium to condition it. The medium may comprise DMEM. The DMEM may be such that it does not comprise phenol red. The medium may be supplemented with insulin, transferrin, or selenoprotein (ITS), or any combination thereof. It may comprise FGF2. It may comprise PDGF AB. The concentration of FGF2 may be about 5 ng/ml FGF2. The concentration of PDGF AB may be about 5 ng/ml. The medium may comprise glutamine-penicillin-streptomycin or -mercaptoethanol, or any combination thereof.

The cells may be cultured for about 1, 2, 3, 4, 5, 6, 7, 8, 9, 10 days or more, for example 3 days. The conditioned medium may be obtained by separating the cells from the medium. The conditioned medium may be centrifuged, for example at 500 g. it may be concentrated by filtration through a membrane. The membrane may comprise a >1000 kDa membrane. The conditioned medium may be concentrated about 50 times or more.

The conditioned medium may be subject to liquid chromatography such as HPLC. The conditioned medium may be separated by size exclusion. Any size exclusion matrix such as Sepharose may be used. As an example, a TSK Guard column SWXL, 6×40 mm or a TSK gel G4000 SWXL, 7.8×300 mm may be employed. The eluent buffer may comprise any physiological medium such as saline. It may comprise 20 mM phosphate buffer with 150 mM of NaCl at pH 7.2. The chromatography system may be equilibrated at a flow rate of 0.5 ml/min. The elution mode may be isocratic. UV absorbance at 220 nm may be used to track the progress of elution. Fractions may be examined for dynamic light scattering (DLS) using a quasi-elastic light scattering (QELS) detector.

Fractions which are found to exhibit dynamic light scattering may be retained. For example, a fraction which is produced by the general method as described above, and which elutes with a retention time of 11-13 minutes, such as 12 minutes, is found to exhibit dynamic light scattering. The $r_h$ of particles in this peak is about 45-55 nm. Such fractions comprise mesenchymal stem cell EVs such as exosomes.

According to one embodiment, the exogenous PTEN inhibitor is an inhibitor of PTEN expression. According to one embodiment, the exogenous PTEN is an RNA interference oligonucleotide. According to one embodiment, the RNA interference oligonucleotide is an siRNA. According to another embodiment, the RNA interference oligonucleotide is an shRNA. According to some embodiments, the RNAi oligonucleotide is conjugated with a hydrophobic moiety. According to one embodiment, the hydrophobic moiety is selected from a sterol, a ganglioside, a lipid, a vitamin, a fatty acid, a peptide, and a combination thereof. According to some embodiments, the RNA interference oligonucleotide is conjugated with cholesterol. Thus, in one embodiment, the RNAi, e.g. siRNA, is conjugated with cholesterol.

It will be appreciated that polynucleotides or oligonucleotides such as siRNA or shRNA may also be loaded directly into the EVs. In one embodiment, direct loading of RNAi oligonucleotide to the EVs is carried out by electroporation and/or with the use of transfection agents. In alternative embodiments, the loading is carried out in the absence of electroporation and/or in the absence of transfection agents.

According to one embodiment, the EVs are incubated with the RNAi oligonucleotide inhibitor for a period of time sufficient to permit loading of the particles with the nucleic acid based inhibitor. The duration of time sufficient to permit loading of the EVs with the nucleic acid based inhibitor cargo can be optimized for the particular type of cargo and if modified to comprise a hydrophobic modification, then the type of modification. Generally, an incubation of about 1 hour or less is sufficient to permit efficient loading of particles with nucleic acid cargo. In many instances, hydrophobically modified cargo is efficiently loaded into exosomes in a very rapid period of time, for example, within 5 minutes. Accordingly, in some embodiments, efficient loading takes place during an incubation period of 5 minutes or less, e.g., from 1-5 minutes. In exemplary embodiments, efficient loading takes place during an incubation period of 5 minutes, 10 minutes, 15 minutes, 20 minutes, 30 minutes, etc. In other embodiments, efficient loading may take place within 1 hour, within 2 hours, within 3 hours, within 4 hours, within 5 hours, within 6 hours, within 7 hours, within 8 hours, within 9 hours, within 10 hours, within 12 hours, within 24 hours, etc.

Loading of EVs with oligonucleotides is not highly temperature dependent. In exemplary embodiments, exosomes are loaded at or around 37 degree C. In other embodiments, EVs (e.g. exosomes) can be loaded at or around room temperature. In other embodiments, exosomes can be loaded at or around 4 degree C.

According to some embodiments, the EVs can be loaded without the use of ultracentrifugation. According to other embodiment, the loading further comprises ultracentrifugation. According to some embodiment, the method of preparation further comprises a step of purification or isolation of the loaded EVs. According to one embodiment, the isolations is effected by centrifugation, e.g. ultracentrifugation. According to another embodiment, the isolations is effected via filtration. According to one embodiment, the ratio of EVs to residual parent cells following purification is at least 2, 3, 4, 5, 6, 8 or 10 times higher, or in certain advantageous embodiments at least 50, 100 or, 1000 times higher than in the initial material. According to some embodiment, the EVs are cell-free EVs.

According to some embodiments, the present invention provides a method of preparation of EVs, e.g. exosomes, the method comprises incubating EVs with cholesterol-conjugated RNAi oligonucleotides such as siRNA or shRNA for 0.5 to 5 hours at a temperature of 25 to 42° C.

According to one embodiment, the method further comprises a step of isolation of the loaded EVs using centrifugation, e.g. ultracentrifugation. According to some embodiments, another hydrophobic moiety may be used instead of cholesterol. According to one embodiment, the RNAi oligonucleotide is siRNA. According to one embodiment, the siRNA comprises nucleic acid sequence SEQ ID NO: 2. According to another embodiment, the siRNA comprises nucleic acid sequence SEQ ID NO: 3. According to a certain embodiment, the siRNA comprises nucleic acid sequence SEQ ID NO: 4. According to another embodiment, the siRNA comprises nucleic acid sequence SEQ ID NO: 5. According to some embodiments, the siRNA comprises nucleic acid sequence SEQ ID NO: 10. According to other embodiments, the siRNA comprises nucleic acid sequence SEQ ID NO: 11. According to a further embodiment, the siRNA is complementary to nucleic acid sequence SEQ ID NO: 6. According to one embodiment, the siRNA targets nucleic acid sequence SEQ ID NO: 6. According to some embodiments, the RNAi oligonucleotide is shRNA. According to one embodiment, the siRNA or shRNA comprises nucleic acid sequences SEQ ID NO: 2 and 3. According to another embodiment, the siRNA or shRNA comprises nucleic acid sequences SEQ ID NO: 4 and 5. According to a further embodiment, the siRNA or shRNA comprises nucleic acid sequences SEQ ID NO: 10 and 11. According to a further embodiment, the shRNA comprises nucleic acid sequences commentary to SEQ ID NO: 6 or 7. According to yet another embodiment, the shRNA comprises a sequence selected from SEQ ID NO: 8 and 9. According to some embodiments, the shRNA or the siRNA comprises a sequence complementary to a fragment of a nucleic acid encoding PTEN protein and inhibits its expression. According to one embodiment, the PTEN comprises amino acid SEQ ID NO:1.

In some embodiments, over 50% of hydrophobically modified oligonucleotide cargo is loaded to exosomes using the methods described herein. Accordingly, in some embodiments, hydrophobically modified oligonucleotide cargo is loaded to exosomes with an efficiency of from 5 to 40%. Accordingly, in one embodiment, hydrophobically modified oligonucleotide cargo is loaded to exosomes with an efficiency of from 10 to 35%, from 15 to 30% or from 20 to 25%. For example, hydrophobically modified oligonucleotide cargo is loaded to exosomes with an efficiency of 5% or greater, 10% or greater, 15% or greater, 20% or greater, 25% or greater, 30% or greater, 35% or greater, 40% or greater, or 50% or greater. The methods described herein result in the incorporation of hydrophobically modified oligonucleotide into all or nearly all of the exosomes that are treated. For example, at least 80% of the exosomes incubated with hydrophobically modified oligonucleotide are loaded with the oligonucleotide. In some embodiments, hydrophobically modified oligonucleotide cargo is incorporated in at least 90% of the exosomes incubated with the oligonucleotide. Thus, populations of exosomes in which at least 80%, at least 90%, at least 91%, at least 92%, at least 93%, at least 94%, at least 95%, at least 96%, at least 97%, at least 98% or more of the exosomes are loaded with the oligonucleotide cargo can be readily obtained. In one embodiment at least 99% of the exosomes are loaded with the hydrophobically modified oligonucleotide.

EVs (e.g. exosomes) can be loaded with over 500 oligonucleotide molecules per particle (e.g. exosome), e.g., at least 500, at least 600, at least 700, at least 800, at least 900, at least 1000, at least 1200, at least 1500, at least 2000, at least 2500, at least 3000 or more oligonucleotides per exosome. In one embodiment, the exosomes contain an average of about 500-3000 oligonucleotides per exosome. In another embodiment, exosomes contain an average of about 500-1000 oligonucleotides per exosome. In another embodiment, exosomes contain an average of about 1000-1500 oligonucleotides per exosome. In another embodiment, exosomes contain an average of about 1000-2000 oligonucleotides per exosome. In another embodiment, exosomes contain an average of about 1000-3000 oligonucleotides per exosome. In another embodiment, exosomes contain up to about 3000 oligonucleotides per exosome. The quantities of hydrophobically modified oligonucleotide cargo that can be loaded into exosomes allow the production of exosomes in which the hydrophobically modified oligonucleotide cargo occupies a significant proportion of the exosomal membrane. For example, EVs (e.g. exosomes) can be produced in which oligonucleotide cargo occupies about 1-10% of the surface area of the particle, e.g., about 1%, 2%, 3%, 4%, 5%, 6%, 7%, 8%, 9%, or 10% of the surface area of the particle. According to some embodiment, the oligonucleotide cargo is RNAi oligonucleotide, such as siRNA or shRNA. According to other embodiments, the hydrophobically modified oligonucleotide is a RNAi oligonucleotide conjugated with a hydrophobic moiety, e.g. with cholesterol moiety.

According to some embodiments, the lipid bilayer phospholipid membrane vesicles are liposomes. According to such embodiments, the liposomes are loaded in the same method as described for EVs.

According to other embodiment, the EVs loaded with PTEN RNAi inhibitor may be obtained from cells artificially loaded with a RNAi oligonucleotide or with a polynucleotide encoding and capable of expressing or generating said RNAi inhibitor within a cell. In this case, the polynucleotide/oligonucleotide agent is ligated in a nucleic acid construct under the control of a cis-acting regulatory element (e.g. promoter) capable of directing an expression of the agent in a constitutive or inducible manner.

The nucleic acid agent may be delivered using an appropriate gene delivery vehicle/method (transfection, transduction, etc.). Optionally an appropriate expression system is used. Examples of suitable constructs include, but are not limited to, pcDNA3, pcDNA3.1 (+/−), pGL3, PzeoSV2 (+/−), pDisplay, pEF/myc/cyto, pCMV/myc/cyto each of which is commercially available from Invitrogen Co.

The expression construct may also be a virus. Examples of viral constructs include but are not limited to adenoviral vectors, retroviral vectors, vaccinia viral vectors, adeno-associated viral vectors, polyoma viral vectors, alphaviral vectors, rhabdoviral vectors, lentiviral vectors and herpes-viral vectors.

A viral construct such as a retroviral construct includes at least one transcriptional promoter/enhancer or locus-defining element(s), or other elements that control gene expression by other means such as alternate splicing, nuclear RNA export, or post-transcriptional modification of messenger. Such vector constructs also include a packaging signal, long terminal repeats (LTRs) or portions thereof, and positive and negative strand primer binding sites appropriate to the virus used, unless it is already present in the viral construct. In addition, such a construct typically includes a signal sequence for secretion of the peptide from a host cell in which it is placed. Preferably, the signal sequence for this purpose is a mammalian signal sequence or the signal sequence of the peptide variants of the present invention. Optionally, the construct may also include a signal that directs polyadenylation, as well as one or more restriction site and a translation termination sequence. By way of example, such constructs will typically include a 5' LTR, a tRNA binding site, a packaging signal, an origin of second-strand DNA synthesis, and a 3' LTR or a portion thereof.

Preferably the viral dose for infection is at least $10^3$, $10^4$, $10^5$, $10^6$, $10^7$, $10^8$, $10^9$, $10^{10}$, $10^{11}$, $10^{12}$, $10^{13}$, $10^{14}$, $10^{15}$ or higher pfu or viral particles.

Double stranded RNA may be synthesized by adding two opposing promoters to the ends of the gene segments, wherein one promoter is placed immediately 5' to the gene and the opposing promoter is placed immediately 3' to the gene segment. The dsRNA may then be transcribed with the appropriate polymerase.

In another embodiment, polynucleotide or oligonucleotide agents can be incubated with cells in culture, resulting in efficient uptake of the nucleic acid by cells. For such an embodiment, preferably the nucleic acid agents are hydrophobically modified, as further described herein below.

Irrespective of the method used to load the particles with the nucleic acid agents described herein, the cells are then incubated for a period of time sufficient for EVs, e.g. exosome, production. Exosomes isolated from the culture media contain exosomes loaded with the nucleic acid molecule taken up, produced or expressed by the cells. Accordingly, in one embodiment, a method of loading EVs with oligonucleotide cargo is provided, comprising incubating cells capable of EVs production (e.g. exosome production) with an oligonucleotide for a period of time sufficient for the oligonucleotide to be internalized by the cells, culturing the cells for a period of time sufficient for exosome secretion, and isolating exosomes loaded with the oligonucleotide from the culture medium.

According to some embodiments, the present invention provide isolated extracellular vesicles prepared according to any one of the above embodiments. According to another embodiment, the present invention provides a pharmaceutical composition comprising extracellular vesicles prepared according to any one of the above embodiments. According to some embodiments, such isolated extracellular vesicles and pharmaceutical compositions are useful in treating neurological diseases or conditions such as spinal cord injury.

The particles or the pharmaceutical composition of the present invention, in at least some embodiments, may be prepackaged in unit dosage forms in a syringe ready for use. The syringe may be labeled with the name of the particles and their source. The labeling may also comprise information related to the function of the particles. The syringe may be packaged in a packaging which is also labeled with information regarding the particles.

The terms "comprising", "comprise(s)", "include(s)", "having", "has" and "contain(s)," are used herein interchangeably and have the meaning of "consisting at least in part of". When interpreting each statement in this specification that includes the term "comprising", features other than that or those prefaced by the term may also be present. Related terms such as "comprise" and "comprises" are to be interpreted in the same manner. The terms "have", "has", having" and "comprising" may also encompass the meaning of "consisting of" and "consisting essentially of", and may be substituted by these terms. The term "consisting of" excludes any component, step or procedure not specifically delineated or listed. The term "consisting essentially of" means that the composition or component may include additional ingredients, but only if the additional ingredients do not materially alter the basic and novel characteristics of the claimed compositions or methods.

As used herein, the term "about", when referring to a measurable value such as an amount, a temporal duration, and the like, is meant to encompass variations of +/−10%, or +/−5%, +/−1%, or even +/−0.1% from the specified value.

As used herein, the singular form "a", "an" and "the" include plural references unless the context clearly dictates otherwise. For example, the term "a compound" or "at least one compound" may include a plurality of compounds, including mixtures thereof.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Various embodiments and aspects of the present invention as delineated hereinabove and as claimed in the claims section below find experimental support in the following examples.

According to another aspect of the present invention provided exosomes derived from a neural crest cell for use in treating a spinal cord injury.

EXAMPLES

Reference is now made to the following examples, which together with the above descriptions illustrate some embodiments of the invention in a non-limiting fashion.

Generally, the nomenclature used herein and the laboratory procedures utilized in the present invention include molecular, biochemical, microbiological and recombinant DNA techniques. Such techniques are thoroughly explained in the literature.

Materials and Methods
Mesenchymal Stem Cell Preparation

Bone marrow derived human MSCs were purchased from Lonza (Basel, Switzerland). Cells were cultured and expanded as previously described. Prior to exosome collection, the cells were cultured in exosome-free platelets, and 3 days later, the medium was collected. MSC-exo where labeled with PKH26 (Sigma) for 5 minutes and were washed using ultracentrifugation (100,000 g, 2 hours, 4° C.). Pellet was re-suspended with 200 µl PBS.

Exosome Purification Protocol

Human MSCs were purchased from Lonza (Basel, Switzerland). Cells were cultured and expanded. Cells were cultured with exosome-free platelets lysate (Rabin Medical Center, Israel), and 3 days later, the medium was collected. The exosomes were purified using a standard differential centrifugation protocol, which involved isolating the culture fluid and centrifuging for 10 min at 300 g. The supernatant was recovered and centrifuged for 10 min at 2,000 g and then re-centrifuged for 30 min at 10,000 g. The supernatant was then passed through a 0.22 µm filter, and centrifuged for 70 min at 100,000 g. The pellet, containing the exosomes and proteins, was washed in PBS and then centrifuged for 70 min at 100,000 g. The pellet was re-suspended in 200 µl sterile PBS. All centrifugations were performed at 4° C. Exosomes were characterized using NanoSight technology, electron microscopy and Western blotting for calnexin, as a negative marker, and CD9 and CD81, as positive marker.

Mesenchymal Stem Cells Exosomes (MSC-Exo) Fluorescent Labeling

MSC-Exo were labeled with PKH26/PKH67 (Sigma) for 5 min and then washed with PBS using ultracentrifugation (100,000 g, 2 h, 4° C.). Pellets were re-suspended in 200 µl PBS. For PTX experiments, MSC-Exo were suspended with 5 µl PTX for 10 min at 37° C., then labeled with PKH26 and centrifuged at 100,000 g for 2 h. MSC-Exo+PKH67 and MSC-Exo+PTX+PKH26 were administered together to the same rat (n=3).

Gold Nanoparticle (GNP) Synthesis and Conjugation

A mixture of 3.75 ml linoleic acid (18%), oleic acid (65%), palmitic acid (16%) and ethanol (1%), 200 mg NaOH and 15 ml of ethanol, was added to 30 ml DDW. The solution was stirred for 5 min. Fifty milligrams of $HAuCl_4$ were then added while stirring, followed by 5 ml ascorbic acid (0.05 M), and another minute of stirring. PEG7 solution ($2.26 \times 10^{-3}$ g) was then added to the GNP solution, and the mixture was stirred for 1 h. The pH was then adjusted to 9 using NaOH, and the solution was stirred for an additional hour. After adding 80 ml n-hexane, the solution was stirred for 1 h. The pH of the resulting mixture was then adjusted to 7, using HCl solution (37%). The mixture was placed in a funnel for phase separation (organic and aqueous). The aqueous phase was evaporated using a vacuum. Next, excess carbodiimide ($1.87 \times 10^{-3}$ g) and N-hydroxysuccinimide (Thermo Fisher Scientific, Inc., Rockford, Ill.) ($2.12 \times 10^{-3}$ g) were added to the solution, followed by addition of 2GF (Sigma-Aldrich, Israel Ltd.) ($1.75 \times 10^{-3}$ g). A total of $2.8 \times 10^{10}$ exosomes (200 µl exosomes in 1 ml saline) were incubated at 37° C. for 3 h with glucose-coated GNPs (35 mg/mL, 100 µl). The exosomes were then centrifuged for 2 h (100,000 g, 4° C.).

GNP Characterization

Transmission electron microscopy (JEM-1400, JEOL) was used to measure the size and shape of the GNPs, which were further characterized using ultraviolet-visible spectroscopy (UV-1650 PC; Shimadzu Corporation, Kyoto, Japan), ζ-potential (ZetaSizer 3000HS; Malvern Instruments, Malvern, UK), and dynamic light scattering.

GNP Quantifications

Flame Atomic absorption spectroscopy (SpectrAA 140; Agilent Technologies, Santa Clara, Calif.) was used to determine the amount of gold in several major organs (heart, lungs, lungs, kidneys and spleen). Dissected tissues were melted with 1 ml aqua regia acid (a 1:3 mixture of nitric acid and hydrochloric acid), which was allowed to evaporate, and then diluted to a total volume of 4 ml. After filtration of the samples through 0.45 nm syringe filters, gold concentrations were determined using a calibration curves prepared using a solution with known gold concentrations. Inductively coupled plasma spectrometry (ICP) was used to determine amounts of gold in the brains and spinal cord lesions. Tissues were freshly extracted and combusted at 550° C. for 5 h. 5 ml 1% $HNO_3$ were then added to the melted tissues and filtered through 0.45 μm filters. The gold concentrations in the samples were determined with correlation to the gold standard curve.

Exosome Loading

Exosomes (40 μl about $10^{10}$ exosomes) were loaded with 0.1 nmol cy3-MAPK-siRNA (Advirna Company) in an EPPENDORF® tube, and incubated for 1-3 hour at 37° C. Then, the suspension was subjected to Nanosight analysis. The concentration ratio of the fluorescent versus non-fluorescent exosomes was defined as loading efficiency.

For in vivo experiments, 40 μl exosomes were loaded with 0.1 nmol PTEN-siRNA (Advirna Company), for 2-3 h at 37° C., before being intranasally administered to SCI rats. Exosomes loaded with PTEN-siRNA are referred as ExoPTEN.

Axonal Outgrowth on Dorsal Root Ganglia (DRG) Neurons

Dorsal root ganglia at the thoracic and lumbar levels from adult Sprague-Dawley rats (200-250 g) were dissected and immersed in ice-cold Hank's Balanced Salt Solution (HBSS). DRGs were washed with HBSS, transferred to a small dish containing 4 ml of 2.5 mg/ml collagenase type II (Worthington), dissected into small pieces using a surgical blade, and incubated at 37° C., for 40 min. The solution was centrifuged at 200 g, 3 min to remove collagenase, resuspended in 2 ml of culture media, containing F12 culture medium (Gibco, 11765), 10% fetal bovine serum (Gibco), 100 U/ml penicillin (Biological Industries, Beit-Haemek, Israel), 100 ug/ml streptomycin, by triturating ~20 times via 1 ml pipet tips. Cells were plated per 15 mm coverslip precoated with laminin (Sigma, L2020) within in a 12-well plate at a density of $5\times10^4$ per well for 5 hours. The DRG medium was then replaced with that containing regular DRG medium, 40 μl exosomes, 0.1 nmol Non-targeting control (NTC) siRNA, 0.1 nmol PTEN siRNA, or 0.1 nmol PTEN siRNA loaded in 40 μl exosomes.

The sequence of PTEN that was targeted with the siRNAs is as set forth in SEQ ID NO: 6 (5'-GAGTTCTTC-CACAAACAGAA-3'). A double stranded siRNA comprising one strand comprising nucleic sequence 5'-GAGUUC-UUCCACAAACAGAA-3' (SEQ ID NO:10) conjugated with cholesterol and nucleic sequence 5'-UUCUGUUU-GUGGAAGAACUC-3' (SEQ ID NO: 11) was used to inhibit PTEN expression.

24 hour post-plating, the cells were fixed for 10 min with 4% paraformaldehyde (PFA), washed three times for 5 min with PBS, permeabilized for 10 min in 0.3% Triton X-100, washed three times for 5 min with PBS, blocked for 2 h in 5% bovine serum, and incubated overnight with mouse-anti-Tubulin (Promega, 1:500) in 5% bovine serum at 4° C. Next, samples were incubated with donkey-anti-mouse Alexa488 (Invitrogen, 1:800) and DAPI (1:1000) for 3 h. After three washes with PBS, samples were mounted and observed under confocal microscopy (LSM700). Images were processed using IMARIS software (Version 8.20), to quantify neurite branch level, maximum branch level, number of neurites, total neurite length. The parameters were set as followed and applied for every image: Largest diameter 60 μm, thinnest diameter 0.6 μm, starting point threshold 10 μm to 60 μm, seed point threshold 10 μm, remove seed points around starting points with diameter of sphere region 24 μm, maximum gap length allowed to be 60 μm.

Ex-Vivo CT Scans of Brain and Spinal Cord:

Brain and spinal cord samples were removed and placed in 4% paraformaldehyde for 3 days of fixation, then soaked in nonionic iodinated contrast agent (Iopamidol, Bayer Schering Pharma, Japan) of 150 mg/mL diluted with 7.5% paraformaldehyde at 4° C. for 7 days in order to differentiate between different gray and white matters. Prior to CT imaging, samples were removed from the solution, blotted dry, and placed in a sample holder for imaging. The sample holder was sealed with plastic film to prevent dehydration. Ex-vivo micro-CT scans of the samples were performed using a micro-CT scanner (Skyscan High Resolution Model 1176) with nominal resolution of 35 μm, a 0.2 mm aluminum filter, and tube voltage of 45 kV. Reconstruction was done with a modified Feldkamp algorithm using the SkyScanNRecon software accelerated by GPU. Ring artifact reduction, Gaussian smoothing (3%), and beam hardening correction (25%) were applied. Volume-rendered three-dimensional (3D) images were generated using an RGBA transfer function in the SkyScan CT-Volume ("CTVol") software and in the SkyScan CT-Voxel ("CTVox") software.

Immunofluorescence Analysis

Spinal cords were dissected, fixated in 4% PFA overnight, cryoprotected with 30% sucrose solution overnight, and embedded in optimal cutting temperature compound (OCT) and longitudinally sectioned (20 μm) using a cryostat (Leica CM1850, Germany). Sections were permeablized in 0.5% Tween solution, blocked with 5% bovine serum, and then incubated with rabbit-anti-tubulin (Abcam, 1:500), rabbit-anti-GFAP (1:1000, Millipore), mouse-anti-CD11b (1:500, BioRad,) or mouse-anti-CD31 (1:50, BD) antibodies overnight at 4° C. Next, sections were incubated with goat-anti-rabbit-Alexa647 (Invitrogen, 1:800), and DAPI (1:1000) for 3 h, mounted with coverslips, and imaged using confocal microscope (LSM700).

Spinal Cord Injury Model

All animal experiments were performed in strict compliance with protocols approved by the Technion-Israel Institute of Technology. Animal randomization was performed by an experimenter blinded to the treatments. Adult female Sprague-Dawley rats were anesthetized with a mixture of xylazine (10-15 mg/kg) and ketamine (60-90 mg/kg) and with a maintenance dose of 1-2% isoflurane (Harvard Apparatus, USA) during surgery. After laminectomy at the 9th-11th thoracic vertebral levels, the spinal cord was completely transected at the T10 level, using a microscissor (Kent Scientific, USA). The rostral and caudal stumps were lifted to ensure complete transection and a hook (Kent Scientific, USA) was passed circularly inside the generated gap to confirm that no fibers remained at the bottom part of the spine canal. The groups evaluated in this study were designated as transection control (n=15), intranasal exosomes control (n=10), intranasal ExoPTEN (n=7), intralesional PTEN-siRNA (n=3) and intralesional ExoPTEN (n=4). Muscle layers and skin were then sutured and the rats were placed in temperature-controlled incubation chambers.

For intranasal treatments, rats were intranasally given 40 μl saline, 40 μl exosomes, or 40 μl ExoPTEN, 2-3 h post-operation, and every 24 h, for 5 days. For intralesional treatments, rats were given 40 μl PTEN-siRNA (0.1 nmol) or 40 μl ExoPTEN once only, when the spinal cord injuries were made. Bladder massages were performed twice daily until bladder function was regained. Antibiotics (Cefazolin, 25 mg/kg, twice daily) were injected daily, for 1 week. Buprenorphine (Bayer) was administered at a dose of 0.01-0.05 mg/kg before surgery and 3 days after. Cyclosporin (10 mg/kg/d) (Novartis) was administered for 1 week, to all rats.

Behavioral Analysis

Motor recovery was assessed and scored by a blinded experimenter using Basso, Beattie, and Bresnahan (BBB) locomotor scale method. Measurements were made 2-3 days following implantation, and then once every 7 days. All measurements were made at the same time of day to avoid circadian variability. Baseline BBB was defined as the value recorded at the first test after surgery. The weekly score was the lowest score obtained during each calendar week. Sensory recovery was assessed using the von Frey filament test. Filaments (Bioseb) with a gradient of bending forces, were applied on the paws to elicit nociceptive responses (quick paw withdrawals from the stimuli). The withdrawal threshold value is defined as the minimal force inducing positive responses in at least 2 out of 3 trials, with at least 30 s between trials.

MRI

MRI was performed with a 9.4T bore scanner (Bruker Biospec, Ettlingen, Germany), using a cylindrical volume coil (86 mm inner diameter) for signal excitation and a single channel surface coil (20 mm diameter) for signal reception. Animals were under anesthesia (0.5-1.5% isoflurane) and supplemented with oxygen (0.5 L/min). Respiration was monitored during imaging (Small Animal Instruments, Stony Brook, New York, N.Y.) and body temperature was maintained using thermostat-regulated circulating hot water. Prior to the DTI imaging, sagittal and axial T2-weighted anatomical scans were acquired using RARE sequence to determine the DTI scan slice geometry. The RARE acquisition parameters were: 0.8 mm thickness, FOV=3×3 cm, matrix dimension=192×192, (spatial resolution=156×156 repetition/echo time (TR/TE)=1200/16.22 ms, 4 averages. DTI imaging was obtained using an EPI-DTI sequence with the following parameters: 30 non-collinear gradient directions, 3 $A_0$ images, b=1000 s/mm$^2$, diff duration (δ)=2.6, diff separation (Δ)=11, 2 averages, 0.8 mm thickness, FOV=3×3 cm, matrix dimension=192×192, (spatial resolution=156×156 μm$^2$). DTI calculations and fiber tracking were performed using the ExploreDTI software (Leemans et al., 2009). The tensors obtained were spectrally decomposed to their eigen-components. The eigen-values were used to calculate fractional anisotropy (FA) maps. Regions of interest (ROIs) of the spinal cord (white and gray matter) were manually segmented in each slice. Tractography was applied using deterministic (streamline) fiber tracking, terminating at voxels with FA lower than 0.2 or following a tract orientation change higher than 30° (Basser et al. 2000), with 0.078 mm step size, and 0.2-100 mm fiber length. Fibers that passed through the manually selected ROIs were plotted as streamlines.

Electrophysiology

At week 8, electrophysiology was performed to record neural signal propagations through the lesion. Following ketamine/xylazine anesthesia, rats were placed in a stereotaxic apparatus and a midline incision was made in the head skin. The cranium was exposed and two electrical stimulation screw electrodes were implanted 2 mm to the right of the midline, at −1.0 mm and +4.0 mm anterior and posterior to the bregma, respectively. The screw electrodes were connected to the output terminals of a stimulator. The sciatic nerve at the rear of the leg was exposed and two silver wire hook electrodes were inserted. Another wire was inserted into the footpad of the leg and served as a ground electrode. The amplified signals were band-pass filtered between 0.1 and 3 kHz (7P511 AC wideband preamplifier with 7DA driver amplifier, Grass Technologies, Warwick, R. I.), digitized (NI USB-6341 analog-to-digital converter, National Instruments), acquired at 10 kHz and stored on a personal computer running the WinWCP software package (courtesy of Dr. John Dempster, University of Strathclyde, UK). The stimulation intensity was chosen according to hindlimb contraction and appearance of the reliable sciatic nerve compound action potential (CAP) in the first animal, and maintained throughout the experiment.

Western Blotting

Lesioned spinal cord segments and livers were placed in RIPA solution ((1% sodium deoxycholate (DOC) (Sigma), 1% 100×-Triton (Biolab), 50 mM Tris-HCl (Sigma), 150 mM NaCl (Sigma), 5 mM EDTA (Sigma)) containing a protease inhibitors cocktail (100 mM PMSF, 2 mg/ml leupeptin, 50 mM Na-orthavanadate, 50 mM aprotinin, Sigma). Tissues were homogenized and 20 μs total protein were separated by 4-12% SDS-PAGE and then transferred to a nitrocellulose membrane for 90 min. After blocking with 2% BSA in tris-buffered saline with 0.1% Tween20 (TBST) for 3 h, membranes were incubated overnight with anti-PTEN, 1:1000 (mouse monoclonal; Cat. #9556, Cell Signaling) or anti-β-actin, 1:1000 (rabbit monoclonal; Cat. #8457, Cell Signaling) as a loading control, in 2% BSA in TBST. The next day, after three TBST rinses, membranes were incubated with anti-rabbit IgG-HRP (1:5000, NA934V, GE Healthcare) or anti-mouse IgG-HRP (1:5000, NA93 IV, GE Healthcare) for 2 h, at RT. The signals were developed by exposing the blot to enhanced chemiluminescent reagents (Cat. #1705061, BioRad) and subsequent exposure in a LAS-3000 imaging system (FujiFilm).

RT-qPCR

Total RNA from the lesioned spinal cord tissues and livers was extracted using Qiagen RNeasy Mini Kit and first strand DNA was synthesized using the High Capacity cDNA Reverse Transcription Kit (Applied Biosystems) according to the manufacturer's instructions. Real-time quantitative PCR was performed on the QuantStudio 12K Flex Real-Time PCR System. Primers included PTEN (Thermo Fisher, Assay ID: Rn00477208) or GAPDH (Thermo Fisher, Assay ID: Rn01775763-g1). The amplification reaction conditions were: 95° C. for 20 s, followed by 40 cycles of 95° C. for 3 s, 60° C. for 30 s, in 10 μl reactions, in triplicates. Relative expression levels were determined using the ΔΔCt method, where the gene of interest was standardized to GAPDH expression.

Neuroanatomical Tracing

To trace corticospinal axons, rats underwent anterograde tracing with biotinylated dextran amine (BDA) at week 6. Under ketamine and xylazine anesthesia as described above, rats were positioned in a stereotaxic frame. The scalp hair was shaved and the area swabbed with ethanol, and small holes were drilled in the skull over the sensorimotor cortices. A Hamilton microsyringe with a pulled glass micropipette was used to inject 1 μl of 10% BDA (MW 10,000, D1956, Molecular Probes) over 2 min per site, with 2 min intervals between injections, into 8 sites per hemisphere using the following coordinates: AP±1.0, ML±2.0; AP 0, ML±1.5;

AP–1.0, ML±1.5; AP–2.0, ML±1.5; DV 1.5 mm. After all injections were completed, the scalp was sutured, and rats were left in a recovery chamber until they recovered. At week 8, the rats were deeply anesthetized with ketamine and xylazine and transcardially perfused with 4% PFA. The segments of the spinal cord containing the lesion were harvested, cyroprotected in 30% sucrose, embedded in OCT and sectioned longitudinally, to 20 μm-thick slices. Sections were washed three times in PBS and 0.1% Triton X-100, incubated overnight at 4° C., with Alexa Fluor594-conjugated streptavidin (1:500, Invitrogen, S32356), rinsed three times in PBS, mounted and covered with a coverslip.

Statistical Analysis

Statistical analyses were performed using MATLAB/Prism 5 software (USA). Two-tailed unpaired Student's t test was used to compare between two groups. Unless otherwise stated, the rest of the data were analyzed using either one-way or two-way ANOVA, with post-hoc Tukey's multiple comparisons. All grouped data are presented as means±SEM. Significance levels: *$p<0.05$, $p<0.01$, *$p<0.001$, ****$p<0.0001$.

Example 1—Intranasal MSC-Exo Cross the BBB, and Migrate to Spinal Cord

Figure 1:
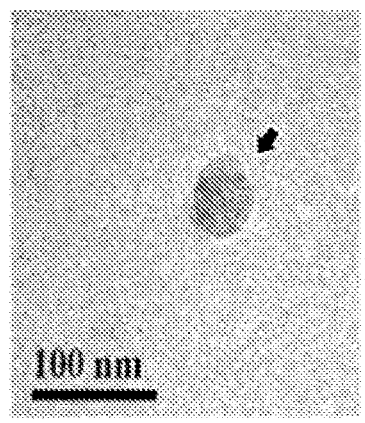
FIG. 1 shows the visualization of MSC-Exo by Cryo-TEM.
Figure 3:
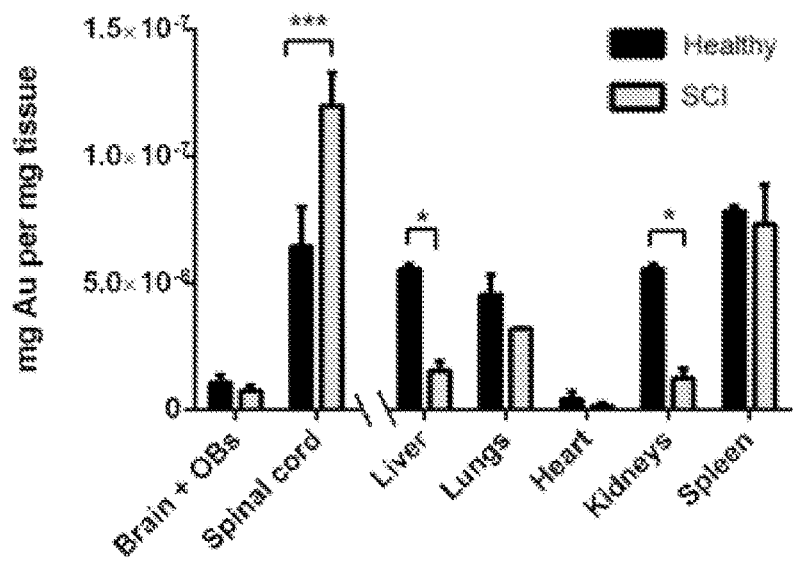
FIG. 3 shows quantification of gold-nanoparticle (GNPs) upon intranasal administration of GNP-exosomes using inductively coupled plasma (ICP) assessment in the CNS (left panel), and major organs (right panel), using FAAS, in healthy and injured rats. $*p<0.05$, $***p<0.001$.
Figure 4:
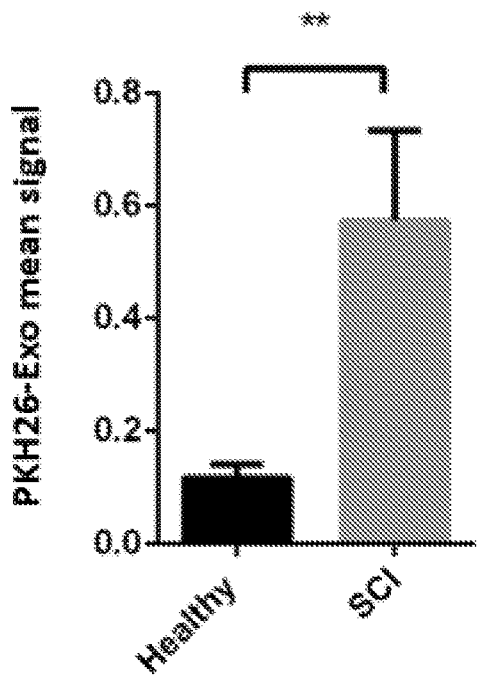
FIG. 4 shows quantification of PKH26 mean signal intensity in the T10 spinal segment using PKH26 labeled exosomes (PKH26-Exo) in intact and injured rats. $**p<0.01$.

Exosomes isolated from mesenchymal stem cells exosomes (MSC-Exo) were of mean size 111±64 nm and at a concentration of $40.43 \times 10^8$ particles/ml (FIG. S1D-E). MSC-Exo visualized with Cryo-TEM, showed a typical sphere shape. In order to examine whether MSC-Exo can cross the BBB, we labeled MSC-Exo with gold nanoparticles (GNPs), as described in (Betzer et al., 2017, *ACS Nano* 11, 10883-10893). Cryo-TEM imaging of the MSC-Exo loaded with GNPs indicated GNP uptake into the exosomes (FIG. 1). To examine whether MSC-Exo can cross the blood brain barrier after intranasal (IN) administration, GNP-loaded MSC-Exo were IN administered three hours after complete spinal cord transection. Micro-CT scanning 24 h post-administration demonstrated significant GNP accumulation in the spinal cord lesion area, but not in the brain (FIG. 2, upper panel). In contrast, in healthy controls, the GNPs were localized mainly in the brain and olfactory bulbs (FIG. 2, lower panel). Inductively coupled plasma (ICP) assessments confirmed that the amount of GNPs in the T10 spinal segment area, was significantly higher in the injured rats as compared to healthy controls (FIG. 3A, one-way ANOVA F $(3, 8)=27.5$, $p<0.001$, Tukey). Similarly, a significantly higher amount of IN-administered PKH26 (red lipophilic dye)-labeled exosomes accumulated at the T10 spinal segment area of injured, as compared to healthy rats (FIG. 4, t $(14)=3.21$, $p<0.01$). The qualitative micro-CT scan and quantitative ICP test of the CNS, along with immunofluorescent staining of spinal lesions, showed that MSC-Exo penetrated the blood-brain-barrier, and homed to the spinal cord lesion. Unexpectedly, rats with spinal cord injury the MSC-Exo was significantly more prevalent in the area of injury, while in healthy rats in brain.

To study the bio-distribution of MSC-Exo after intranasal administration, flame atomic absorption spectroscopy (FAAS) was deployed to quantify the GNPs in major organs (liver, lungs, heart, kidneys and spleen), 24 h post-administration. No significant difference was found between the MSC-Exo levels in healthy versus injured rats in the lungs, heart and spleen. However, higher levels were found in the liver and kidneys of healthy rats compared to injured rats, indicating a more rapid excretion of MSC-Exo in intact rats (FIG. 4, right panel, one-way ANOVA F $(9, 10)=12.92$, $p<0.001$, Sidak's multiple comparisons test).

Figure 5:
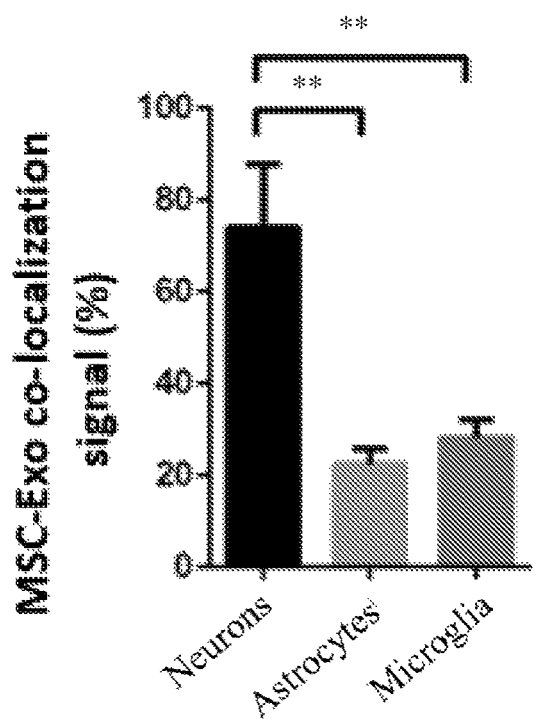
FIG. 5 shows quantification of PKH26-Exo signals co-localized with neurons, astrocytes and activated microglia ($p<0.01$)

Further we have showed that blocking chemokine receptors of PKH26 (red)-labeled exosomes with pertussis toxin dramatically reduced MSC-Exo' ability to migrate to the lesion. To determine whether preferential uptake of MSC-Exo by specific cell types existed in the spinal cord lesion, neurons, astrocytes and microglia in the lesioned segments were immunostained 24 h after IN administration of PKH26-Exo to 2-3 h post-injury rats. We found that MSC-Exo co-localized mainly in neurons, and much less in astrocytes and activated microglia (FIG. 5, one-way ANOVA, F $(2, 13)=11.59$, $p>0.01$, Tukey).

Example 2. PTEN-siRNA Loaded into MSC-Exo Promotes Robust DRG Neuron Outgrowth In Vitro MSC-Exo were load with cholesterol conjugated non-coding cy3-MAPK-siRNA as described in materials and methods. Nanosight analysis demonstrated efficient cy3-MAPK-siRNA loading (33.64%) (FIG. 6).

Figure 8:
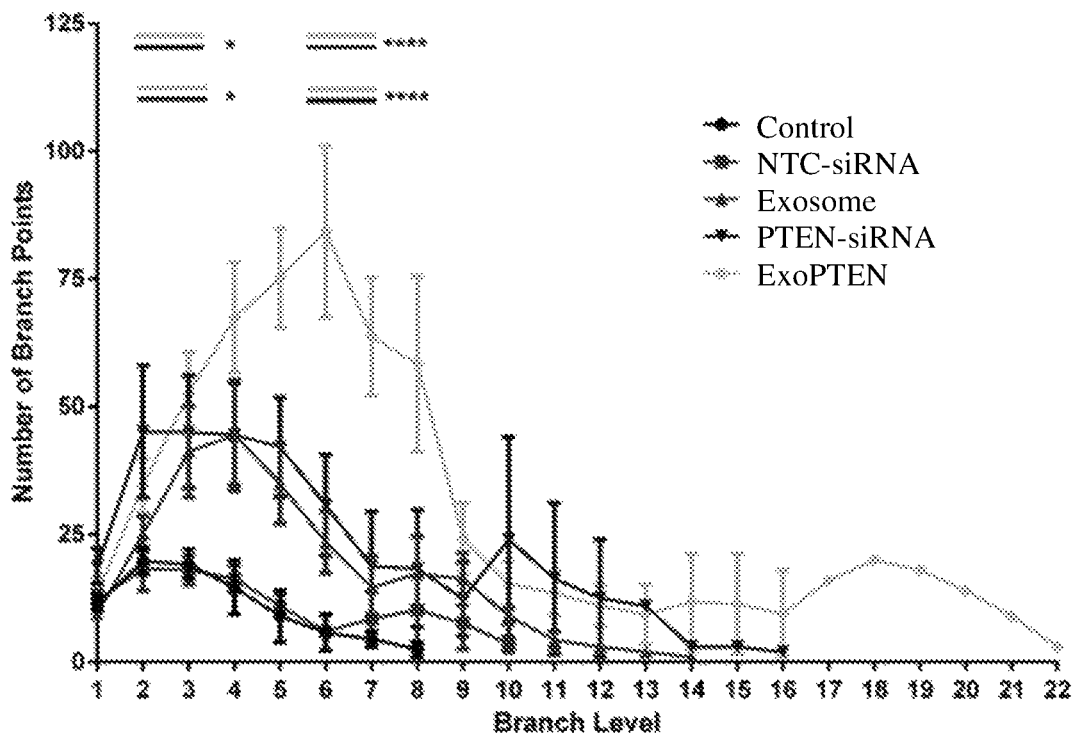
FIG. 8 shows the number of branch points with respect to branch level across all groups. Number of branch points at median branch levels quantified by IMARIS software was compared across groups. At median branch level, PTEN-siRNA-exosomes promoted significantly higher number of neurite branch points than all other groups.
Figure 9A:
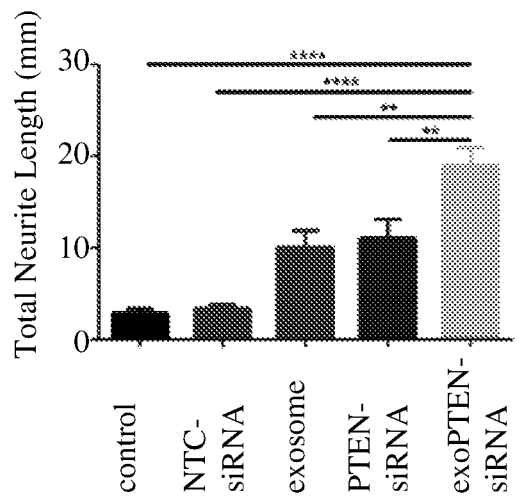
FIG. 9 shows the total neurite length (FIG. 9A), neurite count (FIG. 9B), number of branch points (FIG. 9C), and maximum branch level (FIG. 9D) measured and compared in all groups.
Figure 9B:
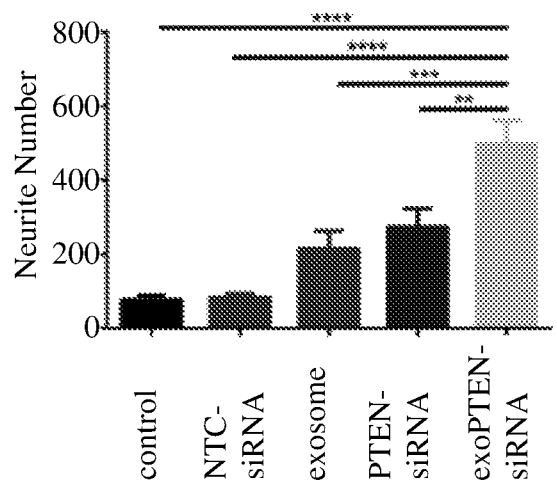
Figure 9C:
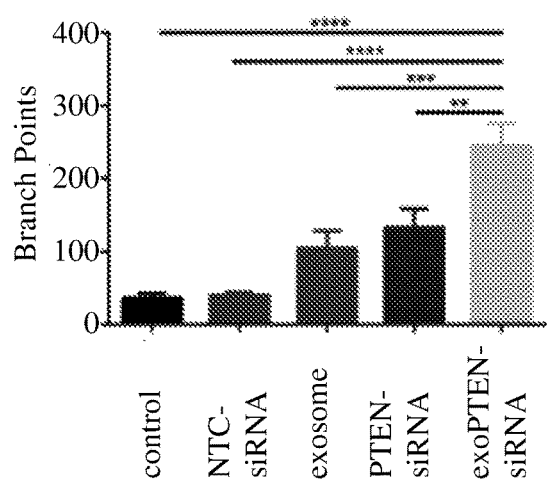
Figure 9D:
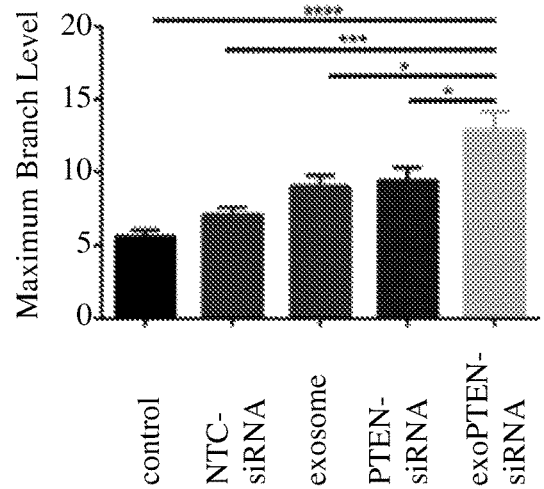

To test whether PTEN inhibition, delivered by MSC-Exo comprising siRNA, can regulate axonal growth, we then loaded self-deliverable PTEN-siRNA into MSC-Exo, hereafter termed ExoPTEN, to dorsal root ganglia (DRG) neurons in culture. One day after ExoPTEN treatment, the DRG neurons featured a more complex, branched and elongated morphology, as compared to neurons treated with medium only, non-targeting control siRNA (NTC-siRNA), MSC-Exo, or PTEN-siRNA only (FIG. 7). At median branch levels, ExoPTEN-treated neurons exhibited a significantly higher number of branch points (FIG. 8, one-way ANOVA, $p<0.001$, Tukey). Total neurite length, neurite count, branch points and maximum branch level were all significantly higher in ExoPTEN-treated neurons; more specifically, being 6.6-fold, 6.6-fold, 6.8-fold, 2.3-fold higher than the neurons without any treatment, respectively (FIG. 9, one-way ANOVA, all $p<0.001$, Tukey). Both MSC-Exo and PTEN-siRNA alone induced DRG neuron outgrowth to a similar extent, but less dramatically than the ExoPTEN-treatment.

Example 3. Intranasal ExoPTEN Silences PTEN Expression in Spinal Cord Lesions

Figure 10A:
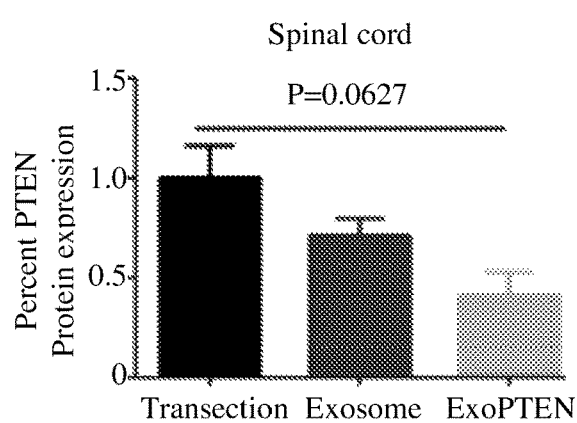
FIGS. 10A and B show PTEN protein expression in the spinal cord and liver, respectively, in Exosome (IN)-treated, and ExoPTEN (IN)-treated, compared to the untreated SCI rats.
Figure 10B:
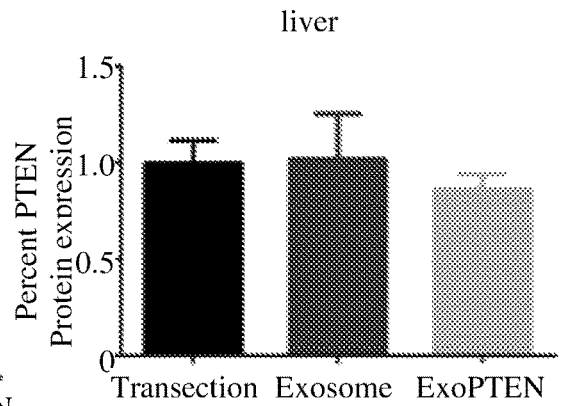
FIG. 10 shows protein and mRNA expression at the site of SCI and in the liver upon intranasal administration of ExoPTEN.
FIGS. 10C and D show RT-qPCR analysis of PTEN mRNA expression in the spinal cord and liver in untreated, Exosome (IN)-treated and ExoPTEN (IN)-treated SCI rats, with GAPDH as the internal control. Data are presented as mean±SEM, with Kruskal-Wallis multiple comparisons; IL: intralesional; IN: intranasal.
Figure 10C:
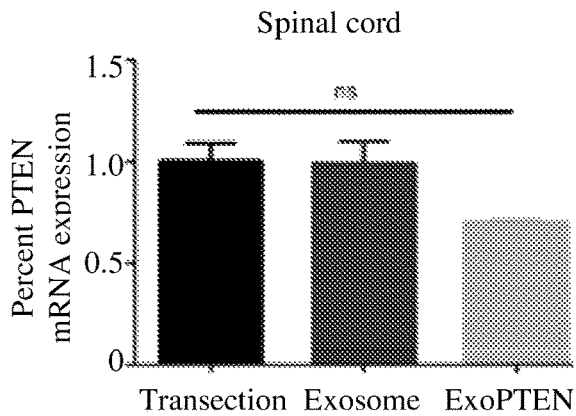
Figure 10D:
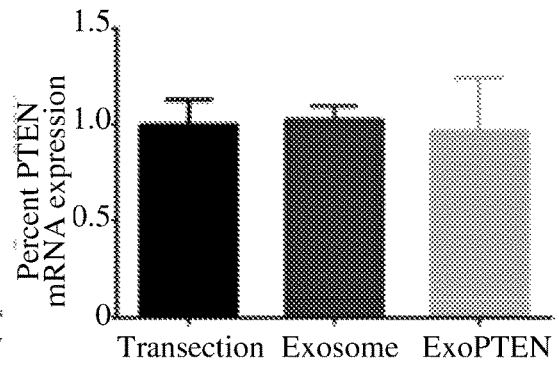

To check the silencing effect of ExoPTEN in vivo, ExoPTEN were intranasally administered for 5 consecutive days starting from the day of complete spinal cord transection. At week 8, Western blot analysis of the proteins extracted from the SCI area showed a 59% reduction in PTEN protein levels in ExoPTEN-treated as compared to untreated SCI rats (FIG. 10A, Kruskal-Wallis test, $p=0.0627$). No significant changes were found in the protein levels in liver tissues among the groups (FIG. 10B, $p=0.8643$). In parallel, RT-qPCR analysis showed a 32% reduction in PTEN gene expression in the ExoPTEN-treated as compared to untreated SCI rats (FIG. 10C, $p=0.1520$), while the gene expression was comparable in the livers (FIG. FIG. 10D, $p>0.9999$).

Figure 11A:
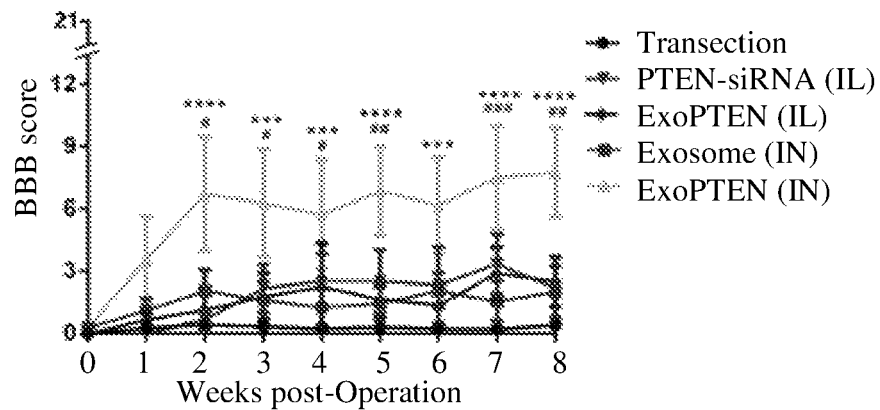
FIG. 11A shows weekly Basso, Beattie, and Bresnahan (BBB) locomotor scores of SCI rats: untreated (n=15, black), or treated with PTEN-siRNA (IL) (n=3), ExoPTEN (IL) (n=4), exosome (IN) (n=10), or ExoPTEN (IN) (n=7); IL: intralesional; IN: intranasal. Two-way ANOVA followed by Tukey's multiple comparisons test (*$p<0.001$, **$p<0.0001$ between transection control and ExoPTEN (IN)). #$p<0.05$, ##$p<0.01$, ###$p<0.001$ between Exosome (IN) and ExoPTEN (IN).
Figure 11B:
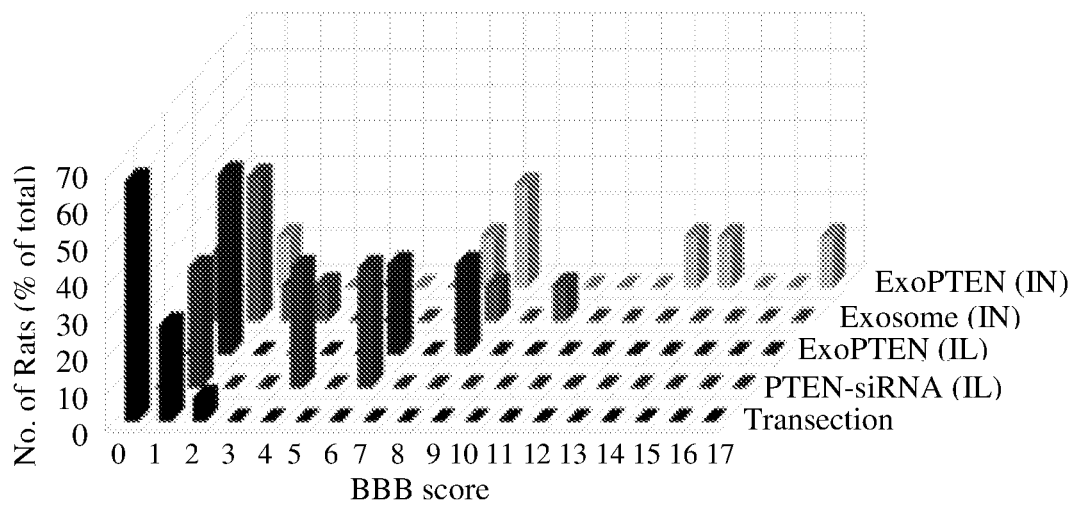
FIG. 11B shows distribution of the BBB locomotor scores per group throughout the 8 week period. The highest score achieved by each rat in each group is presented. The ratio of the number of rats with a given score and the total number of rats in each group is expressed.
Figure 11C:
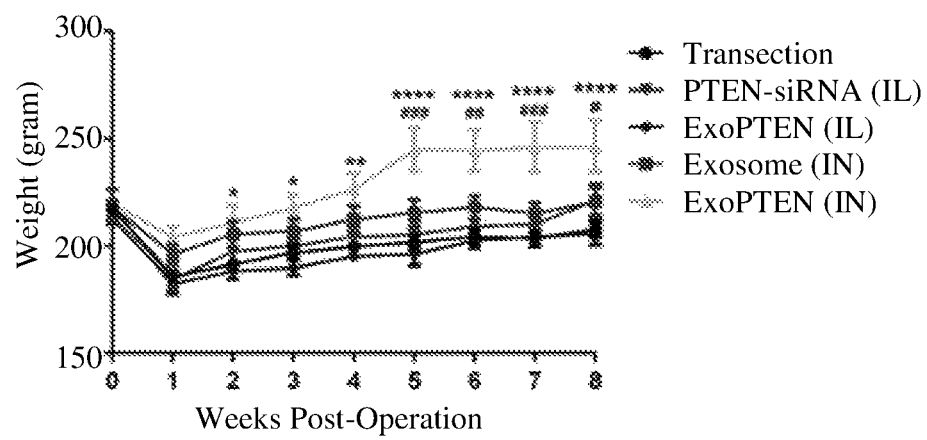
FIG. 11C shows mean weekly body weights (±SEM) in transection controls, or rats treated with PTEN-siRNA (IL), ExoPTEN (IL), Exosome (IN), or ExoPTEN (IN). Two-way ANOVA followed by Tukey's multiple comparisons test. *$p<0.05$, $p<0.01$, **$p<0.0001$ between transection controls and ExoPTEN (IN). #$p<0.05$, ##$p<0.01$, ###$p<0.001$ between Exosome (IN) and ExoPTEN (IN).
Figure 11D:
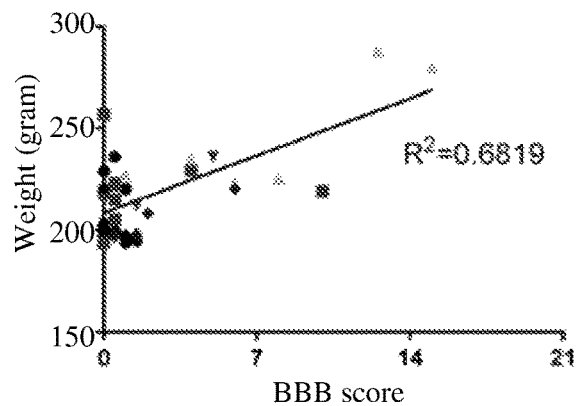
FIG. 11D shows body weight in relation to BBB scores per group at week 8. Pearson's coefficient correlation, denoted as $R^2$, was calculated, showing high correlation between BBB scores and weights for all groups.
Figure 11E:
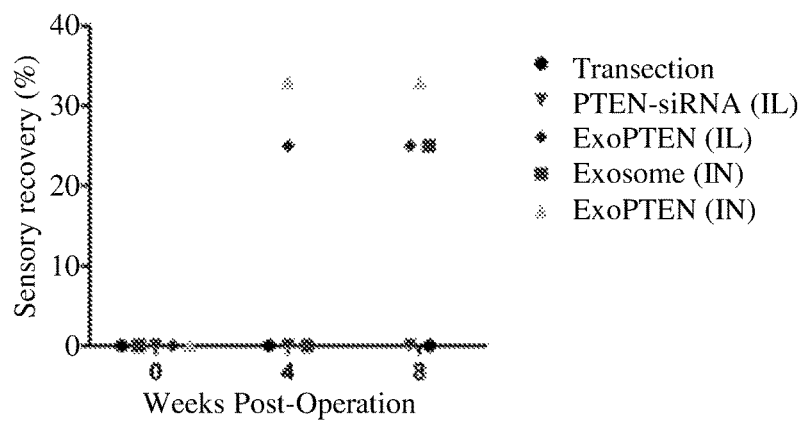
FIG. 11E shows percentage of sensory recovery at weeks 0, 4, 8 post-treatment.
Figure 11F:
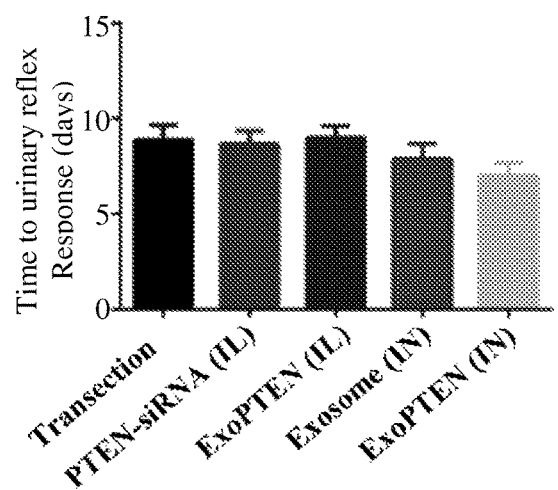
FIG. 11F shows bladder function reflected as a time to achieve spontaneous urinary reflex (days) from initiation of treatment.
Figure 11G:
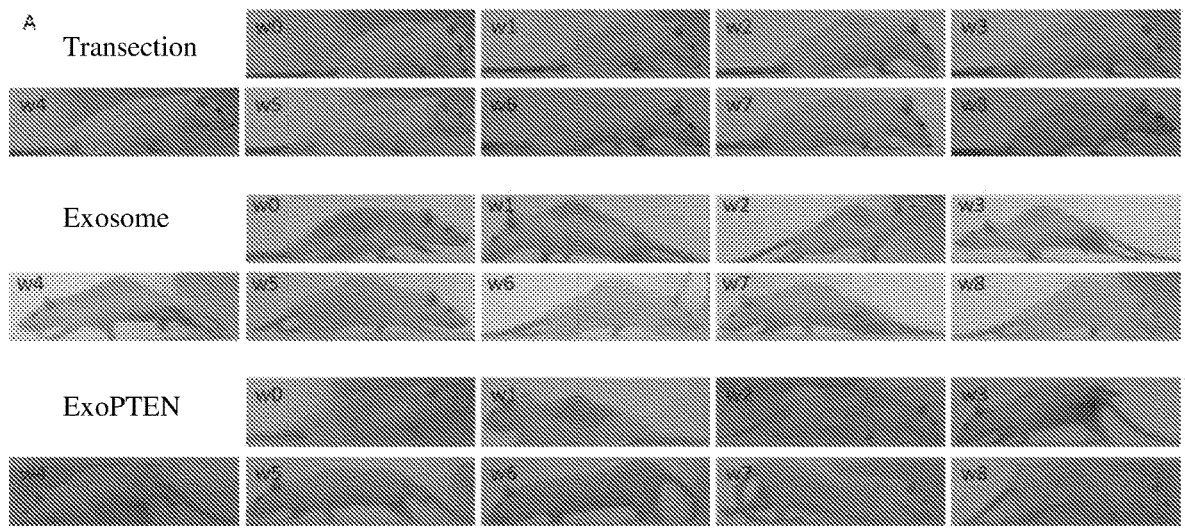
FIG. 11G shows images of rats after transection: untreated (upper panel), exosome-treated (medial panel), and PTEN-siRNA-exosome-treated (lower panel), from day 3 to week 8 post-operation.

Example 4. Intranasal ExoPTEN Enables Significant Functional Recovery in Complete SCI Rats To assess the neuroprotective potential of ExoPTEN treatment, rats with complete SCI were divided into five groups, (1) no treatment, (2) intralesional (IL) PTEN-siRNA treatment, (3) intralesional ExoPTEN single administration, (4) exosomes administered IN for 5 consecutive days and (5) ExoPTEN administered IN for 5 consecutive days (starting from the day of injury). Rats were subjected to BBB locomotor scoring every week, for 8 weeks. Five days of IN ExoPTEN administration led to significant locomotor recovery (yielding F (4, 300)=35.72, p<0.0001, F (8, 300)=2.931 p<0.001 respectively) as compared to all other treatment groups. More specifically, at week 8, the average BBB locomotor score in the ExoPTEN (IN) group (FIG. 11A) reached 7.75±2.14, a sharp contrast to the mean 0.39±0.14 score in untreated transection rats (p<0.001). A statistically significant difference was observed between groups treated intranasally with ExoPTEN and those treated intranasally with empty exosomes (FIG. 11A). Slight, but not statistically significant (all p>0.05), improvements were measured at week 8 in the PTEN-siRNA (IL), ExoPTEN (IL), and Exosome (IN) groups, with BBB locomotor scores of 2.17±1.48, 2.50±1.21, 2.00±1.23, respectively (FIG. 11A). Throughout the 8 weeks, 28.6% of ExoPTEN (IN)-treated rats exhibited a BBB locomotor score ≥14, reflecting consistent plantar stepping, toe clearance, and consistent forelimb-hindlimb coordination, while none of the other treated groups were able to achieve this level of locomotor improvement (FIG. 11B). ExoPTEN (IN)-treated rats also gained weight faster than the other groups and plateaued at week 5 (FIG. 11C). Furthermore, at week 8, a positive correlation between rat weight and BBB locomotor scores was noted (FIG. 11D, Pearson's coefficient correlation=0.6819, p<0.0001). Von Frey filament tests with a gradient of bending forces (6, 8, 10, 15, 26, 60, 100, 180, 300 g) was applied on the hind limbs to determine the paw withdrawal threshold, as an indicator of sensory recovery. The cutoff threshold to elicit paw withdrawals in healthy rats was set at 60 g, below which withdrawal responses were considered allodynia. None of the rats responded to 300 g filament hair after SCI, indicating complete abolishment of the sensory function. Normal sensory response reached 25% and 33.3% of animals in ExoPTEN (IL), and ExoPTEN (IN), respectively, at week 4, and remained the same at week 8. Additionally, 25% of rats in the Exosome (IN) group attained sensory recovery at week 8. In contrast, the untreated and PTEN-siRNA (IL) groups did not show any sensory recovery within the 8 weeks (FIG. 11E). Time to urinary reflex responses, reflecting bladder function, was regained fastest by ExoPTEN (IN) animals (7.0±0.7 days), followed by the untreated rats (8.9±0.7 days) (FIG. 11F, one-way ANOVA, p=0.4079, Tukey). FIG. 11G shows the difference in recovery of rats for 8 week after lesion that were treated with control, exosomes and ExoPTEN.

Figure 12A:
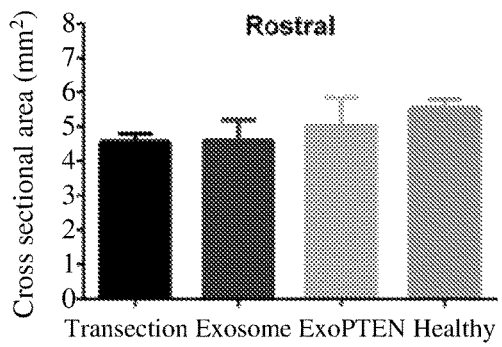
FIG. 12A and FIG. 12B show cross-sectional area 4 mm rostral and caudal to the injury epicenter, respectively.
Figure 12B:
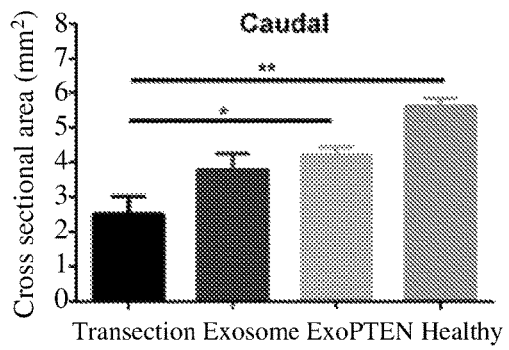
Figure 12C:
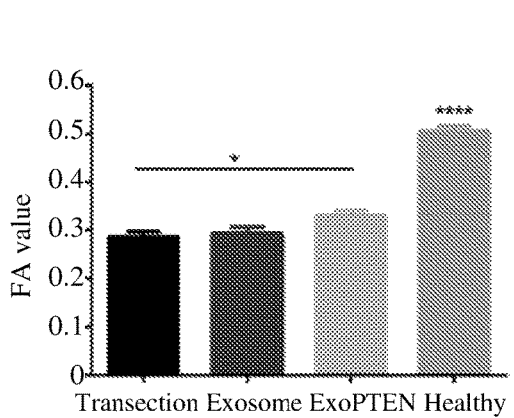
FIG. 12C shows average fractional anisotropy (FA) values within the lesion.
Figure 12D:
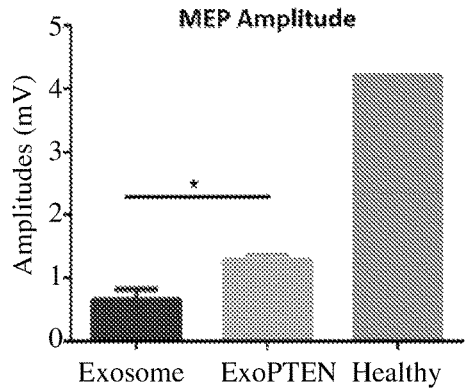
FIG. 12D and FIG. 12E show amplitude (FIG. 12D) and latency (FIG. 12E) of motor-evoked potentials in Exosome (IN), ExoPTEN (IN) or healthy rats.
Figure 12E:
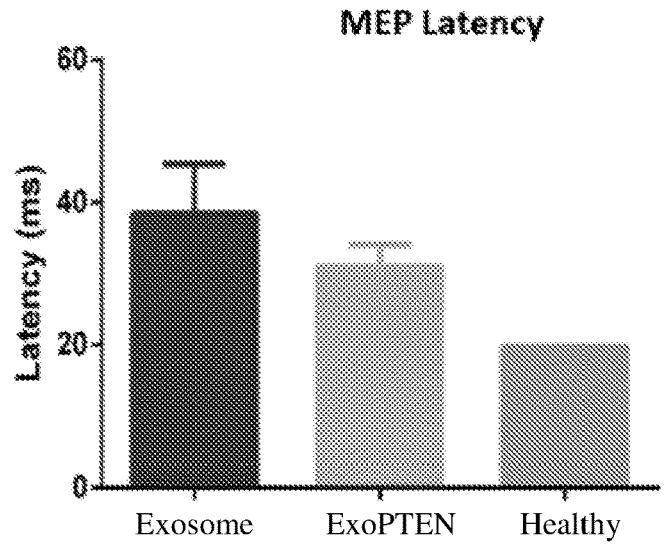

Example 5. Intranasal ExoPTEN Induces Structural Organization and Electrophysiological Conduction To assess structural integrity of the spinal cord, 9.4T conventional MM and diffusion tensor imaging (DTI) were performed in untreated SCI animals, Exosome (IN)- or ExoPTEN (IN)-treated SCI animals, and intact rats. Severe spinal cord atrophy, 4 mm caudal to the injury epicenter, was observed in the transection controls, while such degeneration was less obvious in the Exosome and ExoPTEN groups. Cross-sectional areas quantified 4 mm rostral to the injury epicenter, were not significantly different between the SCI groups (FIG. 12A, one-way ANOVA, F (3, 11)=0.6120, p=0.6212), but was dramatically reduced, 4 mm caudal to the epicenter, in the transection controls as compared to the ExoPTEN-treated group (FIG. 12B, 2.5±0.5 mm$^2$ vs 4.2±0.3 mm$^2$, p<0.05). Diffusion Tensor Imaging (DTI) tractography showed complete disconnection of the rostral and caudal stumps in the transection group, partial bridging in the Exosome group, and the most noticeable bridging in the ExoPTEN group. Fractional anisotropy (FA) recordings rostral and caudal to the injury site were higher in ExoPTEN-treated rats compared to the Exosome or untreated SCI groups, but were still lower than in intact rats (average FA values within the lesion in transection control, Exosome, ExoPTEN, and intact rats were 0.2856, 0.2938, 0.3293, 0.5055, respectively, FIG. 12C). Mean diffusivity (MD) recordings did not show differences between untreated, Exosome, and ExoPTEN SCI groups. In addition, high-amplitude motor-evoked potentials (MEPs) were observed propagating from the motor cortex through the lesion to the sciatic nerve of rats treated with ExoPTEN, while low-amplitude signals were measured in the exosome group (FIG. 12D, 1.283±0.085 mV vs 0.662±0.162 mV, respectively, p=0.0273. The latency of MEP in ExoPTEN treated group was shorter than in exosome treated group (FIG. 12E, 31.03±3.05 ms vs 38.49±6.78 ms, p=0.3726). All signals were abolished after re-transection rostral to the spinal cord lesion.

Figure 13A:
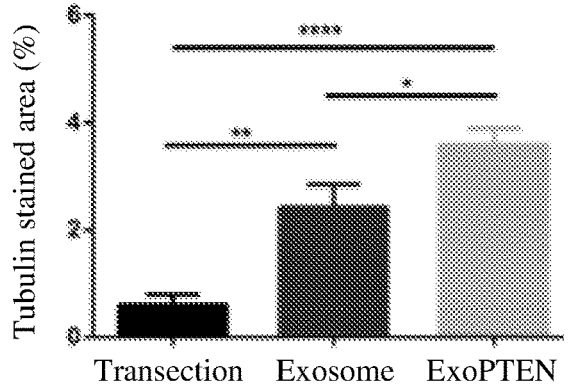
FIG. 13 shows a quantification and comparison of immunofluorescent markers in the three groups of rats: untreated, treated with exosomes and treated with ExoPTEN. The markers are β-III-tubulin (FIG. 13A), CD11b (FIG. 13B), GFAP (FIG. 13C), and CD31 (FIG. 13D). Data are presented as mean±SEM, and one-way ANOVA followed by Tukey's multiple comparisons test (*$p<0.05$, $p<0.01$, **$p<0.0001$).
Figure 13B:
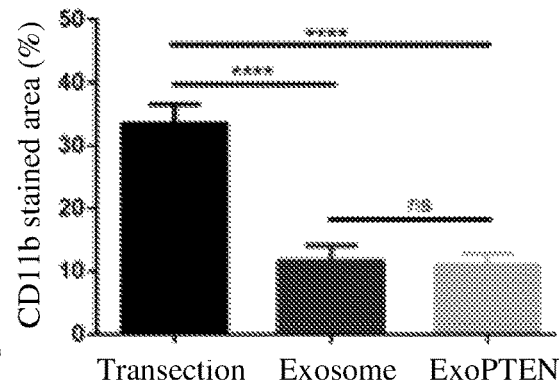
Figure 13C:
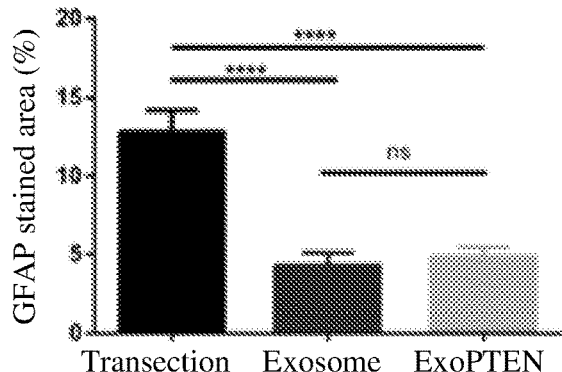
Figure 13D:
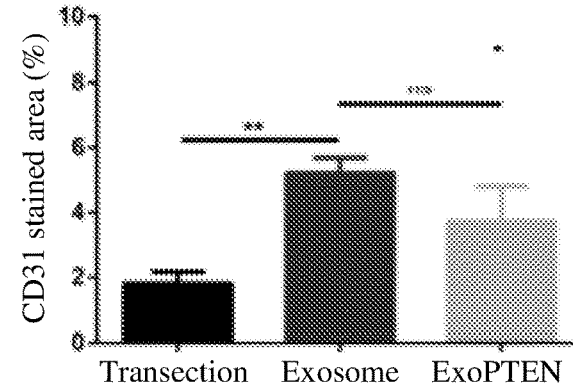

Example 6. Intranasal ExoPTEN Ameliorates Lesion Microenvironment and Regenerates Corticospinal Axons To identify the cellular mechanisms underlying locomotor recovery, spinal cord lesions in untreated, Exosome (IN)-treated, and ExoPTEN (IN)-treated animals were stained for β-III-tubulin, CD11b, GFAP and CD31 to detect axonal regeneration, microgliosis, astrogliosis and angiogenesis, respectively. β-III-tubulin expression was significantly higher in ExoPTEN-treated than Exosome-treated rats, while it was barely detectable in the untreated SCI rats (FIG. 13A, p<0.0001). CD11b-positive microglial cells were the most abundant cell type in the untreated transection group and were much less abundant in the Exosome and ExoPTEN groups (F (2, 24)=25.18, p<0.0001), with no significant difference between the two (FIG. 13B, panel 2, p=0.9818). A similar expression profile was observed for the GFAP$^+$ astrocytes (FIG. 13C). We found that the lowest level of angiogenesis, as measured by CD31$^+$ cells, was measured in the untreated transaction rats (FIG. 13D).

Figure 14:
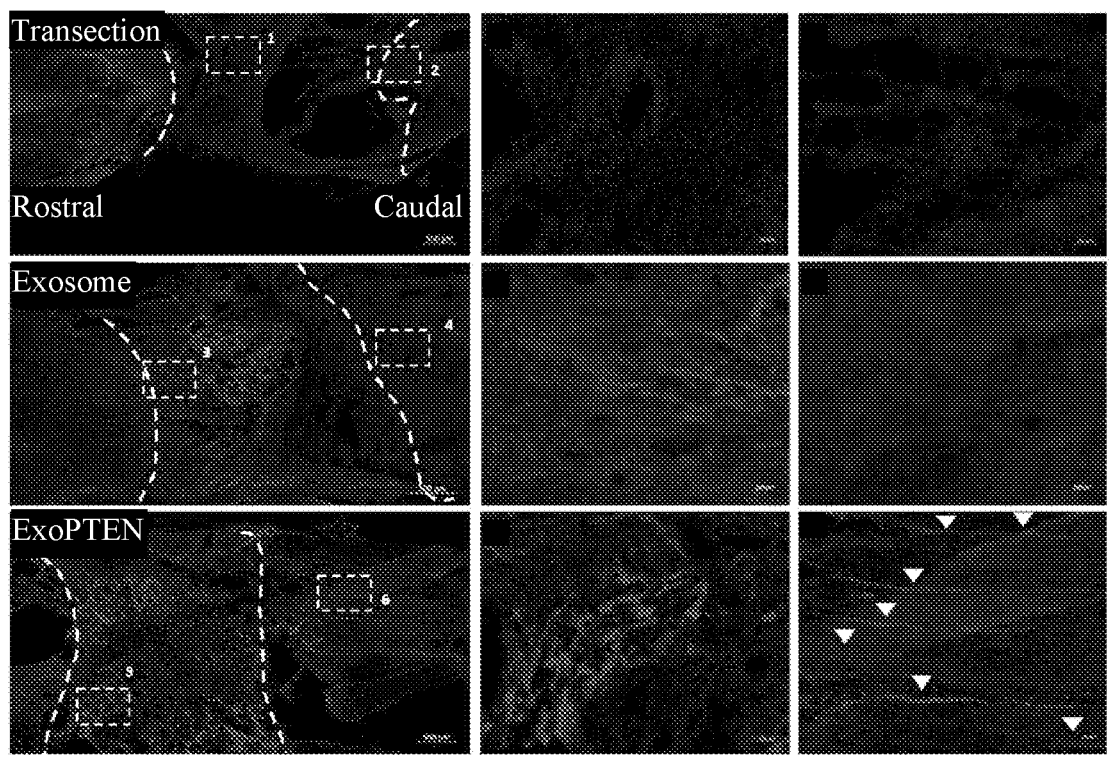
FIG. 14 shows representative images of BDA-traced corticospinal tract axons in untreated (upper panel, n=3), exosome-treated (middle panel, n=3), and ExoPTEN-treated (lower panel, n=2) SCI rats. Scale bar, 500 µm. Boxes show higher magnifications of the chosen areas. The white arrows denote BDA-positive fibers caudal to the epicenter. Scale bar, 100 µm. A much higher amount of axonal growth was observed after intranasal ExoPTEN treatment (top panel) as compared to the transection control or exosome treatment.

The corticospinal tract (CST) is responsible for voluntary motor control of the body and hindlimbs. To study whether intranasal ExoPTEN treatment can regenerate this specific tract, we traced its trajectory using biotinylated dextran amine (BDA), which was injected into the somatomotor cortex, in untreated, Exosome (IN), or ExoPTEN (IN)-treated SCI rats. We found that, in the untreated SCI group, BDA-positive fibers failed to penetrate into the lesion (FIG. 14, upper panel), while in the Exosome-treated group, BDA-positive fibers were seen within the lesion, but did not extend into the caudal stump (FIG. 14, middle panel). In contrast, in the ExoPTEN group, BDA-positive fibers were clearly seen penetrating and extending beyond the lesion (FIG. 14, lower panel).

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims. Although the present invention has been described herein above by way of preferred embodiments thereof, it can be modified, without departing from the spirit and nature of the subject invention as defined in the appended claims.

The invention claimed is:

1. A pharmaceutical composition for the treatment of neuronal injury or damage comprising extracellular vesicles loaded with an exogenous inhibitor of phosphatase and tensin homolog (PTEN) expression selected from siRNA targeting PTEN mRNA and shRNA targeting PTEN mRNA, wherein the extracellular vesicles are derived from bone marrow-derived mesenchymal stem cells (MSCs).

2. The pharmaceutical composition according to claim 1, wherein the extracellular vesicles are selected from exosomes, microvesicles, ectosomes, exovesicles and a combination thereof.

3. The pharmaceutical composition according to claim 1, wherein the inhibitor of PTEN expression is selected from (i) an siRNA comprising a nucleic acid sequence selected from SEQ ID NOs: 10, 11, 2, 3, 4 and 5; (ii) an siRNA targeting a nucleic acid sequence selected from SEQ ID NOs: 6 and 7; and (iii) an siRNA comprising a nucleic acid variants of (i) and (ii) having at least 80% sequence identity to the original sequence.

4. The pharmaceutical composition according to claim 1, wherein said inhibitor of PTEN expression further comprises a hydrophobic moiety.

5. The pharmaceutical composition according to claim 4, wherein said hydrophobic moiety is selected from the group consisting of a sterol, a ganglioside, a lipid, a vitamin, a fatty acid, a hydrophobic peptide, and a combination thereof, optionally wherein the sterol is cholesterol.

6. The pharmaceutical composition according to claim 1, wherein the composition is characterized by at least one of: (i) the extracellular vesicles are isolated extracellular vesicles; (ii) the composition further comprising chondroitinase ABC or extracellular vesicles comprising chondroitinase ABC; and (iii) the composition is formulated for administration via an administration route selected from intranasal, intra-lesion, intrathecal, intravenous, intramuscular, subcutaneous, sublingual, oral, and intracerebral administration route.

7. A method of treating a neuronal injury or damage in a subject in need thereof, comprising administering to the subject the pharmaceutical composition according to claim 1.

8. The pharmaceutical composition according to claim 1, wherein the composition is formulated for intranasal administration.

\* \* \* \* \*